United States Patent
Koide et al.

(10) Patent No.: US 12,421,178 B2
(45) Date of Patent: Sep. 23, 2025

(54) NON-CRYOGENIC, AMMONIA-FREE REDUCTION OF ARYL COMPOUNDS

(71) Applicant: University of Pittsburgh—Of the Commonwealth System of Higher Education, Pittsburgh, PA (US)

(72) Inventors: Kazunori Koide, Pittsburgh, PA (US); James Proviano Burrows, West Homestead, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 126 days.

(21) Appl. No.: 18/521,250

(22) Filed: Nov. 28, 2023

(65) Prior Publication Data

US 2024/0092708 A1    Mar. 21, 2024

Related U.S. Application Data

(62) Division of application No. 17/477,900, filed on Sep. 17, 2021, now Pat. No. 11,866,386.

(60) Provisional application No. 63/080,205, filed on Sep. 18, 2020.

(51) Int. Cl.
| | | |
|---|---|---|
| C07C 31/00 | (2006.01) | |
| C07B 31/00 | (2006.01) | |
| C07C 5/10 | (2006.01) | |
| C07C 41/20 | (2006.01) | |
| C07C 51/347 | (2006.01) | |
| C07C 67/30 | (2006.01) | |

(52) U.S. Cl.
CPC ............... *C07B 31/00* (2013.01); *C07C 5/10* (2013.01); *C07C 41/20* (2013.01); *C07C 51/347* (2013.01); *C07C 67/30* (2013.01); C07C 2523/04 (2013.01)

(58) Field of Classification Search
CPC ............ C07B 31/00; C07C 41/20; C07C 5/10
See application file for complete search history.

(56) References Cited

U.S. PATENT DOCUMENTS 4,533,760 A * 8/1985 Benkeser ............... C07C 41/20
568/667
5,675,038 A   10/1997 Dolby et al.

OTHER PUBLICATIONS

Kaiser et al. "Δ9, 10-Octalin", Organic Syntheses, 1988, pp. 1-6, vol. 6.
Kee et al., "Selective Bromination of sp3 C—H Bonds by Organophotoredox Catalysis", Asian J. Org. Chem., 2014, pp. 536-544, vol. 3.
Kobayashi et al., "Reductive Cleavage of 5,6-Dihydro-2H-pyran Derivatives; Facile Synthesis of cis-3-Hexenol", Synthesis, 1980, pp. 492-493.

(Continued)

*Primary Examiner* — Yate' K Cutliff
(74) *Attorney, Agent, or Firm* — The Webb Law Firm

(57) ABSTRACT

A method of reducing an aromatic ring or a cyclic, allylic ether in a compound includes preparing a reaction mixture including a compound including an aromatic moiety or a cyclic, allylic ether moiety, an alkali metal, and either ethylenediamine, diethylenetriamine, triethylenetetramine, or a combination thereof, in an ether solvent; and reacting the reaction mixture at from −20° C. to 30° C. for a time sufficient to reduce a double bond in the aromatic moiety to a single bond or to reduce the cyclic, allylic ether moiety.

18 Claims, 9 Drawing Sheets

(56) References Cited

OTHER PUBLICATIONS

Krapcho et al., "Kinetics of the Metal-Ammonia-Alcohol Reductions of Benzene and Substituted Benzenes", J. Am. Chem. Soc., 1959, pp. 3658-3666, vol. 81.
Lei et al., "A Practical and Chemoselective Ammonia-Free Birch Reduction", Org. Lett., 2018, pp. 3439-3442, vol. 20.
Ley et al., "A Highly Convergent Total Synthesis of the Spiroacetal Macrolide (+)-Milbemycin β1", Tetrahedron, 1989, pp. 7161-7194, vol. 45:22.
Liu et al., "Divergent Asymmetric Total Synthesis of Mulinane Diterpenoids", Angew. Chem. Int. Ed., 2017, pp. 12708-12711, vol. 56.
Liu et al., "Regioselective Iridium-Catalyzed Asymmetric Monohydrogenation of 1,4-Dienes", J. Am. Chem. Soc., 2017, pp. 14470-14475.
Malachowski et al., "The Enantioselective Synthesis of (−)-Lycoramine with the Birch-Cope Sequence", J. Org. Chem., 2007, pp. 6792-6796, vol. 72.
Mander et al., "Synthetic Plant Growth Regulators. II. The Preparation of Tricyclic Helminthosporic Acid Analogues with Gibberellin-like Properties", Aust. J. Chem., 1974, pp. 2645-2656, vol. 27.
Mazraati Tajabadi et al., "Design and Synthesis of Natural Product Inspired Libraries Based on the Three-Dimensional (3D) Cedrane Scaffold: Toward the Exploration of 3D Biological Space", J. Med. Chem., 2018, pp. 6609-6628, vol. 61.
Mejer et al., "Reduction with lithium in ethylenediamine, Part IV, Extensive reduction of polycyclic hydrocarbons to cycloolefins with double bonds at ring junction", 1979, vol. 53, issue 11, pp. 2385-2388.
Murthy et al., "Studies in Metal-Ammonia Reduction—5: Reduction and Reductive Methylation of Some Naphthoic Acids", Tetrahedron, 1982, pp. 2831-2836, vol. 38:18.
Peters et al., "Enantio- and Regioselective Ir-Catalyzed Hydrogenation of Di- and Trisubstituted Cycloalkenes", J. Am. Chem. Soc., 2016, pp. 11930-11935, vol. 138.
Peters et al., "Scalable and safe synthetic organic electroreduction inspired by Li-ion battery chemistry", Science, 2019, pp. 1-20, vol. 363:6429.
Rabideau et al., "The Birch Reduction of Aromatic Compounds", Organic Reactions, 1992, pp. 1-47, vol. 42.
Rabideau, "The Metal-Ammonia Reduction of Aromatic Compounds", Tetrahedron, 1989, pp. 1579-1603, vol. 45:6.
Rao et al., "Michael Reactions of the Anions generated by the Metal-Ammonia Reduction of Benzoic Acids", J.C.S. Chem. Comm., 1980, pp. 315-316.
Rao et al., "Synthesis Based on Cyclohexadienes. Part 8. Synthesis of 1-Methylbicyclo[2.2.2]oct-2-enecarboxylate Derivatives", J. Chem. Soc. Perkin Trans., 1993, pp. 2333-2337.
Reggel et al., "Lithium in Ethylenediamine: A New Reducing System for Organic Compounds", J. Org. Chem., 1957, pp. 891-895, vol. 22.
Rehbein et al., "Gosteli-Claisen Rearrangement: Substrate Synthesis, Simple Diastereoselectivity, and Kinetic Studies", J. Org. Chem., 2009, pp. 1531-1540, vol. 74.
Rosokha et al., "The Preorganization Step in Organic Reaction Mechanisms. Charge-Transfer Complexes as Precursors to Electrophilic Aromatic Substitutions", J. Org. Chem., 2002, pp. 1727-1737, vol. 67:6.
Rutherford et al., "Consequences of Correlated Solvation on the Structures and Reactivities of RLi-Diamine Complexes: 1,2-Addition and a-Lithiation Reactions of Imines by TMEDA-Solvated n-Butyllithium and Phenyllithium", J. Am. Chem. Soc., 2002, pp. 264-271, vol. 124:2.
Saito et al., "Synthesis and Conformational Analysis of Parent Perhydroazulenes Reveal an Energetically Preferred cis Ring Fusion", J. Org. Chem., 2020, pp. 4441-4447, vol. 85.
Schuda et al., "Use of the Ketal Claisen Rearrangement for the Synthesis of Cyclic Sesquiterpenes Containing Quaternary Centers. A Formal Synthesis of Cuparene", Tetrahedron, 1987, pp. 463-468, vol. 43:3.
Seo et al., "Direct β-Selective Hydrocarboxylation of Styrenes with $CO_2$ Enabled by Continuous Flow Photoredox Catalysis", J. Am. Chem. Soc., 2017, pp. 13969-13972, vol. 139.
Shabangi et al., "Electrochemical Investigation of the Reducing Power of $SmI_2$ in THF and the Effect of HMPA Cosolvent", Tetrahedron Letters, 1997, pp. 1137-1140, vol. 38: 7.
Shapiro et al., "Muscarinic Activity of the Thiolactone, Lactam, Lactol, and Thiolactol Analogues of Pilocarpine and a Hypothetical Model for the Binding of Agonists to the m1 Receptor", J. Med. Chem., 1992, pp. 15-27, vol. 35.
Shindo et al., "Scope and Limitations of Lithium-Ethylenediamine-THF-Mediated Cleavage at the α-Position of Aromatics: Deprotection of Aryl Methyl Ethers and Benzyl Ethers under Mild Conditions", Synthesis, 2004, pp. 692-700, No. 5.
Singh et al., "Total Synthesis of (±)-Atractyligenin", J. Am. Chem. Soc., 1987, pp. 6187-6189, vol. 109:20.
Szwarc, "Ions and Ion Pairs", Acc. Chem. Res., 1969, pp. 87-96, vol. 2.
Tietze et al., "Reactions and Syntheses in the Organic Chemistry Laboratory", 2014, pp. 1-1099, Wiley-VCH, Weinheim, Germany.
Tiwari et al., "Rapid Enantioselective and Diastereoconvergent Hybrid Organic/Biocatalytic Entry into the Oseltamivir Core", J. Org. Chem., 2021, pp. 6494-6503, vol. 86.
Wooster et al., "Mechanism of the Reduction of Unsaturated Compounds with Alkali Metals and Water", J. Am. Chem. Soc., 1937, pp. 596-597, vol. 59.
Wu et al., "Synthetic Studies on Enantioselective Total Synthesis of Cyathane Diterpenoids: Cyrneines A and B, Glaucopine C, and (+)-Allocyathin B2", J. Org. Chem., 2019, pp. 3223-3238, vol. 84.
Yoshimi et al., "Hydroxide ion as electron source for photochemical Birch-type reduction and photodehalogenation", Tetrahedron Lett., 2008, pp. 3400-3404, vol. 49.
Zhang et al., "Synthesis of α,β-unsaturated carbonyl compounds via a visible-light-promoted organocatalytic aerobic oxidation", Chem. Commun., 2013, pp. 11662-11664, vol. 49.
Zhang et al., "Total Synthesis of the Diterpenoid (+)-Harringtonolide", Angew. Chem. Int. Ed., 2016, pp. 11638-11641, vol. 55.
Zhao et al., "Chlorotrimethylsilane and Sodium Iodide: A Remarkable Metal-Free Association for the Desulfurization of Benzylic Dithioketals under Mild Conditions", Adv. Synth. Catal., 2019, pp. 1-13.
Zhu et al., "Negative Kinetic Temperature Effect on the Hydride Transfer from NADH Analogue BNAH to the Radical Cation of N-Benzylphenothiazine in Acetonitrile", J. Org. Chem., 2006, pp. 7007-7015, vol. 71.
Zhu et al., "Total Syntheses of Herqulines B and C", J. Am. Chem. Soc., 2019, pp. 3409-3413, vol. 141.
Zimmerman, "A Mechanistic Analysis of the Birch Reduction", Accounts of Chemical Research, 2012, pp. 164-170, vol. 45:2.
Zong et al., "Enantioselective Total Syntheses of Manginoids A and C and Guignardones A and C", Angew. Chem. Int. Ed., 2021, pp. 15286-15290, vol. 60.
Altundas et al., "Excellent and Convenient Procedures for Reduction of Benzene and Its Derivatives", Turk. J. Chem., 2005, pp. 513-518, vol. 29.
Ankner et al., "$SmI_2$/$H_2O$/amine promoted reductive cleavage of benzyl-heteroatom bonds: optimization and mechanism", Tetrahedron, 2009, pp. 10856-10862, vol. 65.
Archer et al., "Cannabinoids. 3. Synthetic Approaches to 9-Ketocannabinoids. Total Synthesis of Nabilone", J. Org. Chem., 1977, pp. 2277-2284, vol. 42:13.
Ashtekar et al., "Nucleophile-Assisted Alkene Activation: Olefins Alone Are Often Incompetent", J. Am. Chem. Soc., 2016, pp. 8114-8119, vol. 138:26.
Aycock, "Solvent Applications of 2-Methyltetrahydrofuran in Organometallic and Biphasic Reactions", Organic Process Research & Development, 2007, pp. 156-159, vol. 11:1.

(56) References Cited

OTHER PUBLICATIONS

Baar et al., "Stereoselectivity in Organometallic Reactions: Intramolecular Oxidative Addition of Aryl-Halogen Bonds to Platinum(II)", Organometallics, 1998, pp. 32-40, vol. 17.
Bayindir et al., "A facile one-pot method to synthesise 2-alkylated indole and 2,2'-bis(indolyl)methane derivatives using ketones as electrophiles and their anion sensing ability", RSC Adv., 2016, pp. 72959-72967, vol. 6.
Bedenbaugh et al., "Synthesis of Aldehydes and Secondary Amines from Carboxylic Acids via Imines", Journal of the American Chemical Society, 1970, pp. 5774-5775, vol. 92:19.
Beesley et al., "The Formation and Stability of spiro-Compounds. Part 1. spiro-Compounds from cyclo-Hexane.", J. Chem. Soc., 1915, pp. 1080-1106, vol. 107.
Benkeser, "Reduction of organic compounds by lithium in amines of low molecular weight", Advances in Chemistry, ACS, Metal-Organic Compounds, 1959, pp. 58-62.
Benkeser et al., "A new reducing system: Calcium metal in amines effect of hexamethylphosphoramide on calcium reductions", J. Org. Chem., 1979, vol. 44, No. 21, pp. 3737-3739.
Benkeser et al., "A Safe and Convenient New Procedure for Reducing Aromatic Compounds To Birch-Type Products", Tetrahedron Letters, 1984, pp. 2089-2092, vol. 25:20.
Benkeser et al., "Highly Selective Lithium-Amine Reducing Systems. The Selective Reduction of Aromatic Compounds by Lithium in Mixed Amine Solvents", J. Org. Chem., 1964, pp. 1313-1316, vol. 29.
Benkeser et al., "Reduction of Organic Compounds by Lithium in Low Molecular Weight Amines. Highly Selective Lithium-Amine Reducing Systems", Tetrahedron Letters, 1960, pp. 1-3, No. 16.
Benkeser et al., "Reduction of Organic Compounds by Lithium in Low Molecular Weight Amines. I. Selective Reduction of Aromatic Hydrocarbons to Monoolefins", J. Am. Chem. Soc., 1955, pp. 3230-3233, vol. 77.
Benkeser et al., "Reduction of Organic Compounds by Lithium in Low Molecular Weight Amines. III. Reduction of Aromatic Compounds Containing Functional Groups," J. Am. Chem. Soc., 1955, pp. 6042-6045, vol. 77.
Benkeser et al., "Reduction of Organic Compounds by Lithium in Low Molecular Weight Amines. IV. The Effect of Nitro and Amino Groups on the Course of the Reduction", J. Am. Chem. Soc., 1958, pp. 6573-6577, vol. 80.
Benkeser et al., "Reduction of Organic Compounds by Lithium in Low Molecular Weight Amines. VII. The Preparation of Dihydroaromatics. A Comparison of the Lithium-Amine and Birch Reduction Systems", J. Org. Chem., 1963, pp. 1094-1097, vol. 28.
Benkeser et al., "Selective Reductions of Aromatic Systems To Monoolefins", J. Am. Chem. Soc., 1954, pp. 631-632.
Biffin et al., "A Re-Examination of the Sodium and Liquid Ammonia Reduction Of m-Methoxybenzoic Acid", Aust. J. Chem., 1972, pp. 1329-1334, vol. 25.
Birch, "The Birch reduction in organic synthesis", Pure & Appl. Chem., 1996, pp. 553-556, vol. 68:3.
Birch, "Reduction by Dissolving Metals. Part I.", J. Chem. Soc., 1944, pp. 430-436.
Birch, "Reduction by Dissolving Metals. Part II.", J. Chem. Soc., 1945, pp. 809-813.
Birch, "Reduction by Dissolving Metals. Part III.", J. Chem. Soc., 1946, pp. 593-597.
Birch et al., "A Theoretical Approach to the Birch Reduction. Structures and Stabilities of Cyclohexadienyl Radicals", Journal of the American Chemical Society, 1980, pp. 4074-4080, vol. 102:12.
Birch et al., "A Theoretical Approach to the Birch Reduction. Structures and Stabilities of the Radical Anions of Substituted Benzenes", Journal of the American Chemical Society, 1980, pp. 3370-3376, vol. 102:10.
Birch, "2-Cyclohexenones from 2-methylpyridines", J. Chem. Soc., 1947, pp. 1270.
Brezina et al., "The benzene radical anion in the context of the Birch reduction: when solvation is the key", J. Phys. Chem. Lett., 2020, pp. 6032-6038.
Bykova et al., "Multicomponent reactions of methyl substituted all-cis tetrafluorocyclohexane aldehydes", Org. Biomol. Chem., 2016, pp. 1117-1123, vol. 14.
Chapuis et al., "A Concise Synthesis of rac-Ambrox® via the Palladium(0)-Catalyzed Carboalkoxylation of an Allylic Ammonium Salt, as Compared to a Formaldehyde Hetero Diels-Alder Approach", Helv. Chim. Acta, 2019, pp. 1-22, vol. 102.
Cole et al., "Organocatalyzed Birch Reduction Driven by Visible Light", J. Am. Chem. Soc., 2020, pp. 13573-13581, vol. 142:31.
Corey et al., "Total Synthesis of (±)-Antheridium-Inducing Factor (AAn, 2) of the Fern Anemia phyllitidis. Clarification of Stereochemistry", J. Am. Chem. Soc., 1985, pp. 5574-5576, vol. 107.
Costanzo et al., "Ammonia-free Birch reductions with sodium stabilized in silica gel, Na—SG(I)", Tetrahedron Letters, 2009, pp. 5463-5466, vol. 50.
Danishefsky et al., "The Pyridine Route to a-Substituted Cyclohexenones", J. Org. Chem., 1975, pp. 3606-3608, vol. 40:24.
Donohoe et al., "Ammonia Free Partial Reduction of Aromatic Compounds Using Lithium Di-tert-butylbiphenyl (LiDBB)", J. Org. Chem., 2002, pp. 5015-5018, vol. 67.
Donohoe et al., "The partial reduction of electron-deficient pyrroles: procedures describing both Birch (Li/NH3) and ammonia-free (Li/DBB) conditions", Nature Protocols, 2007, pp. 1888-1895, vol. 2:8.
Formenti et al., "A State-of-the-Art Heterogeneous Catalyst for Efficient and General Nitrile Hydrogenation", Chem. Eur. J., 2020, pp. 15589-15595, vol. 26.
Garst et al., "Reductions with Lithium in Low Molecular Weight Amines and Ethylenediamine", J. Org. Chem., 2000, pp. 7098-7104, vol. 65.
Gaston et al., "The Detosylation of Chiral 1,2-Bis(tosylamides)", J. Org. Chem., 2021, pp. 9163-9180, vol. 86.
Golec et al., "BIMP-Catalyzed 1,3-Prototropic Shift for the Highly Enantioselective Synthesis of Conjugated Cyclohexenones", Angew. Chem. Int. Ed., 2020, pp. 17417-17422, vol. 59.
Greenfield et al., "Kinetics of the Birch Reduction", Ber. Bunsenges. Phys. Chem., 1998, pp. 1808-1814, vol. 102:12.
Harvey, "Metal-Ammonia Reduction of Aromatic Molecules", Synthesis: International Journal of Methods in Synthetic Organic Chemistry, 1970, pp. 161-172, No. 4.
Hayashi, "Time Economy in Total Synthesis", J. Org. Chem., 2021, pp. 1-23, vol. 86.
Hiraoka et al., "Screening, substrate specificity and stereoselectivity of yeast strains, which reduce sterically hindered isopropyl ketones", Tetrahedron: Asymmetry , 2006, pp. 3358-3367. vol. 17.
Huang et al., "Aluminum Complexes Containing Cyclohexane-1,2-diyl Linked Bis(ketiminato) Ligands and Proton-Promoted Demethylation", Eur. J. Inorg. Chem., 2008, pp. 3000-3008.
Huang et al., "Scalable procedure for the fragmentation of hydroperoxides mediated by copper and iron tetrafluoroborate salts", Org. Biomol. Chem., 2016, pp. 1-8, vol. 14:26.
Huck et al., "Shaping Molecular Landscapes: Recent Advances, Opportunities, and Challenges in Dearomatization", Chem, 2020, pp. 1589-1603, vol. 6.
Hugelshofer et al., "Calyciphylline B-type Alkaloids: Evolution of a Synthetic Strategy to (−)-Daphlongamine H", J. Org. Chem., 2019, pp. 14069-14091, vol. 84.
Iio et al., "Total Synthesis of Vernolepin—I: Synthesis of the Key Intermediate", Tetrahedron, 1979, pp. 941-948, vol. 35:8.
Joshi et al., "Experiences with Commercial Production Scale Operation of Dissolving Metal Reduction Using Lithium Metal and Liquid Ammonia", Organic Process Research & Development, 2005, pp. 997-1002, vol. 9:6.

\* cited by examiner

NON-CRYOGENIC, AMMONIA-FREE REDUCTION OF ARYL COMPOUNDS

CROSS REFERENCE TO RELATED APPLICATION

This application is a divisional application of U.S. patent application Ser. No. 17/477,900, filed Sep. 17, 2021, and claims priority to U.S. Provisional Application No. 63/080,205, filed Sep. 18, 2020, the disclosures of which are hereby incorporated by reference in their entireties.

STATEMENT REGARDING FEDERAL FUNDING

This invention was made with government support under Grant No. 1506942 awarded by the National Science Foundation. The government has certain rights in the invention.

The present disclosure is, in general, directed to methods of reducing an aromatic ring or a cyclic, allylic ether in a compound.

Dearomatization is an important platform in chemistry and drug development. The Birch reduction uniquely dearomatizes arenes into 1,4-cyclohexadienes. (See, e.g., Birch, A. J. The Birch reduction in organic synthesis. *Pure Appl. Chem.*, 1996, 68, 553-556). In many cases, all the carbons of Birch reduction products could be differentially derivatized, providing useful building blocks for complex molecule synthesis. Despite substantial efforts devoted to avoiding ammonia and cryogenic conditions, the traditional, cumbersome, and dangerous procedure remains the standard.

The setup requires an alkali metal (either lithium, sodium, or potassium), liquid ammonia (boiling point: −33° C.), and cryogenic temperature (≤−33° C.), e.g.,

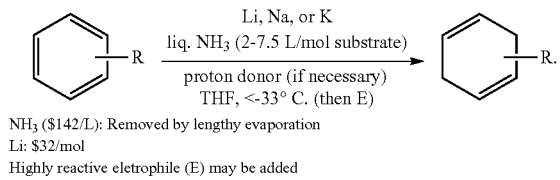

NH₃ ($142/L): Removed by lengthy evaporation
Li: $32/mol
Highly reactive eletrophile (E) may be added One of the most tedious steps in setting up a Birch reduction is to accumulate liquid ammonia from gaseous ammonia, which can take hours to days. The dissipation of ammonia after the reaction is complete can also take hours. These logistical challenges make it difficult to perform multiple Birch reductions in parallel.

To overcome these challenges, researchers have developed ammonia-free conditions. For example, some have used neat ethylamine or ethylenediamine and lithium, e.g.,

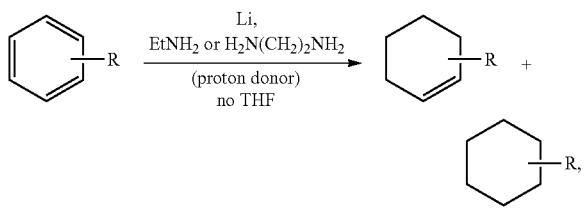

providing a mixture of over-reduced products (See, e.g., Benkeser R. A. et al. Reduction of organic compounds by lithium in low molecular weight amines. III. Reduction of aromatic compounds containing functional groups. *J. Am. Chem. Soc.*, 1955, 77, 6042-6045 and Benkeser R. A. et al. Reduction of organic compounds by lithium in low molecular weight amines. I. Selective reduction of aromatic hydrocarbons to monoolefins. *J. Am. Chem. Soc.*, 1955, 77, 3230-3233).

Some have reported the reduction of electron-deficient arenes and heterocycles using di-tert-butylbiphenyl ($1000/mol) and lithium at −78° C., e.g.,

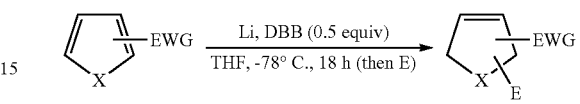

(See, e.g., Donohue T. J. et al. Ammonia free partial reduction of aromatic compounds using lithium di-tert-butylbiphenyl (LiDBB), *J. Org. Chem.*, 2002, 67, 5015-5018). This method was highly oxygen-sensitive and as lengthy as the standard Birch procedure (See, e.g., Donohue, T. J. et al., The partial reduction of electron-deficient pyrroles: procedures describing both Birch (Li/NH₃) and ammonia-free (Li/DBB) conditions. *Nat. Protoc.*, 2007, 2, 1888-1895).

Others have developed a novel protocol for the Birch reduction which requires 3-9 equivalents of 15-crown-5 ($1579/mol) and is limited to electron-rich or neutral substrates, e.g.,

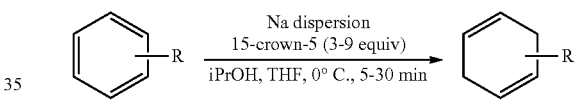

(See, e.g., Lei, P. et al. A practical and chemoselective ammonia-free Birch reduction. *Org. Lett.*, 2018, 20 3439-3442).

Some have described an electrochemical reduction of electron-rich arenes, which required 3.5-10 equivalents of tri(pyrrolidin-1-yl)phosphine oxide ($5,040/mol) and 3.0 equivalents of 1,3-dimethylurea ($5.16/mol), e.g.,

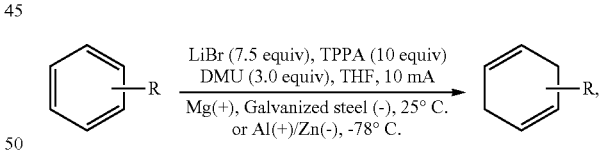

both of which must be removed from the product by column chromatography. Their 0.45-mole scale reaction took 3 days in a flow reactor. Others used a vicinal diamine and lithium at −10° C. to transform anisoles into phenols rather than 1,4-cyclohexadienes (See, e.g., Shindo, T. et al. Scope and limitations of lithium-ethylenediamine-THF-mediated cleavage at the α-position of aromatics: Deprotection of aryl methyl ethers and benzyl ethers under mild conditions. *Synthesis*, 2004, 692-700). Finally, others treated arenes with lithium and ethylenediamine in THF or diethyl ether but did not isolate 1,4-cyclohexadiene products and indicated that THF might be a ligand for a lithium ion (see, e.g., Shindo, T. et al. Scope and limitations of lithium-ethylenediamine-THF-mediated cleavage at the α-position of aromatics: Deprotection of aryl methyl ethers and benzyl ethers under mild conditions. *Synthesis*, 2004, 692-700 and Hiraoka, C. et al. Screening, substrate specificity and stereoselectivity of yeast strains, which reduce sterically hindered isopropyl ketones. *Tetrahedron: Asymmetry,* 2006, 17, 3358-3367).

It is noted that, as used in the preceding descriptions, DBB is 4,4'-di-tert-butylbiphenyl; TPPA is tri(pyrrolidin-1-yl) phosphine oxide; and DMU is 1,3-dimethylurea.

Despite these efforts, the original, cumbersome and dangerous Birch protocol remains the current standard. Due to the inconvenient procedure, Birch reductions are often avoided in favor of more familiar, often less satisfactory, techniques (See, e.g., Huang, D. et al. Scalable procedure for the fragmentation of hydroperoxides mediated by copper and iron tetrafluoroborate salts. *Org. Biomol. Chem.,* 2016, 14, 6197-6200 and Harvey, R. G. Metal-ammonia reduction of aromatic molecules. *Synthesis,* 1970, 1970, 161-172). Therefore, there remains a need for a Birch-type reduction that is fast and effective for both electron-rich and deficient arenes without ammonia, specialized equipment, or expensive additives.

SUMMARY

A method of reducing an aromatic ring or a cyclic, allylic ether in a compound is provided. The method comprises:
  preparing a reaction mixture comprising a compound comprising an aromatic moiety or a cyclic, allylic ether moiety, an alkali metal, and either ethylenediamine, diethylenetriamine, triethylenetetramine, or a combination thereof, in an ether solvent; and
  reacting the reaction mixture at from −20° C. to 30° C. for a time sufficient to reduce a double bond in the aromatic moiety to a single bond or to reduce the cyclic, allylic ether moiety.

Also provided herein is a method of reducing an aromatic ring or a cyclic, allylic ether in a compound, comprising:
  preparing a reaction mixture comprising a compound comprising an aromatic moiety or a cyclic, allylic ether moiety, an alkali metal, an alcohol, and either ethylenediamine, diethylenetriamine or a combination thereof, in an ether solvent; and
  reacting the reaction mixture at from −20° C. to 30° C. for a time sufficient to reduce a double bond in the aromatic moiety to a single bond or to reduce the cyclic, allylic ether moiety.

The following numbered clauses provide various aspects or embodiments of the present invention.

Clause 1. A method of reducing an aromatic ring or a cyclic, allylic ether in a compound, comprising:
  preparing a reaction mixture comprising a compound comprising an aromatic moiety or a cyclic, allylic ether moiety, an alkali metal, and either ethylenediamine or diethylenetriamine, in an ether solvent; and
  reacting the reaction mixture at from −20° C. to 30° C. for a time sufficient to reduce a double bond in the aromatic moiety to a single bond or to reduce the cyclic, allylic ether moiety.

Clause 2. The method of clause 1, wherein the aromatic moiety is substituted with a $C_1$-$C_6$ carboxylic acid, such as carboxyl (e.g. benzoic acid), carboxymethy, carboxyethyl, carboxypropyl, carboxybutyl, carboxypentyl, or carboxyhexyl, including structural isomers thereof.

Clause 3. A method of reducing an aromatic ring or a cyclic, allylic ether in a compound, comprising:
  preparing a reaction mixture comprising a compound comprising an aromatic moiety or a cyclic, allylic ether moiety, an alkali metal, an alcohol, and either ethylenediamine or diethylenetriamine, in an ether solvent; and
  reacting the reaction mixture at from −20° C. to 30° C. for a time sufficient to reduce a double bond in the aromatic moiety to a single bond or to reduce the cyclic, allylic ether moiety.

Clause 4. The method of clause 3, wherein the compound comprising an aromatic moiety is n-butyl phenyl ether.

Clause 5. The method of clause 3, wherein the alcohol is a $C_2$-$C_6$ alkyl alcohol (e.g. alkanol), such as ethanol, a propanol, a butanol, a pentanol, or a hexanol.

Clause 6. The method of any one of clause 4 or 5, wherein the alcohol is a secondary or tertiary alcohol.

Clause 7. The method of any one of clauses 1-6, wherein the alkali metal is Li.

Clause 8. The method of any one of clauses 1-7, wherein the aromatic moiety is a phenyl moiety or a fused benzene ring of a polycyclic aromatic moiety.

Clause 9. The method of any one of clauses 1-7, wherein the aromatic moiety is $C_6$-aryl or substituted $C_6$-aryl.

Clause 10. The method of any one of clauses 1-9, wherein the aromatic moiety is substituted with a $C_1$-$C_6$ carboxylic acid, such as carboxyl (e.g. benzoic acid), carboxymethy, carboxyethyl, carboxypropyl, carboxybutyl, carboxypentyl, or carboxyhexyl, including structural isomers thereof.

Clause 11. The method of any one of clauses 1-9, wherein the aromatic moiety is substituted with a $C_1$-$C_6$ alkoxyl group, such as methoxyl, propoxyl, butoxyl, pentyloxy, or hexyloxy, including structural isomers thereof.

Clause 12. The method of any one of clauses 1-9, wherein the aromatic moiety is a carbonyl-substituted $C_1$-$C_6$ alkyl group (e.g., $C_1$-$C_6$ alkyl ketones or aldehydes), including structural isomers thereof.

Clause 13. The method of any one of clauses 1-12, wherein the reaction is performed for a length of time sufficient to yield at least 50% yield of the product of the conversion of the double bond in the aromatic moiety to a single bond.

Clause 14. The method of clause 1, wherein the compound is benzoic acid, a benzylic alcohol, or a free amine.

Clause 15. The method of any one of clauses 1-14, wherein the ether solvent is a saturated cyclic ether, such as tetrahydrofuran or a derivative thereof, or 1,4, dioxane, or a derivative thereof, where the derivative optionally can be alkyl-substituted or halo-substituted.

Clause 16. The method of any one of clauses 1-15, wherein the ethylenediamine:compound molar ratio or the diethylenetriamine: compound molar ratio in the reaction mixture ranges from 2-20:1.

Clause 17. The method of any one of clauses 1-16, wherein the alkaline metal:compound molar ratio in the reaction mixture ranges from 2-10:1.

Clause 18. The method of any one of clauses 1-16, wherein the ethylenediamine: alkaline metal molar ratio, such as the ethylenediamine:Li molar ratio, or the diethylenetriamine:alkaline metal molar ratio, such as the diethylenetriamine:Li molar ratio is approximately or about 2:1.

Clause 19. The method of any one of clauses 1-18, wherein the reaction mixture is reacted at a temperature ranging from −20° C. to 30° C.

Clause 20. The method of any one of clauses 1-18, wherein the reaction mixture is reacted at a temperature ranging from approximately 0° C. to 10° C.

Clause 21. The method of any one of clauses 1-18, wherein the reaction mixture is reacted at approximately 0° C.

Clause 22. The method of any one of clauses 1-21, wherein the compound comprises an aromatic moiety.

Clause 23. The method of any one of clauses 1-22, wherein the compound comprises a cyclic, allylic ether moiety.

DETAILED DESCRIPTION

Figure 1:
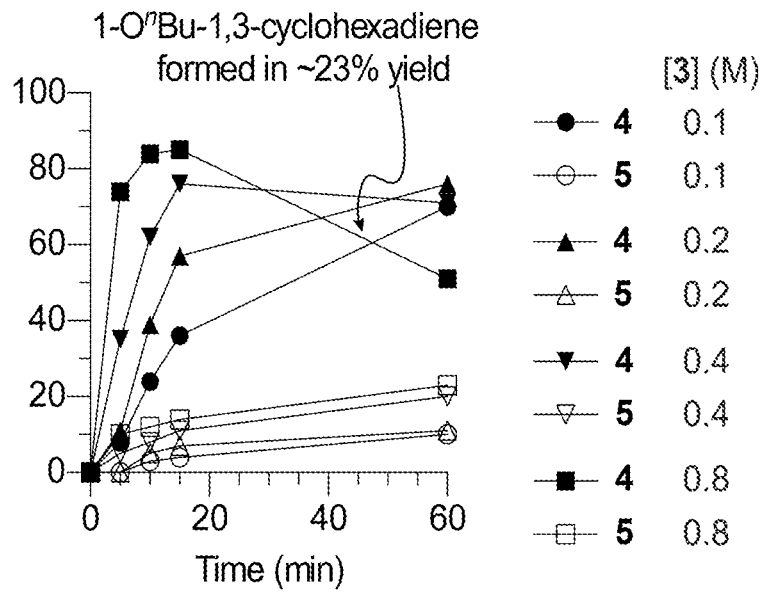
FIG. 1 is a graph depicting the % yield diene 4 and over-reduced product 5 at different stirring times for different starting concentrations of n-butyl phenyl ether 3.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of" limits the scope of a claim to the specified materials or steps and those that do not materially affect basic and novel characteristic(s). The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps.

The methods described herein can be used for the reduction of an aromatic moiety, e.g., aromatic rings, or an allylic ether moiety to produce, e.g., unconjugated dihydro derivatives. The reaction may be conducted in an ether solvent at a temperature in the range of from −20° C. to 30° C., for example from −20° C. to 30° C., such as from 0° C. to 10° C. The reaction may be conducted for a length of time to reduce a double bond in a reaction mixture comprising a compound (substrate) comprising an aromatic moiety or a cyclic, allylic ether moiety. The reaction is typically conducted for a length of time to convert the aromatic moiety or the cyclic, allylic ether moiety with at least at least 50%, at least 60%, at least 70%, at least 80%, at least 90%, or at least 99% molar conversion rate, including any increment therebetween, for reducing a double bond of the compound comprising an aromatic moiety or a cyclic, allylic ether moiety. The length of time for the reaction may be at least 1 minute, at least 5 minutes, at least 15 minutes, at least 30 minutes, at least 45 minutes, or at least 60 minutes, or longer, such as for 15, 30, 45, 60, 90, or 120 minutes.

The reaction may be performed in the presence of an alkali metal, such as Li, K, or Na, in the presence of ethylenediamine. The substrate can be any substrate comprising an aromatic group suitable for reduction by Birch reduction or a cyclic, allylic ether. The aromatic group or the cyclic, allylic ether group may be substituted. By "substituted" it is meant that one or more hydrogen atoms of the aromatic group is substituted with another group ("substituents"), such as an alkyl, alkoxyl (ether), carbonyl, carboxyl, nitrate, sulfate, or other groups. While carboxyl-containing substituents may react robustly without the presence of an alcohol in the reaction mixture, certain groups may require the presence of an alcohol, such as a secondary or tertiary alcohol, for the reaction to proceed in a reasonable pace. For example, as shown below, reduction of benzoic acid (carboxyl-substituted) did not require an alcohol to be present for the reaction to proceed in a suitably robust manner, while reduction of reduction of n-butyl phenyl ether (butoxyl substituted), having an alkoxyl (ether) substitution, required an alcohol for the reaction to proceed with good yield, and with secondary or tertiary alcohols, such as isopropyl alcohol, t-butyl alcohol, and t-amyl alcohol, providing greater yields. The substrate may be a benzylic alcohol. A "benzylic alcohol" refers to an aromatic compound that comprises a pendant alcohol (—OH) group. The substrate may be a free amine. A "free amine" refers to a compound that comprises an amine functional group that is not protonated.

An aromatic (aryl) compound comprises an aromatic ring meeting the requirements of Hiickel's rule, having $4n+2\pi$ electrons in a conjugated system of p orbitals, where n is an integer. The quintessential aromatic compound being benzene. "Aryl," alone or in combination refers to an aromatic ring system such as phenyl or naphthyl. Multi-ring structures can be aromatic, such as anthracene, phenanthrene, or pyrene, as well as heterocyclic aromatic compounds, comprising one or more hetero-atoms, such as N, O, or S in place of a ring carbon, such as pyridine, pyrrole, furan, and thiophene. "Aryl" also can include aromatic ring systems that are optionally fused with a cycloalkyl ring. A "substituted aryl" is an aryl that is independently substituted with one or more substituents attached at any available atom to produce a stable compound, wherein the substituents can be as described herein. The substituents can be, for example and without limitation, hydrocarbyl groups, alkyl groups, alkoxy groups, carboxyl-containing groups, ethers, and nitrate-containing groups. "Optionally substituted aryl" refers to aryl or substituted aryl. An aryloxy group can be, for example, an oxygen atom substituted with any aryl group, such as phenoxy. An arylalkoxy group can be, for example, an oxygen atom substituted with any aralkyl group, such as benzyloxy. "Arylene" denotes divalent aryl, and "substituted arylene" refers to divalent substituted aryl. "Optionally substituted arylene" refers to arylene or substituted arylene. A "polycyclic aryl group" and related terms, such as "polycyclic aromatic group" refers to a group composed of at least two fused aromatic rings. "Heteroaryl" or "hetero-substituted aryl" refers to an aryl group substituted with one or more heteroatoms, such as N, O, P, and/or S.

As used herein, "alkyl" refers to straight, branched chain, or cyclic hydrocarbon groups including, for example, from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. An alkyl group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of straight alkyl groups include methyl, ethyl, propyl, butyl, pentyl, hexyl, heptyl, octyl, nonyl, and decyl. Branched alkyl groups comprises any straight alkyl group substituted with any number of alkyl groups. Non-limiting examples of branched alkyl groups include isopropyl, isobutyl, sec-butyl, and t-butyl. Non-limiting examples of cyclic alkyl groups include cyclopropyl, cyclobutyl, cyclopentyl, cyclohexyl, cycloheptlyl, and cyclooctyl groups. Cyclic alkyl groups also comprise fused-, bridged-, and spiro-bicycles and higher fused-, bridged-, and spiro-systems. A "fused-" cyclic alkyl group refers to at least two cyclic groups that share two carbon atoms which are directly bonded with each other. A "spiro-" cyclic alky group refers to at least two cyclic groups that share one carbon atom. A "bridged-" cyclic alkyl group refers to at least two cyclic groups that share two carbon atoms which are connected by at least one additional carbon atom, forming a "bridge". A cyclic alkyl group can be substituted with any number of straight, branched, or cyclic alkyl groups. "Substituted alkyl" can include alkyl substituted at 1 or more (e.g., 1, 2, 3, 4, 5, or even 6) positions, which substituents are attached at any available atom to produce a stable compound, with substitution as described herein. "Optionally substituted alkyl" refers to alkyl or substituted alkyl. "Alkylene" and "substituted alkylene" can include divalent alkyl and divalent substituted alkyl, respectively, including, without limitation, methylene, ethylene, trimethylene, tetramethylene, pentamethylene, hexamethylene, hepamethylene, octamethylene, nona methylene, or decamethylene. "Optionally substituted alkylene" can include alkylene or substituted alkylene.

"Alkene or alkenyl" can include straight, branched chain, or cyclic hydrocarbyl groups including, e.g., from 2 to about 20 carbon atoms, such as, without limitation $C_{2-3}$, $C_{2-6}$, $C_{2-10}$ groups having one or more, e.g., 1, 2, 3, 4, or 5, carbon-to-carbon double bonds. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. "Substituted alkene" can include alkene substituted at 1 or more, e.g., 1, 2, 3, 4, or 5 positions, which substituents are attached at any available atom to produce a stable compound, with substitution as described herein. "Optionally substituted alkene" can include alkene or substituted alkene. Likewise, "alkenylene" can refer to divalent alkene. Examples of alkenylene include without limitation, ethenylene (—CH=CH—) and all stereoisomeric and conformational isomeric forms thereof. "Substituted alkenylene" can refer to divalent substituted alkene. "Optionally substituted alkenylene" can refer to alkenylene or substituted alkenylene.

The term "alkoxy" can refer to an —O-alkyl group having the indicated number of carbon atoms. An ether or an ether group comprises an alkoxy group. For example, a ($C_1$-$C_6$) alkoxy group includes —O-methyl (methoxy), —O-ethyl (ethoxy), —O-propyl (propoxy), —O-isopropyl (isopropoxy), —O-butyl (butoxy), —O-sec-butyl (sec-butoxy), —O-tert-butyl (tert-butoxy), —O-pentyl (pentoxy), —O-isopentyl (isopentoxy), —O-neopentyl (neopentoxy), —O-hexyl (hexyloxy), —O-isohexyl (isohexyloxy), and —O-neohexyl (neohexyloxy). "Hydroxyalkyl" refers to a ($C_1$-$C_{10}$)alkyl group wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof. The term "ether" or "oxygen ether" refers to an alkyl group wherein one or more of the alkyl group's carbon atoms is replaced with an —O— group. The term ether can include —CH$_2$—(OCH$_2$—CH$_2$)$_q$OP$_1$ compounds where P$_1$ is a protecting group, —H, or a ($C_1$-$C_{10}$)alkyl. Exemplary ethers include polyethylene glycol, diethylether, methylhexyl ether and the like.

"Carboxyl" or "carboxylic" refers to group having an indicated number of carbon atoms, where indicated, and terminating in a —C(O)OH group, thus having the structure —R—C(O)OH, where R is an unsubstituted or substituted divalent organic group that can include linear, branched, or cyclic hydrocarbons. Non-limiting examples of these include: $C_{1-8}$ carboxylic groups, such as ethanoic, propanoic, 2-methylpropanoic, butanoic, 2,2-dimethylpropanoic, pentanoic, etc. "Amine" or "amino" refers to group having the indicated number of carbon atoms, where indicated, and terminating in a —NH$_2$ group, thus having the structure —R—NH$_2$, where R is a unsubstituted or substituted divalent organic group that, e.g. includes linear, branched, or cyclic hydrocarbons, and optionally comprises one or more heteroatoms. The term "alkylamino" refers to a radical of the formula —NHRx or —NRxRx where each Rx is, independently, an alkyl radical as defined above.

An alcohol is an organic compound that carries at least one hydroxyl functional group (—OH) bound to a saturated carbon atom. Compounds with more than one hydroxyl functional group may be referred to as polyols. An alcohol may be classified by the number of carbons attached to the carbon to which the hydroxyl group is connected. In a primary alcohol, carbon atom that carries the —OH group is only attached to one alkyl group. In a secondary (2°, sec-, or s-) alcohol, the carbon atom with the —OH group attached is joined directly to two alkyl groups, which may be the same or different. In a tertiary (3°, tert-, or t-) alcohol, the carbon atom holding the —OH group is attached directly to three alkyl groups, which may be the same or different in any combination. Examples of primary alcohols include, without limitation, n-propyl alcohol, ethanol, and 2-methylpropan-1-ol. Examples of secondary alcohols include, without limitation, isopropyl alcohol, butan-2-ol, pent-3-ol, and cyclohexanol. Examples of tertiary alcohols include, without limitation, t-butyl alcohol and t-amyl alcohol.

Terms combining the foregoing refer to any suitable combination of the foregoing, such as arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl. As an example, "arylalkylene" refers to a divalent alkylene wherein one or more hydrogen atoms in an alkylene group is replaced by an aryl group, such as a ($C_3$-$C_8$)aryl group. Examples of ($C_3$-$C_8$)aryl-($C_1$-$C_6$)alkylene groups may include without limitation 1-phenylbutylene, phenyl-2-butylene, 1-phenyl-2-methylpropylene, phenylmethylene, phenylpropylene, and naphthylethylene. The term "($C_3$-$C_8$)cycloalkyl-($C_1$-$C_6$)alkylene" refers to a divalent alkylene wherein one or more hydrogen atoms in the $C_1$-$C_6$ alkylene group is replaced by a ($C_3$-$C_8$)cycloalkyl group. Examples of ($C_3$-$C_8$)cycloalkyl-($C_1$-$C_6$)alkylene groups may include without limitation 1-cyproylbutylene, cyproyl-2-butylene, cyclopentyl-1-phenyl-2-methylpropylene, cyclobutylmethylene and cyclohexylpropylene.

"Carbonyl" refers to the —C(O)— moiety within a substituent, such as a alkyl substituent on an aromatic ring, thereby forming a ketone or aldehyde substituent.

"Heteroatom" refers to any atom other than carbon or hydrogen, for example, N, O, P and S. Compounds that contain N or S atoms may be oxidized to the corresponding N-oxide, sulfoxide or sulfone compounds. "Hetero-substituted" refers to an organic compound in any embodiment described herein in which one or more carbon atoms are substituted with any atom other than carbon or hydrogen, for example, N, O, P or S.

A cyclic, allylic ether group or moiety is an optionally substituted alkyl ring that is hetero-substituted with an oxygen, and including a single carbon-to-carbon double bond (allylic moiety) in the ring. Non-limiting examples of such cyclic, allylic ether group or moiety include dihydro pyranly or dihydrofuranyl groups or moieties.

The reaction described herein may be conducted in any suitable solvent that permits the reaction to proceed. The solvent may be a saturated ether solvent which is a hetero-substituted alkane, comprising one or more oxygen hetero atoms. Non-limiting examples of saturated ether compounds include dialkyl ethers, such as, without limitation, dimethyl ether, diethyl ether, diisopropyl ether, dibutyl ether, etc., and cyclical oxygen hetero-substituted alkanes, such as tetrahydrofuran and 1,4-dioxane. The saturated ether solvent may be substituted, such as with alkyl groups.

The reactions described herein may include an alkali metal. Alkali metals may include Li, K, or Na. For example, the reactions described herein may include an alkali metal including Li.

EXAMPLES

A Birch reduction promoted by polyamines and lithium in tetrahydrofuran at ambient temperature is provided. This method is easy to set up, inexpensive, scalable, time economical, accessible to any chemical laboratory, and capable of reducing a wide range of substrates. Importantly, the Birch reduction can be combined with organocuprate chemistry for the first time. Inner- and outer-sphere electron transfer processes may account for the inverse electron-demand reduction of arenes. Polyamines and t-butanol render the chemoselectivity and product selectivity of reductions tunable, making previously unattainable materials accessible.

For example, and without limitation, such a Birch reduction can include ethylenediamine as a ligand ($2.67/mol) and lithium in THF, e.g.,

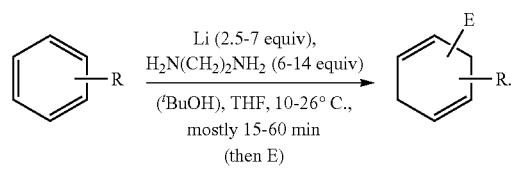

The relationship between ligand-structure-reactivity revealed new chemoselectivity. In the above example, $^t$BuOH was used to control product selectivity. Ethylenediamine ($2.67/mol can be removed by extraction. A broader scope was found of the electrophile (E) with copper (Cu). Sterics, linker length, and denticity (e.g.,

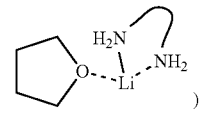

may all be investigated to improve the overall reaction. The tunability of polyamines for the reduction, including unprecedented inverse electron-demand chemoselectivity, was reported. Finally, more active roles for amines and alcohols than previously considered, providing a platform for controlling the chemoselectivity, is proposed.

Ammonia gas in a balloon and various amine-based ligands were tested for their suitability in the reaction of benzoic acid 1 to form a diene 2, in the following reaction:

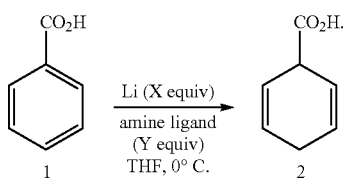 [SMILES: O=C(O)c1ccccc1 ; O=C(O)C1C=CCC=C1]

The results of these tests, described hereinafter, are shown in Table 1, below. Benzoic acid (PhCO$_2$H) 1 was chosen as the starting model substrate because of the deficiency of currently reported conditions for the reduction of electron-deficient arenes. First, a protocol with ammonia gas in a balloon (See, e.g., Altundas, A. et al. Excellent and convenient procedures for reduction of benzene and its derivatives. *Turk. J. Chem.*, 2005, 29, 513-518) to find that diene 2 was obtained in 83% yield was evaluated (Entry 1). However, this method was not effective for electron-rich substrates, typically resulting in incomplete reactions. Consequently, alternative amine-based ligands were investigated that could be broadly applicable, inexpensive, and easy to handle while affording the desired Birch reduction products. With 1.0 equivalent of ethylenediamine L1

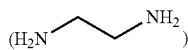

diene 2 was produced in 4% yield (Entry 2). Using 2.5 equivalents of L1 improved the yield to 83% (Entry 3). Using more L1 could reduce the amount of lithium and the time (90% yield, Entry 4).

The reaction did not proceed without L1 (Entry 5). Also, the combination of 1,2-diamine L1 and lithium was essential as there was no reduction when sodium metal was employed (Entry 6). It was then investigated whether the reaction could be improved further by fine-tuning the linker length and denticity of the ligand. 1,3-Diamine L2

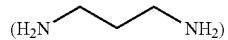

gave no product (Entry 7). Diethylenetriamine L3

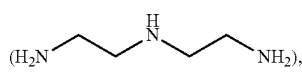

was as effective as L1, providing diene 2 in 86% yield (Entry 8), but triethylenetetramine L4

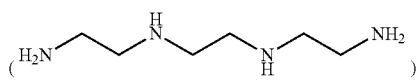

was ineffective (Entry 9). Other 1,2-diamines L5-L8 (where L5 is

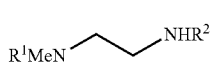

with R$^1$=R$^2$=H, L6 is

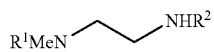

with R$^1$=H and R$^2$=methyl group, L7 is the cis isomer of

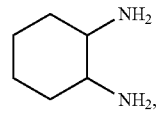

and L8 is the trans isomer of

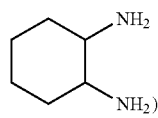

failed to promote the reduction (Entries 10-13). While L9

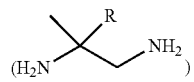

with R=H, had similar reactivity as L1, affording diene 2 in 85% yield (Entry 14), the reaction did not progress with L10, (e.g.,

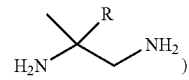

with R=methyl group (Entry 15). Although triamine L3 successfully reduced PhCO$_2$H 1 to diene 2, L1 was continued to be used (L1: $2.67/mol vs L3: $7.59/mol). Further, no reduction occurred with cyclic amine L12,

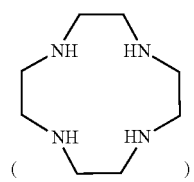 [SMILES: C1CNCCNCCNCCN1]

(Entry 16). The reaction could be scaled up to an 82-mmol scale, resulting in 95% isolated yield (Entry 17).

TABLE 1

The Birch reduction of PhCO$_2$H 1[a]

| Entry | X | Amine | Y | Time (h) | Yield (%)[b] |
|---|---|---|---|---|---|
| 1[c] | 5.0 | NH$_3$ in balloon | | 8 | 83[c] |
| 2 | 5.0 | L1 | 1.0 | 6 | 4 |
| 3 | 5.0 | L1 | 2.5 | 6 | 83 |
| 4 | 2.5 | L1 | 5.0 | 1 | 90 |
| 5 | 2.5 | None | | 1 | 0 |
| 6[d] | 3.0 | L1 | 6.0 | 1 | 0 |
| 7 | 2.5 | L2 | 5.0 | 1 | 0 |

TABLE 1-continued

The Birch reduction of PhCO$_2$H 1[a]

| Entry | X | Amine | Y | Time (h) | Yield (%)[b] |
|---|---|---|---|---|---|
| 8 | 2.5 | L3 | 5.0 | 1 | 86 |
| 9 | 3.0 | L4 | 6.0 | 1 | 0 |
| 10 | 2.5 | L5 | 5.0 | 1 | 0 |
| 11 | 2.5 | L6 | 5.0 | 1 | 0 |
| 12 | 2.5 | L7 | 5.0 | 1 | 0 |
| 13 | 2.5 | L8 | 5.0 | 1 | 0 |
| 14 | 3.0 | L9 | 6.0 | 1 | 85 |
| 15 | 3.0 | L10 | 6.0 | 1 | <5 |
| 16 | 3.0 | L12 | 6.0 | 1 | 0 |
| 17[e] | 3.0 | L1 | 6.0 | 1 | 95[f] |

[a]All reactions performed on a 4.0-mmol scale unless otherwise noted.
[b]Yield determined by $^1$H NMR using 1-methoxyadamantane as an internal standard.
[c]400-mmol scale. 0 to 25° C.
[d]Sodium metal used instead of lithium.
[e]82-mmol scale and increased equivalencies.
[f]Isolated yield.

Next, the reaction conditions for an electron-rich system using n-butoxybenzene (BuOPh) 3 as a model substrate were optimized for the following reaction:

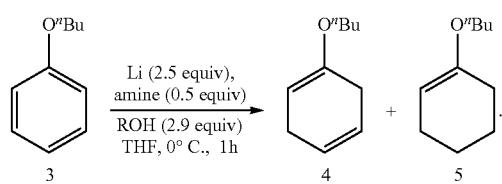

This substrate was not reduced without alcohol present (Entry 18). This substrate was not reduced without alcohol present (Table S2, entry 1). This is consistent with the known mechanism in which electron-rich arenes cannot accept the second electron unless the radical anion intermediate is protonated to form the corresponding radical species (see, for example, Rabideau, P. W. The metal-ammnia reduction of aromatic compounds. *Tetrahedron* 1989, 45, 1579-1603). Also, we did not observe any of the dealkylated phenol byproduct that was reported in the method developed in Shindo, T. et al. Scope and limitations of lithium-ethylenediamine-THF-mediated cleavage at the α-position of aromatics: Deprotection of aryl methyl ethers and benzyl ethers under mild conditions *Synthesis,* 2004, 692-700. With methanol, ethanol, isopropanol, t-butanol, and t-amyl alcohol, diene 4 was produced in 33, 58, 62, 75, and 68% yield, respectively, with the over-reduced product 5 in 4-11% yield (Entries 19-23). To study the importance of the acidity of the alcohol, 2,2,2-trifluoroethanol and 1,1,1,3,3,3-hexafluoroisopropanol were tested, which afforded yields of 52 and 26%, respectively (Entries 24 and 25). Use of 1,3-diamine L2 and triamine L3 diminished yields to 33 and 9%, respectively (Entries 26 and 27). Interestingly, the yield was increased to 51% with tetramine L4 (Entry 28; cf. Entry 26). The reaction did not proceed when sodium was used in lieu of lithium (Entry 29). With L5, L6 or L11

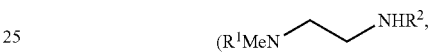

with R$^1$=methyl group and R$^2$=H), diene 4 was produced in 33, 3, and 27% yield, respectively (Entries 30-32). When employing cyclic amine L12, no reduction occurred (Entry 33). Interestingly, trans diamine L7 was ineffective even after 3 h (Entry 34), and cis diamine L8 promoted the reduction albeit more slowly than L1 (Entries 35 and 36). Use of diamines L9 and L10 produced diene 4 in 65% and 11% (Entries 37 and 38). To fully consume the starting material, the equivalents of lithium and L1 were increased (Entry 39).

TABLE 2

The Birch reduction of $^n$BuOPh 3[g]

| Entry | Amine | ROH | % yield[b] 4 | % yield[b] 5 | Entry | Amine | ROH | % yield[b] 4 | % yield[b] 5 |
|---|---|---|---|---|---|---|---|---|---|
| 18 | L1 | none | 0 | 0 | 29[d] | L1 | $^t$BuOH | 0 | 0 |
| 19 | L1 | MeOH | 33 | 4 | 30 | L5 | $^t$BuOH | 33 | ND[k] |
| 20 | L1 | EtOH | 58 | 9 | 31 | L6 | $^t$BuOH | 3 | ND |
| 21 | L1 | $^i$PrOH | 62 | 8 | 32 | L11 | $^t$BuOH | 27 | ND |
| 22 | L1 | $^t$BuOH | 75 | 11 | 33[h] | L12 | $^t$BuOH | 0 | 0 |
| 23 | L1 | t-amyl-OH | 68 | 8 | 34[i] | L7 | $^t$BuOH | 0 | ND |
| 24 | L1 | TFE | 52 | 7 | 35 | L8 | $^t$BuOH | 11 | ND |
| 25 | L1 | HFIP | 26 | 3 | 36[i] | L8 | $^t$BuOH | 73 | ND |
| 26 | L2 | $^t$BuOH | 33 | 6 | 37[j] | L9 | $^t$BuOH | 65 | 9 |
| 27 | L3 | $^t$BuOH | 9 | 1 | 38[j] | L10 | $^t$BuOH | 11 | 3 |
| 28 | L4 | $^t$BuOH | 51 | 10 | 39[h,j] | L1 | $^t$BuOH | 85 | 15 |

[g]All reactions run on a 3.3-mmol scale unless otherwise noted.
[h]2.5 equiv of $^t$BuOH used.
[i]Reaction time was increased to 3 h.
[j]3 equiv of lithium and 6 equiv of L1 used.
[k]ND = not determined.

Because the beginning of the reaction involves the dissolution of solid lithium, it was investigated if the stirring rate played a role and found that the reaction proceeded faster at the greater stir rate, the results of which are shown in Table 3 (Entry 29 vs Entry 30). In Entries 29-31 in Table 3, n-butyl phenyl ether 3, 1,2-diamine L1, tert-butyl alcohol, lithium, and THF were used. Although the Birch reduction proceeds through a radical anion intermediate, the use of distilled and degassed THF only mildly improved the yield (Entry 31).

TABLE 3

The Birch reduction of n-butyl phenyl ether[j]

| Entry | Stir Rate (RPM) | % yield 5 min 4 | % yield 5 min 5 | % yield 10 min 4 | % yield 10 min 5 | % yield[b] 60 min 4 | % yield[b] 60 min 5 |
|---|---|---|---|---|---|---|---|
| 29 | 300 | 1 | 0 | 4 | 0 | 4 | — |
| 30 | 600 | — | — | 15 | — | 80 | 12 |
| 31[m] | 600 | 16 | 2 | 30 | 4 | 83 | 12 |

[j]All reactions run on a 3.3 mmol scale unless otherwise noted.
[m]With distilled and degassed THF.

To develop a more scalable procedure, it was important that the reaction be performed at synthetically relevant concentrations. For Entries 32-35 in Table 4, n-butyl phenyl ether 3, 1,2-diamine L1, tert-butyl alcohol, lithium, and THF were used. When n-butyl phenyl ether was used as a substrate, its concentration had an effect on both the reaction rate and side product formation, as shown in Table 4, the results of which are graphed in FIG. 1. Specifically, when the concentration of the starting material (SM) was above 0.4 M, both the yield of the desired product and reaction rate increased (Entries 32-35).

TABLE 4

The Birch reduction of n-butyl phenyl ether[n]

| Entry | [SM] (M) | % yield[b] 5 min 4 | % yield[b] 5 min 5 | % yield[b] 10 min 4 | % yield[b] 10 min 5 | % yield[b] 15 min 4 | % yield[b] 15 min 5 | % yield[b] 60 min 4 | % yield[b] 60 min 5 |
|---|---|---|---|---|---|---|---|---|---|
| 32 | 0.1 | 8 | — | 24 | 3 | 36 | 4 | 70 | 10 |
| 33 | 0.2 | 11 | — | 39 | 5 | 57 | 7 | 76 | 11 |
| 34 | 0.4 | 35 | 5 | 62 | 8 | 76 | 11 | 71 | 20 |
| 35 | 0.8 | 74 | 10 | 84 | 12 | 85 | 14 | 51[o] | 23 |

[n]All reactions were performed on a 20-mmol scale unless otherwise noted.
[o]1-OBu-1,3-cyclohexadiene formed in ~23% yield.

Figure 2:
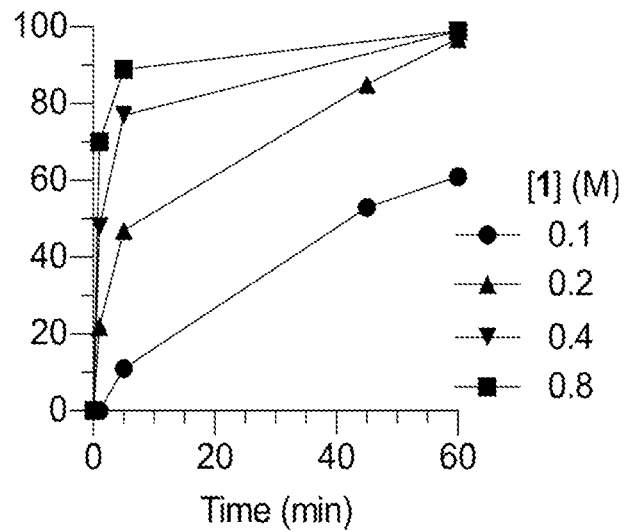
FIG. 2 is a graph depicting the % yield of diene 2 at different stifling times for different concentrations of benzoic acid 1.

With benzoic acid, the reduction could be performed at 0.8 M without loss of yield, as shown in Table 5 (Entries 36-39), the results of which are graphed in FIG. 2. In Entries 36-39 of Table 5, benzoic acid 1, 1,2-diamine L1, lithium, and THF were used.

TABLE 5

The Birch reduction of benzoic acid[n]

| Entry | [SM] (M) | % yield[b] 1 min 2 | % yield[b] 5 min 2 | % yield[b] 45 min 2 | % yield[b] 60 min 2 |
|---|---|---|---|---|---|
| 36 | 0.1 | 0 | 11 | 53 | 61 |
| 37 | 0.2 | 22 | 47 | 85 | 97 |
| 38 | 0.4 | 48 | 77 | 83 | 99 |
| 39 | 0.8 | 70 | 89 | 86 | 99 |

Figure 6A:
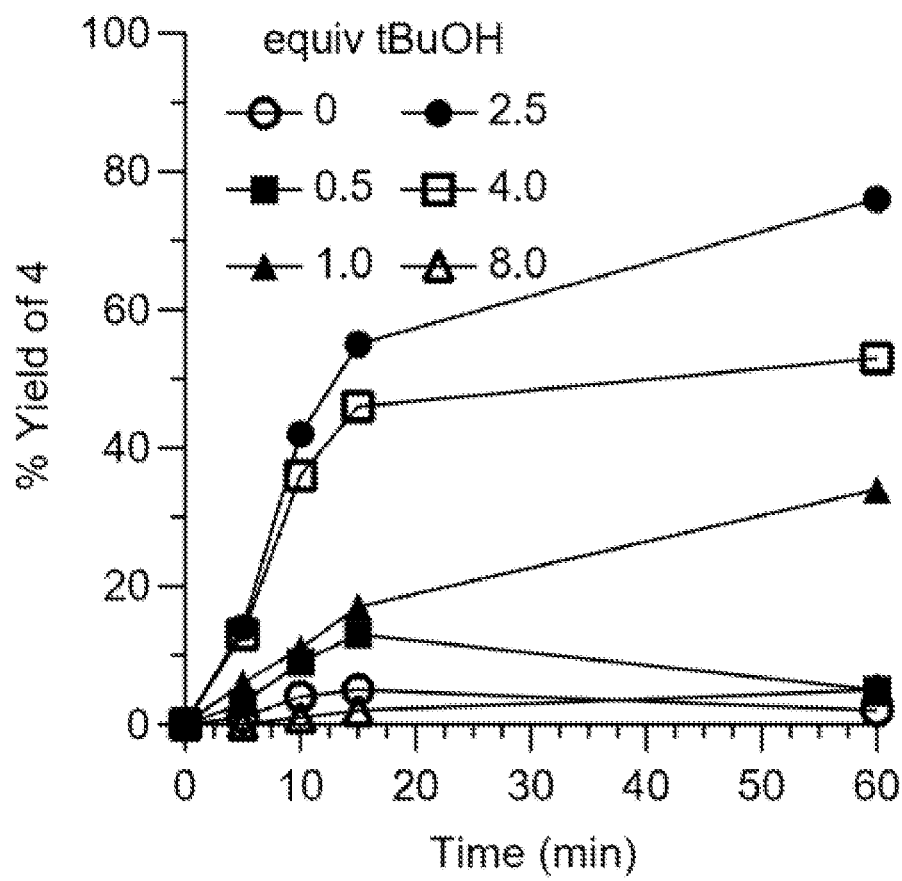
FIG. 6A is a graph depicting the % yield of diene 4 in the reduction of n-butyl phenyl ether 3 at different stifling times for different equivalences of n-butyl phenyl ether 3.

After optimization of butyl phenyl ether, the substrate scope of electron rich and neutral systems was explored. For the development of scalable procedures, it would be desirable to perform the reaction at higher concentrations. It was found (see FIG. 6A) that the PhCO$_2$H and $^n$BuOPh concentrations could be increased up to 0.8 M, which also accelerated the reduction. While the yield of diene 2 was unaffected, the increased reaction rate led to mono-olefin 5 and the 1,3-cyclohexadiene 4 with $^n$BuOPh 3 (see FIG. 6A). To further improve the scalability, lithium was suspended in THF the flask was cooled on ice, to which a solution of L1 and PhCO$_2$H in THF was added. This procedure was equally effective when the reaction was scaled up to a 0.50-mole scale. Monitoring the internal temperature revealed that the reaction proceeded at approximately 10° C.; therefore, it was decided to keep the internal temperature in the 10-26° C. range. The 0.50-mole scale reaction took 1 h including preparation and workup to obtain diene 2 in 95% yield. A similar reverse-addition protocol was applied to both 4-methyl anisole and 4-OTBS toluene. It was necessary to add t-butanol to the suspension last to suppress both the overreduction and isomerization of the desired product to the 1,3-cyclohexadiene. 4-Methyl anisole was reduced to diene 22

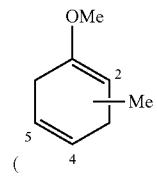

with the methyl group in the 4 position) in a 68% yield, while 4-OTBS toluene (10-g scale) was reduced to diene 23, i.e.,

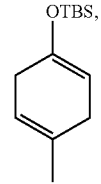

in a 76% yield. Both of these experiments (setup+reaction+isolation of the products) also took 1 h, which is substantially shorter than the known art (1-2 days) (See, e.g., Peters, B. K. et al. Scalable and safe synthetic organic electroreduction inspired by Li-ion battery chemistry. *Science,* 2019, 363, 838-845). Also, it was found that the reaction proceeded faster with a greater stir rate. Finally, the current method is compatible with trace water and air as the use of distilled and degassed THF only mildly improved the yield (78% vs 75%).

Figure 3:
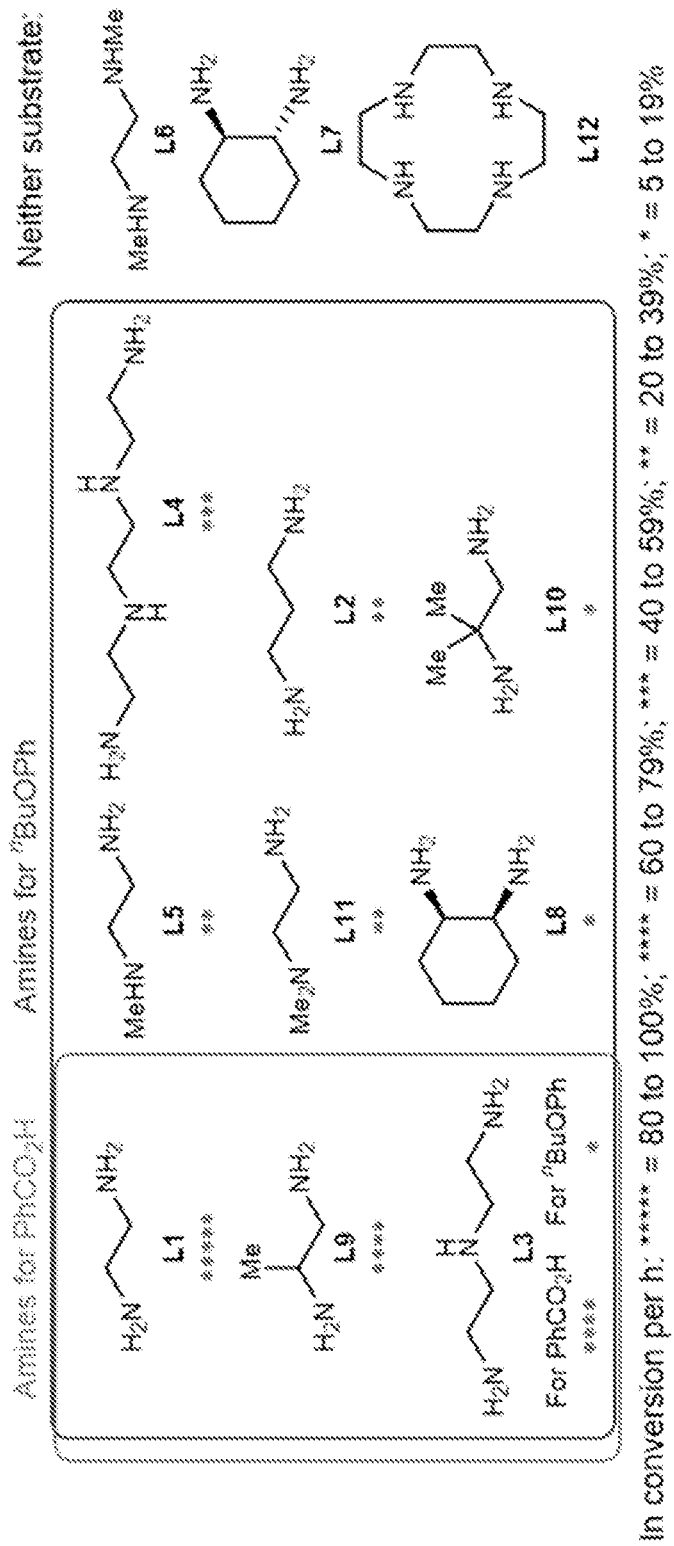
FIG. 3 is a chart of the non-limiting amine ligands acceptable for the reduction of benzoic acid 1 and n-butyl phenyl ether 2.
Figure 4:
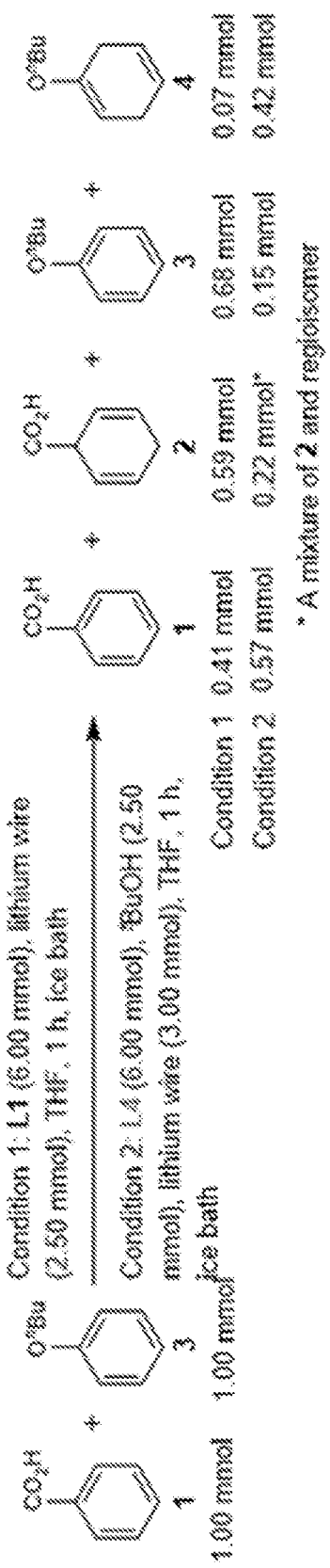
FIG. 4 is a schematic of normal chemoselectivity with ethylenediamine L1 and reversed chemoselectivity with triethylenetetramine L4.
Figure 5A:
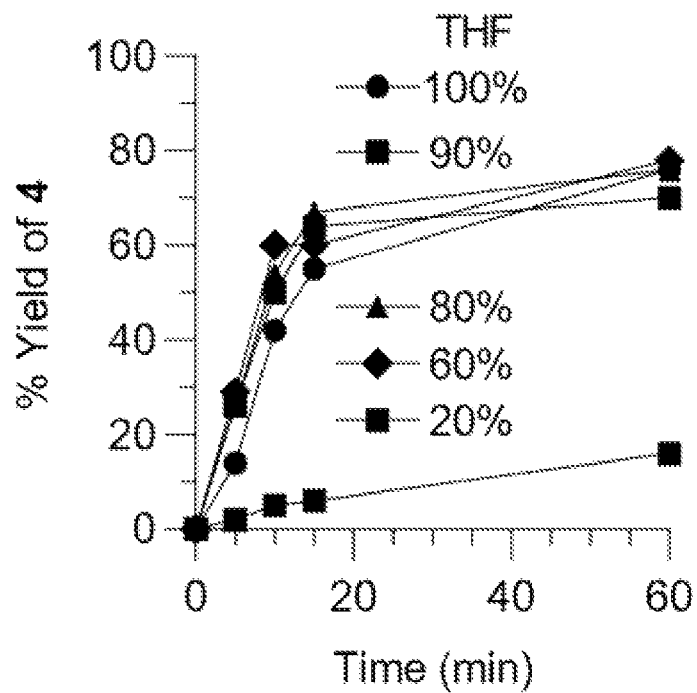
FIG. 5A is a graph depicting the % yield of diene 4 in the reduction of n-butyl phenyl ether 3 at different stifling times for different levels of THF.
Figure 5B:
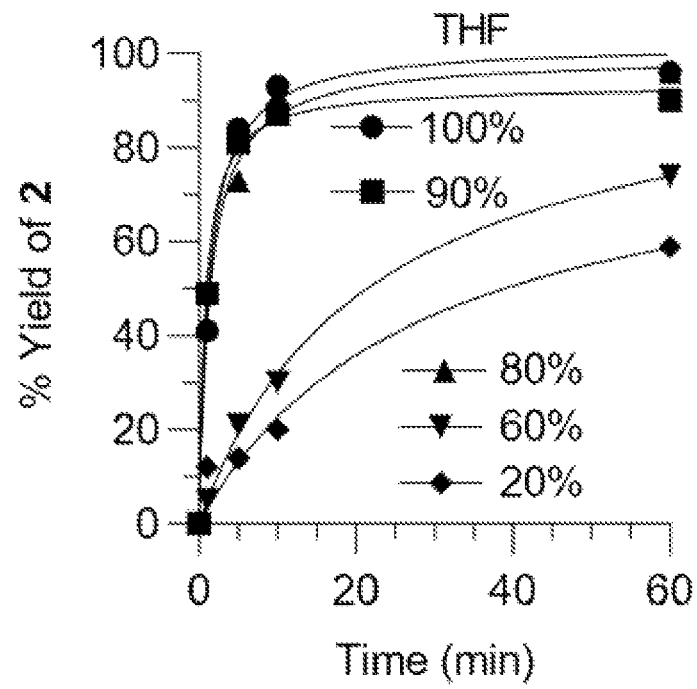
FIG. 5B is a graph depicting the % yield of diene 2 in the reduction of benzoic acid 1 at different stirring times for different levels of THF.
Figure 5C:
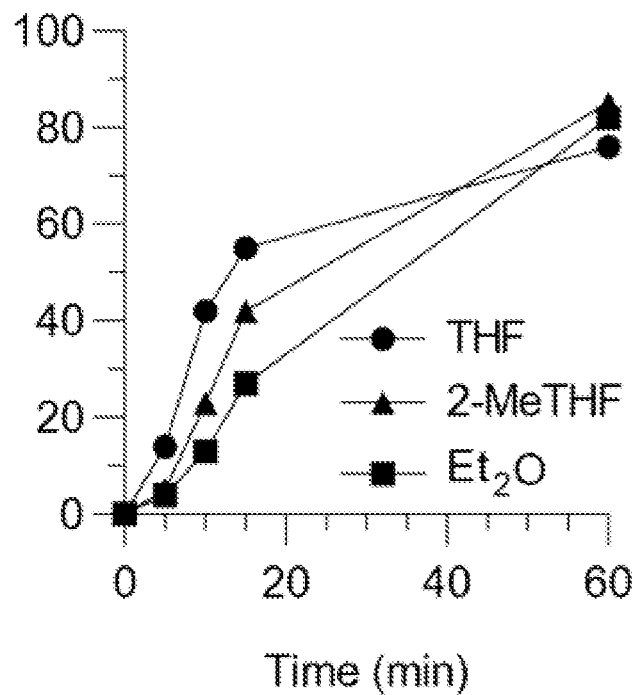
FIG. 5C is a graph depicting the % yield of diene 4 in the reduction of n-butyl phenyl ether 3 at different stifling times for different ethereal solvents.
Figure 5D:
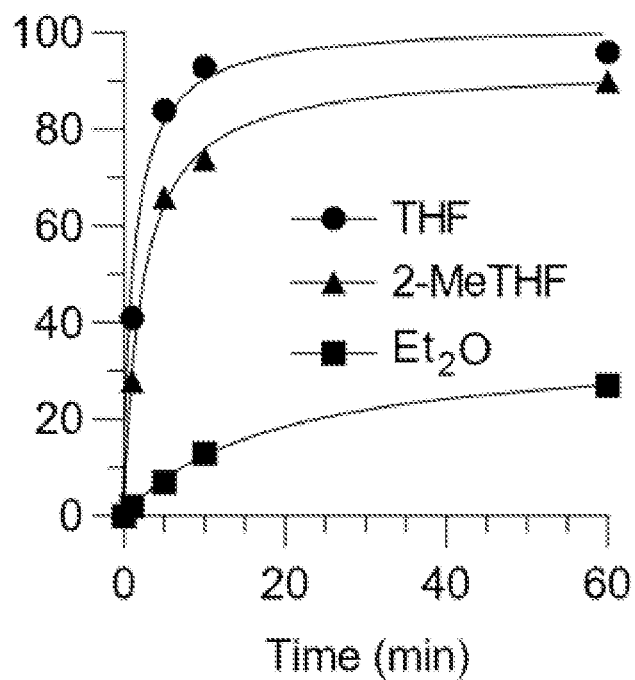
FIG. 5D is a graph depicting the % yield of diene 2 in the reduction of benzoic acid 1 at different stirring times for different ethereal solvents.
Figure 5E:
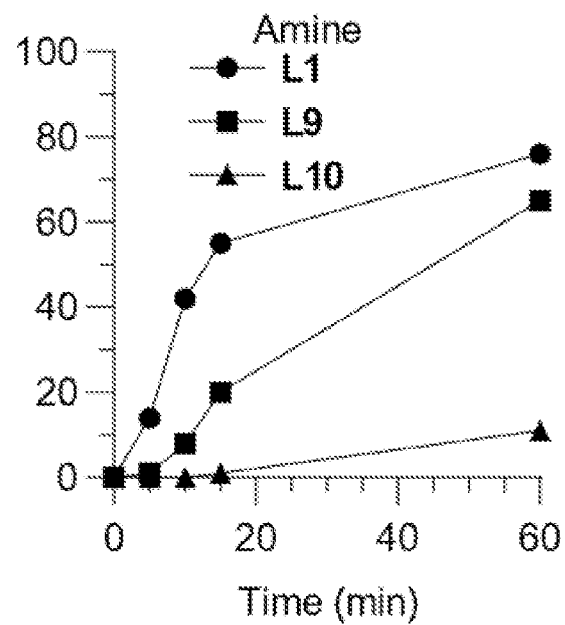
FIG. 5E is a graph depicting the % yield of diene 4 in the reduction of n-butyl phenyl ether 3 at different stirring times for different amine ligands.
Figure 5F:
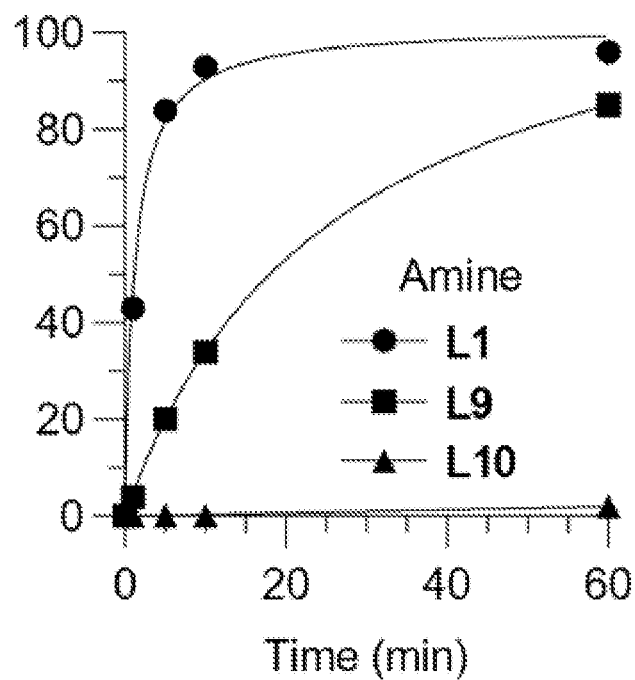
FIG. 5F is a graph depicting the % yield of diene 2 in the reduction of benzoic acid 1 at different stirring times for different amine ligands.
Figure 5G:
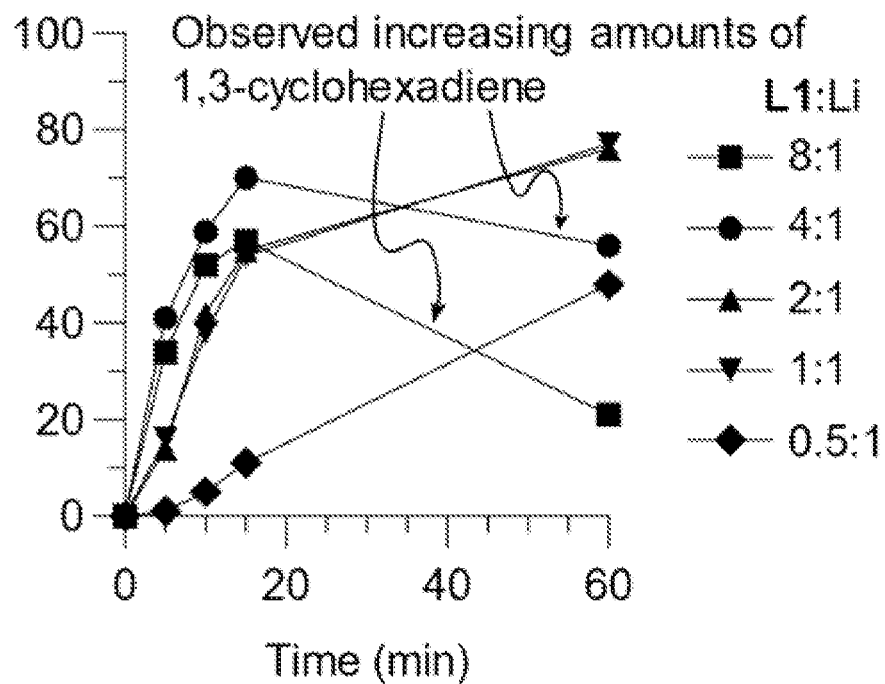
FIG. 5G is a graph depicting the % yield of diene 4 in the reduction of n-butyl phenyl ether 3 at different stirring times for different ratios of ethylenediamine L1 to lithium.
Figure 5H:
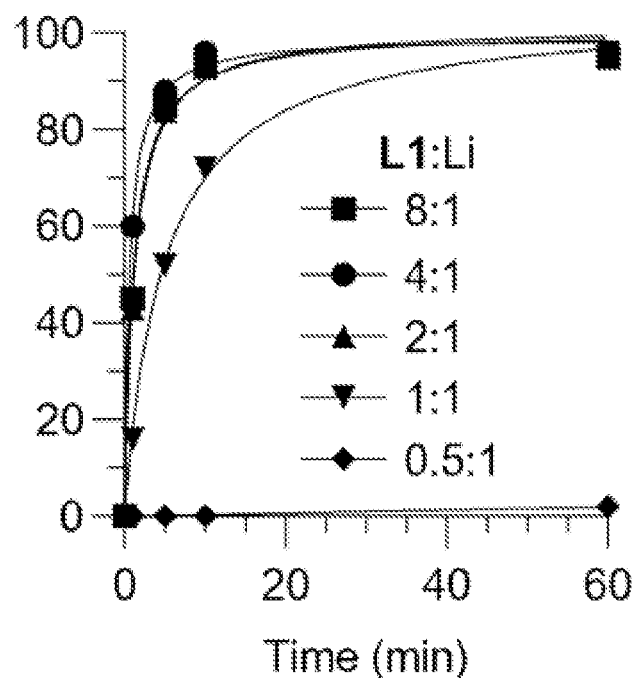
FIG. 5H is a graph depicting the % yield of diene 2 in the reduction of benzoic acid 1 at different stirring times for different ratios of ethylenediamine L1 to lithium.

Generally, electron-withdrawing groups increase reduction rates while electron-donating groups decrease them. Specifically, the Birch reduction of benzoate is more than 61 times faster than that of anisole under traditional conditions (See, e.g., Krapcho, A. P. et al. Kinetics of the metal-ammonia-alcohol reductions of benzene and substituted benzenes. *J. Am. Chem. Soc.*, 1959, 81, 3658-3666). In FIG. 3, the results from the ligand screen in Tables 1 and 2 are summarized; in the left, smaller rectangle are the ligands that reduced $PhCO_2H$ while in the right, larger rectangle (which includes those ligands that reduced $PhCO_2H$) are the ligands that reduced "BuOPh. The summary suggested that it might be possible to reduce an electron-rich arene in preference to an electron-deficient arene. A reduction with an equimolar mixture of $PhCO_2H$ and "BuOPh, L1 and lithium without t-butanol was performed to obtain acid 2 and ether 4 in a 59 and 7% yield, respectively (see FIG. 4). The same conditions with t-butanol gave a mixture of acid 2 along with other intractable products. The earlier results were then exploited by replacing L1 with tetramine L4 to discover that the electron-rich arene "BuOPh was more reactive than the electron-deficient arene $PhCO_2H$ (43% consumption of $PhCO_2H$ vs. 85% consumption of "BuOPh), affording 2 and 4 in a 1:2 ratio.

The liquid ammonia solvent in the Birch reduction has hampered leveraging the carbanion intermediate. For example, a Birch alkylation with methyl vinyl ketone failed because ammonia caused the polymerization of the ketone (See, e.g., Rao, G. S. R. S. et al. Michael reactions of the anions generated by the metal-ammonia reduction of benzoic acids. *J. Chem. Soc., Chem. Comm.*, 1980, 315-316). Given the use of only 6 equivalents of L1, it was hypothesized that the Birch reduction could be coupled with cuprate chemistry. After the reduction of $PhCO_2H$ under these reaction conditions, CuI and methyl vinyl ketone were added:

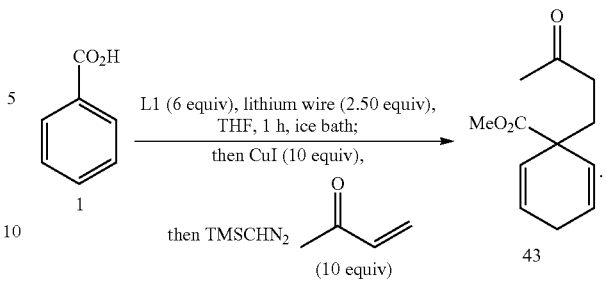

Under these unoptimized conditions, ketone 43 was generated in 20% yield while forming a quaternary carbon.

The kinetics were then investigated for both "BuOPh and $PhCO_2H$ under various conditions, as shown in FIGS. 5A-5H. First, it was found that the reduction rates depended upon THF concentrations, as well as the choice of ethereal solvent (see FIGS. 5A-5D). The decreasing polarity of the reaction medium most likely affects the stability and solubility of the radical anion that is usually stabilized by ammonia (See, e.g, Brezina, K. et al. Benzene radical anion in the context of the Birch reduction: When solvation is the key. *J. Phys. Chem. Lett.*, 2020, 11, 6032-6038). Next, as L1:lithium ratio increased (see FIGS. 5E and 5F) so did the reaction rate (see FIGS. 5G and 5H). However, the reduction of "BuOPh produced increasing amounts of 1-butoxy-1,3-cyclohexadiene 4 as well as mono-olefin 5. This is similar to the results in which only the initial concentration of the reaction mixture was increased.

Figure 6B:
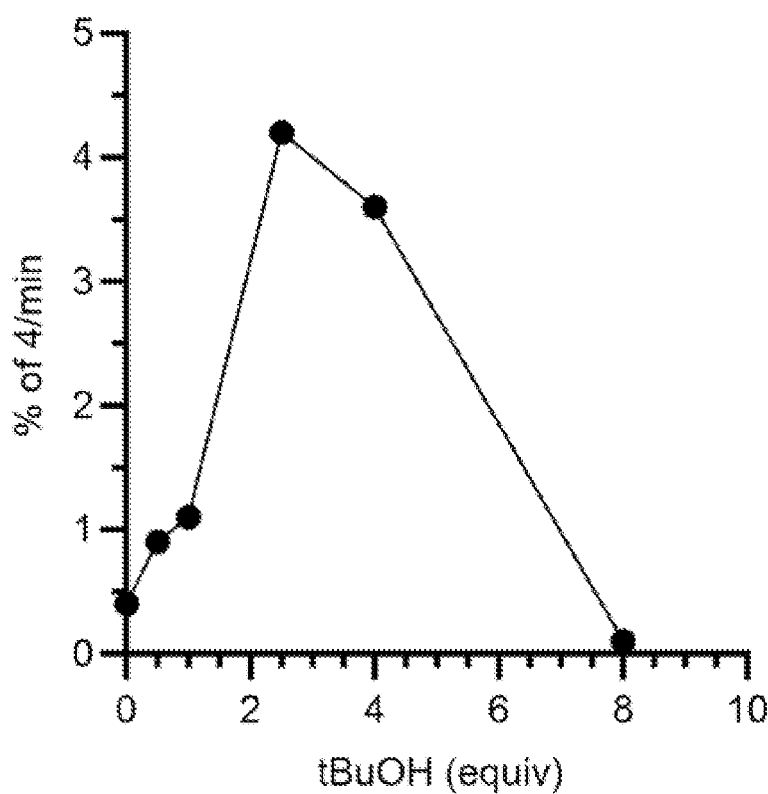
FIG. 6B is a graph depicting the % yield per minute of diene 4 in the reduction of n-butyl phenyl ether 3 for different equivalences of n-butyl phenyl ether 3.

Finally, the reduction rate steadily increased when changing from 0 equivalents to 2.5 equivalents of t-butanol. However, when increasing the equivalents of t-butanol past 2.5, the reduction rate decreased (see FIGS. 6A-6B).

From the data presented here, it is propose that the reduction of $PhCO_2H$ proceeds as follows:

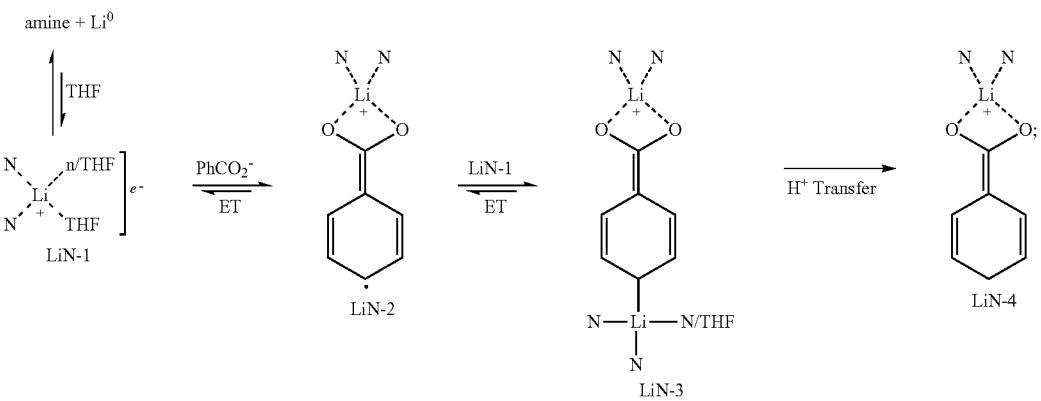

first, lithium(0) is dissolved through the coordination of the amine ligand and THF to create LiN-1. Second, an electron transfer occurs to give radical anion LiN-2. Subsequently, another electron transfer occurs to afford trianion LiN-3, which may be in equilibrium with higher order aggregates. Lastly, this species is protonated to form LiN-4.

The following shows our hypothesized mechanism for the reduction of $^n$BuOPh:

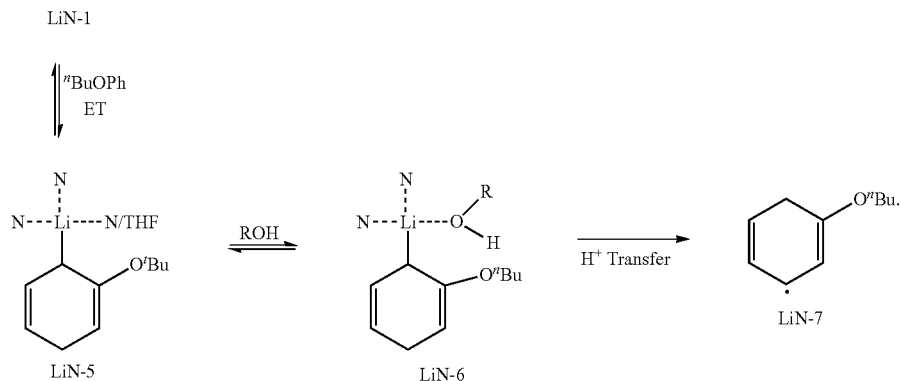

An electron is tranferred from LiN-1 to the substrate to form radical anion LiN-5. Next, t-butanol binds the lithium to give LiN-6, which triggers the rate-determining intramolecular protonation to form the radical species LiN-7. In both of these cases, the lithium dissolution and electron transfer are in equilibrium.

To understand the ligand's impact on reactivity, the dissolution of lithium(0) was first considered. If the dissolution step accounts for the structure-reactivity relationship, the effective amines should dissolve lithium faster than ineffective amines (FIG. 3). The qualitative experiments with lithium and ethylenediamine, cis-, or trans-1,2-diaminocyclohexane in THF without arenes showed that while ethylenediamine partially dissolved lithium, the other two amines did not. This is distinct from the fast dissolution of lithium in the presence of arene substrates. Therefore, dissolution alone cannot account for the structure-reactivity relationship.

Second, the imparct of the ligand structure on the electron transfer processes were considered. It was reasoned that as the denticity of the ligand increases from ethylenediamine to diethylenetriamine then to triethylenetetramine, the amino groups displace the benzoate of LiN-2 with nitrogens, disrupting the eletron transfer step, particularly if this is an inner-sphere electron transfer. Currently, it is unclear how many nitrogen atoms are bound to lithium in each intermediate, but the failure with cyclic amine L12 suggests that when four amino groups are bound, such a complex appears unreactive. Steric effects of amines warrant further studies.

Third, the influence that amines have on the rate-determining protonation step for the reduction of $^n$BuOPh was considered. Organolithum's carbon is protonated faster with 1,2-diamines than with 1,3-diamines. Therefore, it is suggested that the protonations of LiN-3 and LiN-6 are faster with ethylenediamine than with 1,3-diaminopropane.

Fourth, consideration was given to how the alcohol affects the protonation and product distribution in the reduction. The alcohol may play a more significant role than only a proton donor. For example, if t-butanol intermolecularly protonates radical anion LiN-5, the rate should be linearly proportional to the alcohol concentration. Instead, we observed a bell-shaped trend, indicating that protonation may occur intramolecularly through LiN-6. The slight preference between related substrates with different steric environments bodes well with this hypothesis. Importantly, the reaction mixture containing $^n$BuOPh turned light blue with 8 equiv of t-butanol, although the desired reduction did not occur. This suggests excess alcohol may outcompete amino groups on the lithium at an earlier stage of the reaction, forming less reductive solvated electrons, similar to work with SmI$_2$ (See, e.g., Shabangi, R. A. et al. Electrochemical invesitgation of the reducing power of SmI2 in THF and the effect of HMPA cosolvent. *Tetrahedron Lett.*, 1997, 38, 1137-1140). A mass effect may have obscured the additional role of t-butanol in the past; traditionally, the amine has been used in greater excess than the alcohol, outcompeting the alcohol for coordination to the lithium.

When less than 1 equiv of t-butanol was present in the reduction of $^n$BuOPh, the monoolefin was formed in ca. 20% yield. This is similar to the reduction without alcohol (See, e.g., Benkeser R. A. et al. Reduction of organic compounds by lithium in low molecular weight amines. III. Reduction of aromatic compounds containing functional groups. *J. Am. Chem. Soc.*, 1955, 77, 6042-6045 and Benkeser R. A. et al. Reduction of organic compounds by lithium in low molecular weight amines. I. Selective reduction of aromatic hydrocarbons to monoolefins. *J. Am. Chem. Soc.*, 1955, 77, 3230-3233). Although the addition of an alcohol under the Benkeser-type conditions gave Birch-type products, these findings have not garnered widespread use. The alcohol is necessary to synthesize Birch products by protonating both the organolithiated species (LiN-5 or LiN-6) and the lithium amide in the reaction mixture. The protonation of the lithium amide then hinders the isomerization of the 1,4-diene to the 1,3-diene, slowing the formation of the monoolefin. Potential effects of t-butoxide would warrant further investigation.

Also, literature has shown that more acidic alcohols (methanol, ethanol) give faster reductions but lower yields than bulkier alcohols (isopropanol, t-butanol) because of an off reaction with lithium to create H$_2$ (See, e.g., Krapcho, A. P. et al. Kinetics of the metal-ammonia-alcohol reductions of benzene and substituted benzenes. *J. Am. Chem. Soc.*, 1959, 81, 3658-3666 and Shabangi, R. A. et al. Electrochemical invesitgation of the reducing power of SmI2 in THF and the effect of HMPA cosolvent. *Tetrahedron Lett.*, 1997, 38, 1137-1140). Although the data mostly support such a notion, we wish to consider other factors based on the data with trifluoroethanol (52%), methanol (33%), and ethanol (58%)

combined with the structural requirements of the amine, including optimal bite angle (ethylenediamine vs 1,2-diamino-2-methypropane). For example, the equilibrium between a monomer and higher-order aggregates of various ligated lithium intermediates can be affected by the amine ligand, among other factors.

The switch of the solvent from an amine to an ethereal solvent (THF) was essential for this work. Ammonia gas in a balloon, lithium, and THF conditions (Altundas, A. et al. Excellent and convenient procedures for reduction of benzene and its derivatives. *Turk. J. Chem.*, 2005, 29, 513-518) suggests that the amine might not be needed as a solvent. 1,2-Dimethoxyethane was ineffective as the solvent, indicating that only one molecule of THF binds to a lithium ion to form reactive species. The role of THF as a ligand for the alkali metal ion most likely had not been considered before because the ethereal solvent was previously used in smaller amounts than the amine solvent.

The method could reverse the chemoselectivity for the reduction of $PhCO_2H$ and $^nBuOPh$ by two orders of magnitude with triethylenetetramine (61-fold difference under the standard Birch reduction conditions in favor of $PhCO_2H$ and 2-fold difference under the present conditions in favor of $^nBuOPh$). More broadly, the structure-reactivity relationship indicates the potential for (reverse) chemoselective reduction in synthesis. To control the selectivity, inner- and outer-sphere electron transfer processees may be considered. It may also be suggested a broader role for the alcohol than previously considered, including the product selectivity with naphthalene and indole systems.

In addition to the theoretical advancements, the practicality of the technology should render the lithium-mediated reduction and deprotection more accessible to a broader scientific community and more amenable to the time-economic synthesis of complex molecules. Finally, the scope of the Birch reduction may be expanded by combining the chemistry of organolithium with other organometallic chemistry.

DETAILED REACTIONS

Reagents

THF, ethylenediamine, and t-BuOH used in this study were not distilled.

General Procedure

Lithium wire was cut into approximately 1 cm pieces, and the pieces were added to the solution in portions over 2 min.
Specific Procedures
Reduction of benzoic acid to 1,4-dihydrobenzoic acid: The following procedure was performed for the reduction of benzoic acid to 1,4-dihydrobenzoic acid:

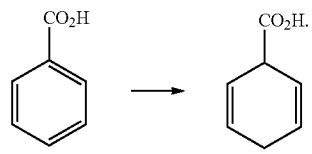 [SMILES: O=C(O)c1ccccc1 ; O=C(O)C1C=CCC=C1]

A single-neck, 500-mL round-bottom flask was equipped with a magnetic stir bar and a septum equipped with a needle connected to a bubbler as a gas outlet. Benzoic acid (5.00 g, 40.9 mmol), THF (140 mL), and ethylenediamine (16.4 mL, 246 mmol, 6.0 equivalents) were added to the flask, and the resulting mixture was cooled to 0° C. while stifling. Lithium (852 mg, 123 mmol, 3.0 equivalents) was added to the solution. The reaction mixture was stirred at 0° C. (external temperature) until TLC analysis showed the reaction to be complete (35 min). Cold water (50 mL) was added to the reaction mixture (CAUTION: Evolution of hydrogen gas, for this reaction and many of the reactions below), and the resulting mixture was stirred until the remaining lithium was quenched. The resulting mixture was cooled with an ice bath and acidified with concentrated HCl until pH=2. The mixture was concentrated under reduced pressure with a rotary evaporator until most THF was removed. The resulting mixture was poured to a 125-mL separatory funnel, and the product was extracted with $Et_2O$ (50 mL×3). The organic extracts were combined, dried over $Na_2SO_4$, filtered through cotton, and concentrated under reduced pressure to give 1,4-dihydrobenzoic acid as a pale-yellow oil (4.82 g, 95% yield).

Data for 1,4-dihydrobenzoic acid: $^1H$ NMR (300 MHz, $CDCl_3$, 294K) δ 11.52 (br s, 1H, COOH), 5.93 (m, 2H, $C_3$—H), 5.83 (m, 2H, $C_2$—H), 3.78 (m, 1H, $C_1$—H), 2.70 (m, 2H, $C_4$—H). This data matches that known in the art (See, e.g., Ashtekar, K. D. Nucleophile-assisted alkene activation: Olefins alone are often incompetent. *J. Am. Chem. Soc.*, 2016, 138, 8114-8119).

Reduction of o-toluic acid to 2-methyl-2,5-cyclohexadiene-1-carboxylic acid: The following procedure was performed for the reduction of o-toluic acid to 2-methyl-2,5-cyclohexadiene-1-carboxylic acid:

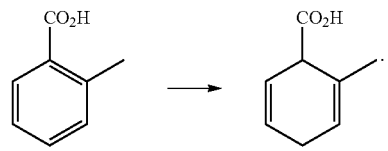

A single-neck, 100-mL round-bottom flask was equipped with a magnetic stir bar and a septum equipped with a needle connected to a bubbler as a gas outlet. o-Toluic acid (1.00 g, 7.35 mmol), THF (24 mL), and ethylenediamine (2.94 mL, 44.1 mmol, 6.0 equivalents) were added to the flask, and the resulting solution was stirred while cooling to 0° C. Lithium (153 mg, 22.0 mmol, 3.0 equivalents) was added to the solution. The reaction mixture was stirred at 0° C. (external temperature) until TLC analysis showed the reaction to be complete (30 min). Saturated aqueous $NH_4Cl$ (40 mL) was added to reaction mixture, and the resulting mixture was stirred until the remaining lithium was quenched. The resulting mixture was cooled with an ice bath and acidified with concentrated HCl until pH=2. The resulting mixture was concentrated under reduced pressure with a rotary evaporator until most THF was removed. The resulting mixture was poured to a 125-mL separatory funnel, and the product was extracted with $Et_2O$ (30 mL×3). The organic extracts were combined, dried over $Na_2SO_4$, filtered through cotton, and concentrated under reduced pressure. The resulting solid was determined to be pure by $^1H$ NMR spectroscopy to give 2-methyl-2,5-cyclohexadiene-1-carboxylic acid (971 mg, 97% yield) as a white solid.

Data for 2-methyl-2,5-cyclohexadiene-1-carboxylic acid: $^1H$ NMR (300 MHz, $CDCl_3$, 294K) δ 11.57 (s, 1H), 5.95 (m, 1H), 5.77 (m, 1H), 5.67 (br s, 1H), 3.64 (br q, 1H, J=3.9 Hz), 2.89-2.57 (m, 2H), 1.78 (s, 3H). This data matches that known in the art (See, e.g., Rao, G. S. R. S. Synthesis based on cyclohexadienes. Part 8. Synthesis of 1-methylbicyclo [2.2.2]oct-2-enecarboxylate derivatives. J. Chem. Soc., Perkin Trans. 1, 1993, 2333-2337).

Reduction of 2,6-dimethylbenzoic acid to 2,6-dimethyl-2,5-cyclohexadiene-1-carboxylic acid: The following procedure was performed for the reduction of 2,6-dimethylbenzoic acid to 2,6-dimethyl-2,5-cyclohexadiene-1-carboxylic acid:

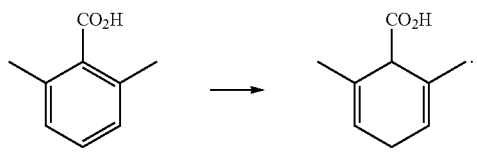

A single-neck, 100-mL round-bottom flask was equipped with a magnetic stir bar and a septum equipped with a needle connected to a bubbler as a gas outlet. 2,6-Dimethylbenzoic acid (1.00 g, 6.66 mmol), THF (22 mL), and ethylenediamine (2.67 mL, 20.00 mmol, 6.0 equivalents) were added to the flask, and the resulting solution was stirred while cooling to 0° C. Lithium (139 mg, 20.0 mmol, 3.0 equivalents) was added to the solution. The reaction mixture was stirred at 0° C. (external temperature) until TLC analysis showed the reaction to be complete (28 min). Saturated aqueous $NH_4Cl$ (40 mL) was added to reaction mixture, and the resulting mixture was stirred until the remaining lithium was quenched. The resulting mixture was cooled with an ice bath and acidified with concentrated HCl until pH=2. The resulting mixture was concentrated under reduced pressure with a rotary evaporator until most THF was removed. The resulting mixture was poured to a 125-mL separatory funnel, and the product was extracted with $Et_2O$ (30 mL×3). The organic extracts were combined, dried over $Na_2SO_4$, filtered through cotton, and concentrated under reduced pressure. The resulting solid was determined to be pure by $^1H$ NMR spectroscopy to give 2,6-dimethyl-2,5-cyclohexadiene-1-carboxylic acid (941 mg, 94% yield) as a white solid.

Data for 2,6-dimethyl-2,5-cyclohexadiene-1-carboxylic acid: $^1H$ NMR (300 MHz, $CDCl_3$, 294K) δ 5.68 (br s, 2H), 3.48 (t, 1H, J=6.3 Hz), 2.88-2.56 (m, 2H), 1.78 (s, 6H).

Reduction of 3,5-dimethylbenzoic acid to 3,5-dimethyl-2,5-cyclohexadiene-1-carboxylic acid: The following procedure was performed for the reduction of 3,5-dimethylbenzoic acid to 3,5-dimethyl-2,5-cyclohexadiene-1-carboxylic acid:

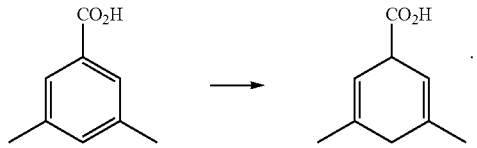

A single-neck, 100-mL round-bottom flask was equipped with a magnetic stir bar and a septum equipped with a needle connected to a bubbler as a gas outlet. 3,5-Dimethylbenzoic acid (1.00 g, 6.66 mmol), THF (22 mL), ethylenediamine (2.67 mL, 40.0 mmol, 6.0 equivalents), and 1-methoxyadamantane (160 mg, 1.0 mmol, 0.1 equiv, internal standard) were added to the flask, and the resulting solution was stirred while cooling to 0° C. Lithium (139 mg, 20.0 mmol, 3.0 equivalents) was added to the solution. The reaction mixture was stirred at 0° C. (external temperature) until TLC analysis showed the reaction to be complete (45 min). Saturated aqueous $NH_4Cl$ (40 mL) was added to reaction mixture, and the resulting mixture was stirred until the remaining lithium was quenched. The resulting mixture was cooled with an ice bath and acidified with concentrated HCl until pH=2. The resulting mixture was concentrated under reduced pressure with a rotary evaporator until most THF was removed. The resulting mixture was poured to a 125-mL separatory funnel, and the product was extracted with $Et_2O$ (30 mL×3). The organic extracts were combined, dried over $Na_2SO_4$, filtered through cotton, and concentrated under reduced pressure. The resulting solid was determined to be pure by $^1H$ NMR spectroscopy to give 3,5-dimethyl-2,5-cyclohexadiene-1-carboxylic acid (911 mg, 90% yield) as a white solid.

Data for 3,5-dimethyl-2,5-cyclohexadiene-1-carboxylic acid: $^1H$ NMR (300 MHz, $CDCl_3$, 294K) δ 5.53 (br s, 2H), 3.77 (m, 1H), 2.50 (br t, 2H, J=6.9 Hz), 1.75 (s, 6H). This data matches that known in the art (See, e.g., Bykova, T. et al. Multicomponent reactions of methyl substituted all-cis tetrafluorocyclohexane aldehydes. Org. Biomol. Chem., 2016, 14, 1117-1123).

Reduction of o-anisic acid to 2-methoxy-2,5-cyclohexadiene-1-carboxylic acid: The following procedure was performed for the reduction of o-anisic acid to 2-methoxy-2,5-cyclohexadiene-1-carboxylic acid:

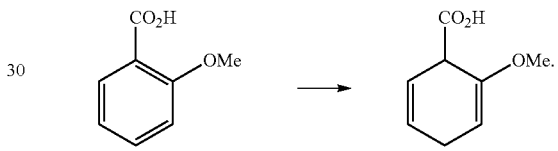

A single-neck, 100-mL round-bottom flask was equipped with a magnetic stir bar and a septum equipped with a needle connected to a bubbler as a gas outlet. o-Anisic acid (1.00 g, 6.57 mmol), THF (22 mL), and ethylenediamine (2.63 mL, 39.4 mmol, 6.0 equivalents) were added to the flask, and the resulting solution was stirred while cooling to 0° C. Lithium (137 mg, 19.7 mmol, 3.0 equivalents) was added to the solution. The reaction mixture was stirred at 0° C. (external temperature) until TLC analysis showed the reaction to be complete (41 min). Saturated aqueous $NH_4Cl$ (40 mL) was added to reaction mixture, and the resulting mixture was stirred until the remaining lithium was quenched. The resulting mixture was cooled with an ice bath and acidified with concentrated HCl until pH=2. The resulting mixture was concentrated under reduced pressure with a rotary evaporator until most THF was removed. The resulting mixture was poured to a 125-mL separatory funnel, and the product was extracted with $Et_2O$ (30 mL×3). The organic extracts were combined, dried over $Na_2SO_4$, filtered through cotton, and concentrated under reduced pressure. The resulting residue was purified by flash column chromatography ($SiO_2$, 5 to 20% EtOAc in hexanes with 1% acetic acid) to give 2-methoxy-2,5-cyclohexadiene-1-carboxylic acid (341 mg, 34% yield) as a white solid.

Data for give 2-methoxy-2,5-cyclohexadiene-1-carboxylic acid: $R_f$=0.23 (1% AcOH and 40% EtOAc in hexanes stained with $I_2$); $^1H$ NMR (500 MHz, $CDCl_3$, 296K) δ 10.47 (br s, 1H, COOH), 5.93 (m, 1H, $C_6$—H), 5.73 (dddd, 1H, J=9.8, 4.0, 2.5, 2.5 Hz, $C_5$—H), 4.88 (br t, 1H, J=4.0 Hz, $C_3$—H), 3.81 (overlapping dddd, J=8.8, 6.6, 3.7, 2.5 Hz, 1H, $C_1$—H), 3.59 (s, 3H, $OCH_3$), 2.92 (ddddd, 1H, J=22.4, 8.8, 6.6, 3.7, 2.5 Hz, $C_4$—H), 2.81 (dddddd, 1H, J=22.4, 8.8, 4.0, 3.7, 2.5 Hz, $C_{4'}$—H); $^{13}C$ NMR (125 MHz, $CDCl_3$, 294K)

δ 177.0, 149.9, 127.7, 121.0, 93.6, 54.4, 45.7, 26.3; IR (neat) 2893, 2824, 1708, 1684, 1651, 1211 cm$^{-1}$; HRMS (ESI-TOF) m/z for [M−H]$^-$ C$_8$H$_9$O$_3$, calculated 153.05462, found 153.05467; m.p. 62-64° C.

Conversion of m-anisic acid to 5-oxo-2-cyclohexene-1-carboxylic acid: The following procedure was performed for the conversion of m-anisic acid to 5-oxo-2-cyclohexene-1-carboxylic acid:

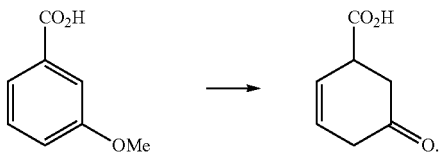 [SMILES: COc1cccc(C(=O)O)c1 ; O=C1CC=CC(C(=O)O)C1]

The following procedure was performed for the reduction of A single-neck, 100-mL round-bottom flask was equipped with a magnetic stir bar and a septum equipped with a needle connected to a bubbler as a gas outlet. m-Anisic acid (1.00 g, 6.57 mmol), THF (22 mL) and ethylenediamine (2.57 mL, 39.4 mmol, 6.0 equivalents) were added to the flask, and the resulting solution was stirred while cooling to 0° C. Lithium (137 mg, 19.7 mmol, 3.0 equivalents) was added to the solution. The reaction mixture was stirred at 0° C. (external temperature) until TLC analysis showed the reaction to be complete (25 min). Saturated aqueous NH$_4$Cl (40 mL) was added to reaction mixture, and the resulting mixture was stirred until the remaining lithium was quenched. The resulting mixture was cooled with an ice bath and acidified with concentrated HCl until pH=2. The resulting mixture was concentrated under reduced pressure with a rotary evaporator until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The resulting residue was purified by flash column chromatography (SiO$_2$, 5 to 60% EtOAc in hexanes with 1% acetic acid) to give 5-oxo-2-cyclohexene-1-carboxylic acid (611 mg, 61% yield) as a white solid.

Data for 5-oxo-2-cyclohexene-1-carboxylic acid: R$_f$=0.28 (1% AcOH and 60% EtOAc in hexanes stained with I$_2$); $^1$H NMR (500 MHz, CDCl$_3$, 296K) δ 9.82 (br s, 1H, COOH), 6.04 (dddd, J=9.9, 3.9, 1.7, 1.7 Hz, 1H, C$_6$—H), 5.99 (dddd, 1H, J=9.9, 3.4, 3.2, 1.7 Hz, C$_5$—H), 3.63 (ddddd, 1H, J=8.2, 6.2, 3.9, 2.0, 2.0 Hz, C$_1$—H), 3.00 (dddd, 1H, J=6.8, 2.0, 2.0, 2.0 Hz, C$_4$—H), 2.95-2.87 (m, 1H, C$_4$—H), 2.78 (dd, 1H, J=15.3, 6.4 Hz, C$_6$—H), 2.65 (dd, 1H, J=15.3, 6.4 Hz, C$_6$—H); $^{13}$C NMR (125 MHz, CDCl$_3$, 294K) δ 206.9, 178.0, 127.6, 124.1, 42.3, 40.3, 39.0; IR (neat) 2993, 2824, 1716, 1671 cm$^{-1}$; HRMS (ESI-TOF) m/z for [M+H]$^+$ C$_7$H$_9$O$_3$, calculated 141.05462, found 141.05457; melting point: 95-101° C.

Conversion of benzoic acid to 1-methyl-2,5-cyclohexadiene-1-carboxylic acid: The following procedure was performed for the conversion of benzoic acid to 1-methyl-2,5-cyclohexadiene-1-carboxylic acid:

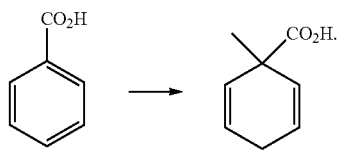

A single-neck, 100-mL round-bottom flask was equipped with a magnetic stir bar and a septum equipped with a needle connected to a bubbler as a gas outlet. Benzoic acid (1.00 g, 8.19 mmol), THF (27.0 mL), and ethylenediamine (3.28 mL, 49.1 mmol, 6.0 equivalents) were added to the flask, and the resulting mixture was cooled to 0° C. while stirring. Lithium (170 mg, 24.2 mmol, 3.0 equivalents) was added to the solution. The reaction mixture was stirred at 0° C. (external temperature) for 1 h. The color of the reaction mixture changed from clear to yellow to deep green/blue to yellow. MeI (1.27 mL, 20.5 mmol, 2.5 equivalents) was added dropwise over 5 min to the reaction mixture. A white precipitate was generated during the addition. The reaction mixture was cooled with an ice bath and acidified with concentrated HCl until pH=2. The resulting mixture was concentrated under reduced pressure with a rotary evaporator until most THF was removed. The resulting mixture was poured to a 125-mL separatory funnel, and the product was extracted with Et$_2$O (50 mL×3). The organic extracts were combined, dried over Na$_2$SO$_4$, filtered through cotton, and concentrated under reduced pressure. 1-Methoxyadamantane (0.119 g, 0.716 mmol) was added to the residue and the yield of 1-methyl-2,5-cyclohexadiene-1-carboxylic acid in the residue was determined to be 59% based on the external standard.

Data for of 1-methyl-2,5-cyclohexadiene-1-carboxylic acid: $^1$H NMR (300 MHz, CDCl$_3$, 294K) δ 5.86-5.73 (m, 4H), 2.67 (m, 2H), 1.37 (s, 3H). This data matches that known in the art (See, e.g., Yoshimi, Y. et al. Hydroxide ion as electron source for photochemical Birch-type reduction and photohalogenation. *Tetrahedron Lett.*, 2008, 49, 3400-3404).

Reduction of 1-naphthoic acid to 1,4-dihydronaphthalene-1-carboxylic acid: The following procedure was performed for the reduction of 1-naphthoic acid to 1,4-dihydronaphthalene-1-carboxylic acid:

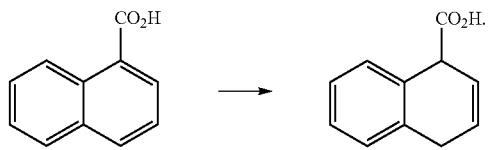 [SMILES: O=C(O)c1cccc2ccccc12 ; O=C(O)C1C=CCc2ccccc21]

A single-neck, 100-mL round-bottom flask was equipped with a magnetic stir bar and a septum equipped with a needle connected to a bubbler as a gas outlet. 1-Naphthoic acid (1.00 g, 5.81 mmol), THF (19 mL), ethylenediamine (2.33 mL, 34.9 mmol, 6.0 equivalents), and 1-methoxyadamantane (160 mg, 1.0 mmol, 0.1 equivalents, internal standard) were added to the flask, and the resulting solution was stirred while cooling to 0° C. Lithium (121 mg, 17.4 mmol, 3.0 equivalents) was added to the solution. The reaction mixture was stirred at 0° C. (external temperature) until TLC analysis showed the reaction to be complete (29 min). Saturated aqueous NH$_4$Cl (40 mL) was added to reaction mixture, and the resulting mixture was stirred until the remaining lithium was quenched. The resulting mixture was cooled with an ice bath and acidified with concentrated HCl until pH=2. The resulting mixture was concentrated under reduced pressure with a rotary evaporator until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure.

The yield of 1,4-dihydronaphthalene-1-carboxylic acid in the residue was determined to be 78% based on the internal standard.

Data for 1,4-dihydronaphthalene-1-carboxylic acid: $^1$H NMR (300 MHz, CDCl$_3$, 294K) δ 7.31-7.12 (m, 4H), 6.18 (m, 1H), 5.98 (m, 1H), 4.42 (br q, 1H, J=6.4 Hz), 3.61-3.44 (m, 1H), 3.35 (dt, 1H, J=35.7, 6.4 Hz).

Reduction of 1-naphthoic acid to 1,4,5,8-tetrahydronaphthalene-1-carboxylic acid: The following procedure was performed for the reduction of 1-naphthoic acid to 1,4,5,8-tetrahydronaphthalene-1-carboxylic acid:

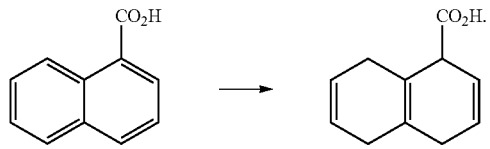 [SMILES: O=C(O)c1cccc2ccccc12 ; O=C(O)C1C=CCC2=C1CC=CC2]

A single-neck, 100-mL round-bottom flask was equipped with a magnetic stir bar and a septum equipped with a needle connected to a bubbler as a gas outlet. 1-Naphthoic acid (1.00 g, 5.81 mmol), THF (19 mL), ethylenediamine (4.65 mL, 69.7 mmol, 12.0 equivalents), and t-BuOH (1.67 mL, 17.4 mmol, 3.0 equivalents) were added to the flask, and the resulting solution was stirred while cooling to 0° C. Lithium (241 mg, 34.9 mmol, 6.0 equivalents) was added to the solution. The reaction mixture was stirred at 0° C. (external temperature) until TLC analysis showed the reaction to be complete (39 min). Saturated aqueous NH$_4$Cl (40 mL) was added to reaction mixture, and the resulting mixture was stirred until the remaining lithium was quenched. The resulting mixture was cooled with an ice bath and acidified with concentrated HCl until pH=2. The resulting mixture was concentrated under reduced pressure with a rotary evaporator until most THF was removed. The resulting mixture was poured to a 125-mL separatory funnel, and the product was extracted with EtOAc (30 mL×3). The organic extracts were combined, dried over Na$_2$SO$_4$, filtered through cotton, and concentrated under reduced pressure. The resulting solid was purified by recrystallization (5% EtOAc in hexanes) to give 1,4,5,8-tetrahydronaphthalene-1-carboxylic acid (1.26 g, 72% yield) as a white solid.

Data for 1,4,5,8-tetrahydronaphthalene-1-carboxylic acid: R$_f$=0.27 (1% AcOH and 40% EtOAc in hexanes stained with I$_2$); $^1$H NMR (300 MHz, CDCl$_3$, 296K) δ 6.04-5.91 (m, 1H), 5.84-5.74 (m, 1H, C$_6$—H), 5.74-5.65 (m, 2H), 3.58 (br d, 1H, J=4.0 Hz), 2.89-2.40 (m, 6H); $^{13}$C NMR (75 MHz, CDCl$_3$, 294K) δ 178.7, 127.6, 127.3, 124.2, 123.8, 122.1, 120.7, 47.3, 31.0, 30.9, 29.3; IR (neat) 3022, 2875, 2816, 1685 cm$^{-1}$; HRMS (ESI-TOF) m/z for [M+H]$^+$ C$_{11}$H$_{13}$O$_2$, calculated 177.09101, found 177.09114; melting point: 117-121° C.

Reduction of 2-naphthoic acid to 1,2,3,4-tetrahydronaphthalene-2-carboxylic acid: The following procedure was performed for the reduction of 2-naphthoic acid to 1,2,3,4-tetrahydronaphthalene-2-carboxylic acid:

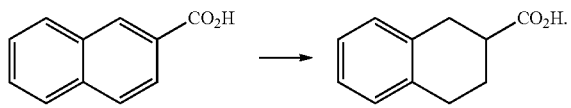 [SMILES: O=C(O)c1ccc2ccccc2c1 ; O=C(O)C1CCc2ccccc2C1]

A single-neck, 100-mL round-bottom flask was equipped with a magnetic stir bar and a septum equipped with a needle connected to a bubbler as a gas outlet. 2-Naphthoic acid (1.00 g, 5.81 mmol), THF (19 mL), ethylenediamine (3.88 mL, 58.1 mmol, 10.0 equivalents), and 1-methoxyadamantane (136 mg, 0.818 mmol, 0.1 equivalents, internal standard) were added to the flask, and the resulting solution was stirred while cooling to 0° C. Lithium (201 mg, 29.0 mmol, 5.0 equivalents) was added to the solution. The reaction mixture was stirred at 0° C. (external temperature) until TLC analysis showed the reaction to be complete (33 min). Saturated aqueous NH$_4$Cl (40 mL) was added to reaction mixture, and the resulting mixture was stirred until the remaining lithium was quenched. The resulting mixture was cooled with an ice bath and acidified with concentrated HCl until pH=2. The resulting mixture was concentrated under reduced pressure with a rotary evaporator until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The yield of 1,2,3,4-tetrahydronaphthalene-2-carboxylic acid in the residue was determined to be 59% based on the internal standard.

Data for 1,2,3,4-tetrahydronaphthalene-2-carboxylic acid: $^1$H NMR (300 MHz, CDCl$_3$, 294K) δ 7.15-7.04 (m, 4H), 3.07-2.95 (m, 2H), 2.94-2.73 (m, 3H), 2.31-2.19 (m, 1H), 1.98-1.84 (m, 1H).

Reduction of 2-naphthoic acid to 1,2,3,4,5,8-hexahydronaphthalene-2-carboxylic acid: The following procedure was performed for the reduction of 2-naphthoic acid to 1,2,3,4,5,8-hexahydronaphthalene-2-carboxylic acid:

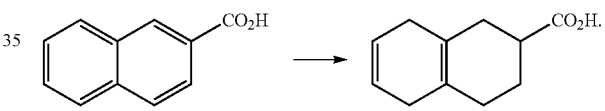

A single-neck, 100-mL round-bottom flask was equipped with a magnetic stir bar and a septum equipped with a needle connected to a bubbler as a gas outlet. 2-Naphthoic acid (1.00 g, 5.81 mmol), THF (19 mL), ethylenediamine (6.20 mL, 93.0 mmol, 16 equivalents), t-BuOH (1.67 mL, 17.4 mmol, 3.0 equivalents), and 1-methoxyadamantane (112 mg, 0.818 mmol, 0.1 equivalents, internal standard) were added to the flask, and the resulting solution was stirred while cooling to 0° C. Lithium (322 mg, 46.5 mmol, 8.0 equivalents) was added to the solution. The reaction mixture was stirred at 0° C. (external temperature) until TLC analysis showed the reaction to be complete (29 min). Saturated aqueous NH$_4$Cl (40 mL) was added to reaction mixture, and the resulting mixture was stirred until the remaining lithium was quenched. The resulting mixture was cooled with an ice bath and acidified with concentrated HCl until pH=2. The resulting mixture was concentrated under reduced pressure with a rotary evaporator until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The yield of 1,2,3,4,5,8-hexahydronaphthalene-2-carboxylic acid in the residue was determined to be 65% based on the internal standard.

Data for 1,2,3,4,5,8-hexahydronaphthalene-2-carboxylic acid: $^1$H NMR (300 MHz, CDCl$_3$, 294K) δ 5.71 (s, 2H), 2.62-2.46 (m, 4H), 2.18-1.92 (m, 7H).

Reduction of hydrocinnamic acid to 3-(1,4-cyclohexadien-1-yl)propanoic acid: The following procedure was performed for the reduction of hydrocinnamic acid to 3-(1,4-cyclohexadien-1-yl)propanoic acid:

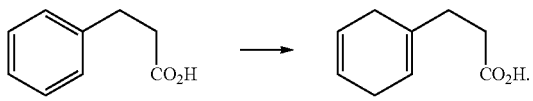 [SMILES: O=C(O)CCc1ccccc1 ; O=C(O)CCC1=CCC=CC1]

A single-neck, 100-mL round-bottom flask was equipped with a magnetic stir bar and a septum equipped with a needle connected to a bubbler as a gas outlet. Hydrocinnamic acid (1.00 g, 6.66 mmol), THF (22 mL), ethylenediamine (4.45 mL, 66.6 mmol, 10 equivalents), t-BuOH (1.27 mL, 13.3 mmol, 2.0 equivalents), and 1-methoxyadamantane (148 mg, 0.890 mmol) were added to the flask, and the resulting solution was stirred while cooling to 0° C. Lithium (231 mg, 33.3 mmol, 5.0 equivalents) was added to the solution. The reaction mixture was stirred at 0° C. (external temperature) until TLC analysis showed the reaction to be complete (30 min). Saturated aqueous $NH_4Cl$ (40 mL) was added to reaction mixture, and the resulting mixture was stirred until the remaining lithium was quenched. The resulting mixture was cooled with an ice bath and acidified with concentrated HCl until pH=2. The resulting mixture was concentrated under reduced pressure with a rotary evaporator until most THF was removed. The resulting mixture was poured to a 125-mL separatory funnel, and the product was extracted with $Et_2O$ (30 mL×3). The organic extracts were combined, dried over $Na_2SO_4$, filtered through cotton, and concentrated under reduced pressure. The yield of 3-(1,4-cyclohexadien-1-yl)propanoic acid in the residue was determined to be 72% based on the internal standard.

Data for 3-(1,4-cyclohexadien-1-yl)propanoic acid: $^1$H NMR (300 MHz, $CDCl_3$, 294K) δ 5.70 (br s, 2H), 5.46 (br s, 1H), 2.73-2.56 (m, 4H), 2.55-2.42 (m, 2H), 2.30 (t, 2H, J=7.6 Hz).

Reduction of N-(tert-butoxycarbonyl)-L-phenylalanine to (S)-2-((tert-butoxycarbonyl)amino)-3-(1,4-cyclohexadien-1-yl)propanoic acid: The following procedure was performed for the reduction of N-(tert-butoxycarbonyl)-L-phenylalanine to (S)-2-((tert-butoxycarbonyl)amino)-3-(1,4-cyclohexadien-1-yl)propanoic acid:

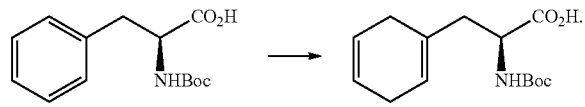 [SMILES: CC(C)(C)OC(=O)N[C@@H](Cc1ccccc1)C(=O)O ; CC(C)(C)OC(=O)N[C@@H](CC1=CCC=CC1)C(=O)O]

A single-neck, 100-mL round-bottom flask was equipped with a magnetic stir bar and a septum equipped with a needle connected to a bubbler as a gas outlet. N-(tert-Butoxycarbonyl)-L-phenylalanine (1.00 g, 3.77 mmol), THF (13 mL), ethylenediamine (2.52 mL, 37.7 mmol, 10.0 equivalents), and t-BuOH (1.08 mL, 11.3 mmol, 3.0 equivalents) were added to the flask, and the resulting solution was stirred while cooling to 0° C. Lithium (131 mg, 18.9 mmol, 5.0 equivalents) was added to the solution. The reaction mixture was stirred at 0° C. (external temperature) until TLC analysis showed the reaction to be complete (30 min). Saturated aqueous $NH_4Cl$ (40 mL) was added to reaction mixture, and the resulting mixture was stirred until the remaining lithium was quenched. The resulting mixture was cooled with an ice bath and acidified with o-phosphoric acid until pH=3-4. The resulting mixture was concentrated under reduced pressure with a rotary evaporator until most THF was removed. The resulting mixture was poured to a 125-mL separatory funnel, and the product was extracted with $Et_2O$ (30 mL×3). The organic extracts were combined, dried over $Na_2SO_4$, filtered through cotton, and concentrated under reduced pressure. The resulting residue was purified by flash column chromatography ($SiO_2$, 5 to 50% EtOAc in hexanes with 1% acetic acid) to give (S)-2-((tert-butoxycarbonyl)amino)-3-(1,4-cyclohexadien-1-yl)propanoic acid (551 mg, 54% yield) as a viscous, colorless oil.

Data for (S)-2-((tert-butoxycarbonyl)amino)-3-(1,4-cyclohexadien-1-yl)propanoic acid: $R_f$=0.47 (1% AcOH and 60% EtOAc in hexanes stained with $I_2$); $^1$H NMR (400 MHz, $CDCl_3$, 294K) δ 5.74-5.64 (br t, 2H, J=12.3 Hz), 5.54 (br s, 1H), 4.92 (d, 1H, J=7.2 Hz), 4.44-4.29 (m, 1H), 2.78-2.49 (m, 4H), 2.41-2.27 (m, 1H), 1.80-1.67 (m, 1H), 1.44 (s, 9H); $^{13}$C NMR (100 MHz, $CDCl_3$, 294K) δ 177.3, 155.7, 129.9, 128.6, 123.9, 123.4, 80.4, 51.6, 40.1, 34.8, 28.5, 28.3; IR (neat) 3324, 3034, 2978, 2926, 1716, 1395, 1163 $cm^{-1}$; HRMS (ESI-TOF) m/z for [M−H]$^-$ $C_{14}H_{12}O_4N$, calcd 266.13868, found 266.13885.

Reduction of n-butoxybenzene to 1-butoxy-1,4-cyclohexadiene: The following procedure was performed for the reduction of n-butoxybenzene to 1-butoxy-1,4-cyclohexadiene:

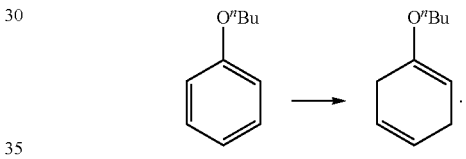

A single-neck, 100-mL round-bottom flask was equipped with a magnetic stir bar and a septum equipped with a needle connected to a bubbler as a gas outlet. n-Butoxybenzene (4.50 g, 30.0 mmol), THF (26 mL), ethylenediamine (12.0 mL, 180 mmol, 6.0 equivalents), and t-BuOH (7.16 mL, 75.0 mmol, 2.5 equivalents) were added to the flask, and the resulting solution was cooled to 0° C. while stirring. Lithium (624 mg, 89.9 mmol, 3.0 equivalents) was added to the solution. The reaction mixture was stirred at 0° C. (external temperature) until TLC analysis showed the reaction to be complete (30 min). Saturated aqueous $NH_4Cl$ (40 mL) was added to the reaction mixture, and the resulting mixture was stirred until the remaining lithium was quenched. The resulting mixture was concentrated under reduced pressure with a rotary evaporator until most THF was removed. The resulting mixture was poured to a 125-mL separatory funnel, and the product was extracted with $Et_2O$ (30 mL×3). The organic extracts were combined, dried over $Na_2SO_4$, filtered through cotton, and concentrated under reduced pressure. The resulting residue was purified by flash column chromatography ($SiO_2$, 0.25 to 2% EtOAc in hexanes) to give 1-butoxy-1,4-cyclohexadiene (3.82 g, 85% yield) as a colorless oil.

Data for 1-butoxy-1,4-cyclohexadiene: $R_f$=0.51 (1% EtOAc in hexanes, $I_2$); $^1$H NMR (300 MHz, $CDCl_3$, 294K) δ 5.68 (br t, 2H, J=11.5 Hz), 4.61 (br s, 1H), 3.68 (t, 2H, J=6.5 Hz), 2.85-2.75 (m, 2H), 2.75-2.66 (m, 2H), 1.65 (br quint, 2H, J=7.6 Hz), 1.42 (sextet, 2H, J=7.6 Hz), 0.94 (t, 3H, J=7.5 Hz); $^{13}$C NMR (100 MHz, $CDCl_3$, 294K) δ 152.1, 124.6, 123.3, 91.0, 65.9, 31.2, 28.7, 26.4, 19.4, 13.9; HRMS (ESI-TOF) m/z for [M+H]$^+$ $C_{10}H_{17}O$, calculated 153.12739, found 153.12743.

Reduction of 2-methylanisole to 1-methoxy-2-methyl-1,4-cyclohexadiene: The following procedure was performed for the reduction of 2-methylanisole to 1-methoxy-2-methyl-1,4-cyclohexadiene:

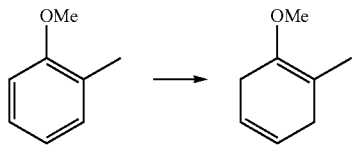

A single-neck, 100-mL round-bottom flask was equipped with a magnetic stir bar and a septum equipped with a needle connected to a bubbler as a gas outlet. 2-Methylanisole (1.00 g, 8.19 mmol), THF (27 mL), ethylenediamine (3.28 mL, 49.1 mmol, 6.0 equivalents), t-BuOH (1.96 mL, 20.4 mmol, 2.5 equivalents), and 1-methoxyadamantane (166 mg, 0.998 mmol, 0.1 equivalents, internal standard) were added to the flask, and the resulting solution was stirred while cooling to 0° C. Lithium (170 mg, 24.6 mmol, 2.5 equivalents) was added to the solution. The reaction mixture was stirred at 0° C. (external temperature) until TLC analysis showed the reaction to be complete (20 min). Saturated aqueous NH$_4$Cl (40 mL) was added to reaction mixture, and the resulting mixture was stirred until the remaining lithium was quenched. The resulting mixture was concentrated under reduced pressure with a rotary evaporator and the water bath at 25° C. until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The yield of 1-methoxy-2-methyl-1,4-cyclohexadiene in the residue was determined to be 69% based on the internal standard.

Data for 1-methoxy-2-methyl-1,4-cyclohexadiene: $^1$H NMR (300 MHz, CDCl$_3$, 294K) δ 5.72-5.58 (m, 2H), 3.53 (s, 3H), 2.85-2.74 (m, 2H), 2.74-2.63 (m, 2H), 1.64 (s, 3H).

Reduction of 3-methylanisole to 1-methoxy-5-methyl-1,4-cyclohexadiene: The following procedure was performed for the reduction of 3-methylanisole to 1-methoxy-5-methyl-1,4-cyclohexadiene:

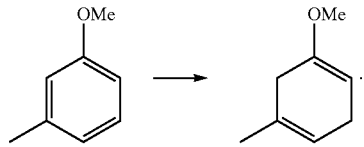

A single-neck, 100-mL round-bottom flask was equipped with a magnetic stir bar and a septum equipped with a needle connected to a bubbler as a gas outlet. 3-Methylanisole (1.00 g, 8.19 mmol), THF (27 mL), ethylenediamine (3.28 mL, 49.1 mmol, 6.0 equivalents), t-BuOH (1.96 mL, 20.4 mmol, 2.5 equivalents), and 1-methoxyadamantane (166 mg, 0.998 mmol, 0.1 equivalents, internal standard) were added to the flask, and the resulting solution was stirred while cooling to 0° C. Lithium (170 mg, 24.6 mmol, 2.5 equivalents) was added to the solution. The reaction mixture was stirred at 0° C. (external temperature) until TLC analysis showed the reaction to be complete (20 min). Saturated aqueous NH$_4$Cl (40 mL) was added to reaction mixture, and the resulting mixture was stirred until the remaining lithium was quenched. The resulting mixture was concentrated under reduced pressure with a rotary evaporator and the water bath at 25° C. until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The yield of 1-methoxy-5-methyl-1,4-cyclohexadiene in the residue was determined to be 63% based on the internal standard.

Data for 1-methoxy-5-methyl-1,4-cyclohexadiene: $^1$H NMR (300 MHz, CDCl$_3$, 294K) δ 5.41 (br s, 1H), 4.64 (br s, 1H), 3.56 (s, 3H), 2.84-2.72 (m, 2H), 2.61 (t, 2H, J=7.6 Hz), 1.70 (s, 3H).

Reduction of 4-methylanisole to 1-methoxy-4-methyl-1,4-cyclohexadiene: The following procedure was performed for the reduction of 4-methylanisole to 1-methoxy-4-methyl-1,4-cyclohexadiene:

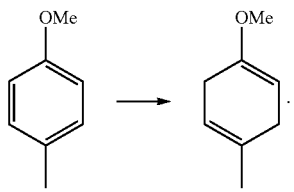

A single-neck, 100-mL round-bottom flask was equipped with a magnetic stir bar and a septum equipped with a needle connected to a bubbler as a gas outlet. 4-Methylanisole (1.00 g, 8.19 mmol), THF (27 mL), ethylenediamine (3.28 mL, 49.1 mmol, 6.0 equivalents), t-BuOH (1.96 mL, 20.4 mmol, 2.5 equivalents), and 1-methoxyadamantane (166 mg, 0.998 mmol, 0.1 equivalents, internal standard) were added to the flask, and the resulting solution was stirred while cooling to 0° C. Lithium (170 mg, 24.6 mmol, 2.5 equivalents) was added to the solution. The reaction mixture was stirred at 0° C. (external temperature) until TLC analysis showed the reaction to be complete (20 min). Saturated aqueous NH$_4$Cl (40 mL) was added to reaction mixture, and the resulting mixture was stirred until the remaining lithium was quenched. The resulting mixture was concentrated under reduced pressure with a rotary evaporator and the water bath at 25° C. until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The yield of 1-methoxy-4-methyl-1,4-cyclohexadiene in the residue was determined to be 75% based on the internal standard.

Data for 1-methoxy-4-methyl-1,4-cyclohexadiene: $^1$H NMR (300 MHz, CDCl$_3$, 294K) δ 5.35 (br s, 1H), 4.61 (br s, 1H), 3.54 (s, 3H), 2.69 (br s, 4H), 1.68 (s, 3H).

Conversion of p-cresol to t-butyldimethyl(p-tolyloxy)silane: The following procedure was performed for the conversion of p-cresol to t-butyldimethyl(p-tolyloxy)silane:

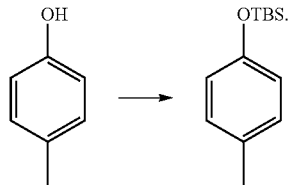

A single-neck, 1000-mL round-bottom flask was equipped with a magnetic stir bar and a septum equipped with a needle connected to a nitrogen inlet. p-cresol (10.0 g, 92.5 mmol), Et₃N (19.3 mL, 139 mmol, 1.5 equivalents), DMAP (2.26 g, 18.5 mmol, 0.2 equivalents), and CH₂Cl₂ (300 mL) were added to the flask. TBSCl (16.7 g, 111 mmol, 1.2 equivalents) was added to the solution, and the reaction mixture was stirred at 25° C. for 16 h. Water (100 mL) was added to reaction mixture. The resulting mixture was poured to a 500-mL separatory funnel. The layers were separated. The organic layer was washed with water (100 mL) and brine (100 mL). The organic extract was dried over Na₂SO₄, filtered through cotton, and concentrated under reduced pressure. The residue was distilled under reduced pressure (~10 mmHg, boiling point: 67° C.) to give a colorless oil. The resulting colorless oil was passed through a plug of silica gel, eluting with 10% EtOAc in hexanes. The resulting filtrate was concentrated under reduced pressure with a rotary evaporator to give t-butyldimethyl(p-tolyloxy)silane as a clear oil (14.6 g, 71% yield).

Data for t-butyldimethyl(p-tolyloxy)silane: ¹H NMR (300 MHz, CDCl₃, 294K) δ 7.02 (d, 2H, J=8.1 Hz), 6.73 (dd, 2H, J=8.1, 1.7 Hz), 2.28 (s, 3H), 0.98 (s, 9H), 0.18 (s, 6H).

Reduction of t-butyldimethyl(p-tolyloxy)silane to t-butyldimethyl((4-methyl-1,4-cyclohexadien-1-yl)oxy)silane: The following procedure was performed for the reduction of t-butyldimethyl(p-tolyloxy)silane to t-butyldimethyl((4-methyl-1,4-cyclohexadien-1-yl)oxy)silane:

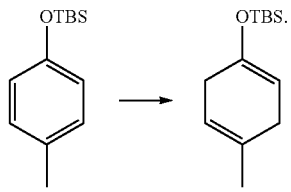

A single-neck, 100-mL round-bottom flask was equipped with a magnetic stir bar and a septum equipped with a needle connected to a bubbler as a gas outlet. t-Butyldimethyl(p-tolyloxy)silane (1.00 g, 4.50 mmol), THF (15 mL), ethylenediamine (1.80 mL, 27.0 mmol, 6.0 equivalents), t-BuOH (1.08 mL, 11.2 mmol, 2.5 equivalents), and 1-methoxyadamantane (86.0 mg, 0.450 mmol, 0.1 equivalents, internal standard) were added to the flask, and the resulting solution was stirred while cooling to 0° C. Lithium (94.0 mg, 13.5 mmol, 3.0 equivalents) was added to the solution. The reaction mixture was stirred at 0° C. (external temperature) until TLC analysis showed the reaction to be complete (20 min). Saturated aqueous NH₄Cl (40 mL) was added to reaction mixture, and the resulting mixture was stirred until the remaining lithium was quenched. The resulting mixture was concentrated under reduced pressure with a rotary evaporator and the water bath at 25° C. until most THF was removed. The resulting mixture was poured to a 125-mL separatory funnel, and the product was extracted with Et₂O (30 mL×3). The organic extracts were combined, dried over Na₂SO₄, filtered through cotton, and concentrated under reduced pressure. The yield of t-butyldimethyl((4-methyl-1,4-cyclohexadien-1-yl)oxy)silane in the residue was determined to be 75% based on the internal standard.

Data for of t-butyldimethyl((4-methyl-1,4-cyclohexadien-1-yl)oxy)silane: ¹H NMR (300 MHz, CDCl₃, 294K) δ 5.33 (br s, 1H), 4.83 (br s, 1H), 2.64 (br s, 4H), 1.67 (s, 3H) 0.92 (s, 9H), 0.14 (s, 6H).

The prior art demonstrates the industrial application of the reduction of t-butyldimethyl(p-tolyloxy)silane to form t-butyldimethyl((4-methyl-1,4-cyclohexadien-1-yl)oxy)silane in 74% yield after 16 hours in batch (See, for example, Peters, B. K. et al. Scalable and safe synthetic organic electroreduction inspired by Li-ion battery chemistry. Science, 2019, 363, 838-845). The current method produced the same product on a similar scale in 75% yield after 30 minutes.

Reduction of 6-methoxy-1,2,3,4-tetra-hydronaphthalene to 6-methoxy-1,2,3,4,5,8-hexahydronaphthalene: The following procedure was performed for the reduction of 6-methoxy-1,2,3,4-tetra-hydronaphthalene to 6-methoxy-1,2,3,4,5,8-hexahydro naphthalene:

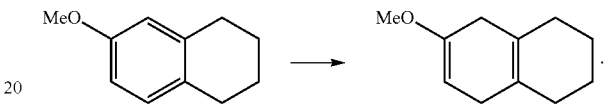

A single-neck, 100-mL round-bottom flask was equipped with a magnetic stir bar and a septum equipped with a needle connected to a bubbler as a gas outlet. 6-Methoxy-1,2,3,4-tetrahydronaphthalene (1.00 g, 6.16 mmol), THF (21 mL), ethylenediamine (2.47 mL, 37.0 mmol, 6.0 equivalents), t-BuOH (1.47 mL, 15.4 mmol, 2.5 equivalents), and 1-methoxyadamantane (136 mg, 0.818 mmol, 0.1 equivalents, internal standard) were added to the flask, and the resulting solution was stirred while cooling to 0° C. Lithium (128 mg, 18.5 mmol, 3.0 equivalents) was added to the solution. The reaction mixture was stirred at 0° C. (external temperature) until TLC analysis showed the reaction to be complete (20 min). Saturated aqueous NH₄Cl (40 mL) was added to reaction mixture, and the resulting mixture was stirred until the remaining lithium was quenched. The resulting mixture was concentrated under reduced pressure with a rotary evaporator and the water bath at 25° C. until most THF was removed. The resulting mixture was poured to a 125-mL separatory funnel, and the product was extracted with Et₂O (30 mL×3). The organic extracts were combined, dried over Na₂SO₄, filtered through cotton, and concentrated under reduced pressure. The yield of 6-methoxy-1,2,3,4,5,8-hexahydronaphthalene in the residue was determined to be 78% based on the internal standard.

Data for 6-methoxy-1,2,3,4,5,8-hexahydronaphthalene: ¹H NMR (300 MHz, CDCl₃, 294K) δ 4.65 (t, 1H, J=3.4 Hz), 3.55 (s, 3H), 2.72-2.62 (m, 2H), 2.62-2.52 (m, 2H), 1.96-1.86 (m, 4H), 1.67-1.60 (m, 4H).

Reduction of 5-indanol to 5-methoxy-2,3-dihydro-1H-indene: The following procedure was performed for the reduction of 5-indanol to 5-methoxy-2,3-dihydro-1H-indene:

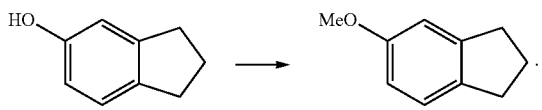 [SMILES: Oc1ccc2c(c1)CCC2 ; COc1ccc2c(c1)CCC2]

A single-neck, 100-mL round-bottom flask was equipped with a magnetic stir bar and a septum equipped with a needle connected to a nitrogen inlet. 5-Indanol (5.00 g, 37.2 mmol), K₂CO₃ (8.24 g, 59.6 mmol, 1.6 equivalents), MeI (3.48 mL, 55.9 mmol, 1.5 equivalents), and DMF (28.0 mL) were added to the flask. The resulting solution was heated to 55°

C. (external temperature) and left to stir for 16 h. The reaction mixture was cooled to room temperature, poured to a 250-mL separatory funnel, and diluted with Et$_2$O (60 mL) and water (80 mL). The layers were separated, and the aqueous solution was extracted with Et$_2$O (30 mL×2). The organic extracts were combined and washed with saturated aqueous NaHCO$_3$ (40 mL), 1M NaOH (40 mL), and water (40 mL). The organic extracts were dried over Na$_2$SO$_4$, filtered through cotton, and concentrated under reduced pressure. The resulting residue was purified by flash column chromatography (SiO$_2$, 1 to 4% EtOAc in hexanes) to give 5-methoxy-2,3-dihydro-1H-indene (5.61 g, 97% yield) as a colorless oil.

Data for 5-methoxy-2,3-dihydro-1H-indene: $^1$H NMR (300 MHz, CDCl$_3$, 294K) δ 7.12 (d, 1H, J=8.2 Hz), 6.79 (br s, 1H), 6.69 (dd, 1H, J=8.2, 2.3 Hz), 3.78 (s, 3H), 2.86 (overlap dt, 4H, J=13.7, 7.4 Hz), 2.07 (quint, 2H, J=7.4 Hz).

Reduction of 5-methoxy-2,3-dihydro-1H-indene to 5-methoxy-2,3,4,7-tetrahydro-1H-indene: The following procedure was performed for the reduction of 5-methoxy-2,3-dihydro-1H-indene to 5-methoxy-2,3,4,7-tetrahydro-1H-indene:

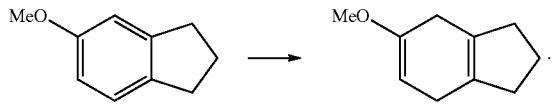 [SMILES: COc1ccc2c(c1)CCC2 ; COC1=CCC2=C(CCC2)C1]

A single-neck, 100-mL round-bottom flask was equipped with a magnetic stir bar and a septum equipped with a needle connected to a bubbler as a gas outlet. 5-Methoxy-2,3-dihydro-1H-indene (1.00 g, 6.75 mmol), THF (22 mL), ethylenediamine (2.70 mL, 40.5 mmol, 6.0 equivalents), t-BuOH (1.61 mL, 16.9 mmol, 2.5 equivalents), and 1-methoxyadamantane (140 mg, 0.818 mmol, 0.1 equivalents, internal standard) were added to the flask, and the resulting solution was stirred while cooling to 0° C. Lithium (140 mg, 20.2 mmol, 3.0 equivalents) was added to the solution. The reaction mixture was stirred at 0° C. (external temperature) until TLC analysis showed the reaction to be complete (15 min). Saturated aqueous NH$_4$Cl (40 mL) was added to reaction mixture, and the resulting mixture was stirred until the remaining lithium was quenched. The resulting mixture was concentrated under reduced pressure with a rotary evaporator and the water bath at 25° C. until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The yield of 5-methoxy-2,3,4,7-tetrahydro-1H-indene in the residue was determined to be 81% based on the internal standard.

Data for 5-methoxy-2,3,4,7-tetrahydro-1H-indene: $^1$H NMR (300 MHz, CDCl$_3$, 294K) δ 4.68 (br s, 1H), 3.57 (s, 3H), 2.80-2.63 (m, 4H), 2.28 (br t, 4H, J=7.4 Hz), 1.90 (br quint, 2H, J=7.4 Hz).

Reduction of dextromethorphan to (4bS,9S)-3-methoxy-11-methyl-4,5,6,7,8,8a,9,10-octahydro-1H-9,4b-(epiminoethano)phenanthrene: The following procedure was performed for the reduction of dextromethorphan to (4bS,9S)-3-methoxy-11-methyl-4,5,6,7,8,8a,9,10-octahydro-1H-9,4b-(epiminoethano)phenanthrene:

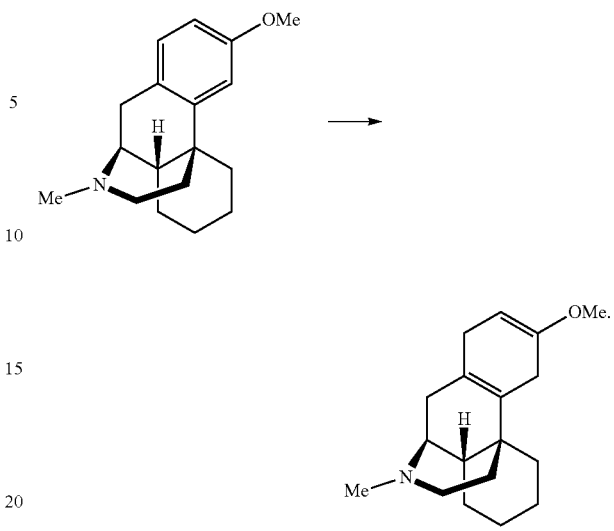

A single-neck, 100-mL round-bottom flask was equipped with a magnetic stir bar and a septum equipped with a needle connected to a bubbler as a gas outlet. Dextromethorphan hydrobromide (1.00 g, 2.70 mmol), THF (9.0 mL), ethylenediamine (1.80 mL, 27.0 mmol, 10 equivalents), t-BuOH (0.775 mL, 8.16 mmol, 3.0 equivalents), and 1-methoxyadamantane (86.0 mg, 0.352 mmol, 0.1 equivalents, internal standard) were added to the flask, and the resulting solution was stirred while cooling to 0° C. Lithium (94.0 mg, 13.5 mmol, 5.0 equivalents) was added to the solution. The reaction mixture was stirred at 0° C. (external temperature) for 5 min. When TLC analysis showed the reaction to be incomplete, the reaction mixture was allowed to stir at 25° C. (external temperature) until TLC analysis showed the reaction to be complete (35 min). Saturated aqueous NH$_4$Cl (40 mL) was added to reaction mixture, and the resulting mixture was stirred until the remaining lithium was quenched. The resulting mixture was concentrated under reduced pressure with a rotary evaporator until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The yield of (4bS,9S)-3-methoxy-11-methyl-4,5,6,7,8,8a,9,10-octahydro-1H-9,4b-(epiminoethano) phenanthrene in the residue was determined to be 54% based on the internal standard.

Data for (4bS,9S)-3-methoxy-11-methyl-4,5,6,7,8,8a,9,10-octahydro-1H-9,4b-(epiminoethano)phenanthrene: $^1$H NMR (300 MHz, CDCl$_3$, 294K) δ 4.59 (br s, 1H), 3.53 (s, 3H), 2.77-2.66 (m, 2H), 2.66-2.54 (m, 2H), 2.54-2.41 (m, 3H), 2.33 (s, 3H), 2.04 (dd, 1H, J=18.2, 8.7 Hz), 1.89-1.85 (m, 2H), 1.71-1.65 (m, 2H), 1.59-1.52 (m, 2H), 1.48-1.34 (m, 6H), 1.02 (dd, 1H, J=13.4, 3.2 Hz).

Reduction of estradiol 3-methyl ether to (8R,9S,13S,14S)-3-methoxy-13-methyl-4,6,7,8,9,11,12,13,14,15,16,17-dodecahydro-1H-cyclopenta[a]phenanthren-17-ol: The following procedure was performed for the reduction of estradiol 3-methyl ether to (8R,9S,13S,14S)-3-methoxy-13-methyl-4,6,7,8,9,11,12,13,14,15,16,17-dodecahydro-1H-cyclopenta[a]phenanthren-17-ol:

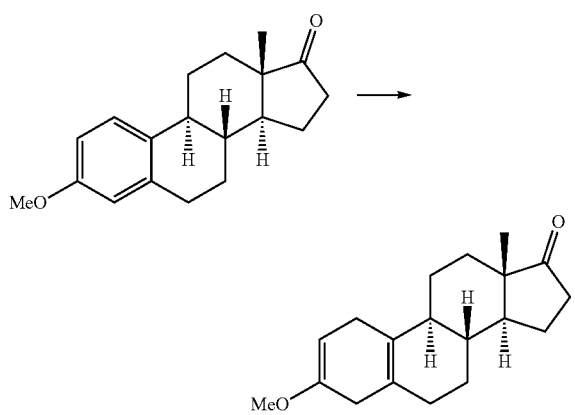

A single-neck, 100-mL round-bottom flask was equipped with a magnetic stir bar and a septum equipped with a needle connected to a bubbler as a gas outlet. Estradiol 3-methyl ether (0.980 g, 3.52 mmol), THF (12 mL), ethylenediamine (2.35 mL, 35.2 mmol, 10 equivalents), t-BuOH (1.01 mL, 10.6 mmol, 3.0 equivalents), and 1-methoxyadamantane (86.0 mg, 0.352 mmol, 0.1 equivalents, internal standard) were added to the flask, and the resulting solution was stirred while cooling to 0° C. Lithium (122 mg, 17.6 mmol, 5.0 equivalents) was added to the solution. The reaction mixture was stirred at 0° C. (external temperature) until TLC analysis showed the reaction to be complete (30 min). Saturated aqueous NH$_4$Cl (40 mL) was added to reaction mixture, and the resulting mixture was stirred until the remaining lithium was quenched. The resulting mixture was concentrated under reduced pressure with a rotary evaporator until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The yield of (8R,9S,13S,14S)-3-methoxy-13-methyl-4,6,7,8,9,11,12,13,14,15,16,17-dodecahydro-1H-cyclopenta[a]phenanthren-17-ol in the residue was determined to be 56% based on the internal standard.

Data for (8R,9S,13S,14S)-3-methoxy-13-methyl-4,6,7,8,9,11,12,13,14,15,16,17-dodecahydro-M-cyclopenta[a]phenanthren-17-ol: $^1$H NMR (300 MHz, CDCl$_3$, 294K) δ 4.64 (br s, 1H), 3.68 (t, 1H, J=8.4 Hz), 3.55 (s, 3H), 2.97-2.79 (m, 1H), 2.79-2.40 (m, 4H), 2.13-2.00 (m, 2H), 2.00-1.79 (m, 3H), 1.77-1.56 (m, 3H), 1.55-1.00 (m, 8H), 0.77 (s, 3H).

Reduction of 2-(o-tolyl)ethanol to 2-(2-methyl-1,4-cyclohexadien-1-yl)ethan-1-ol: The following procedure was performed for the reduction of 2-(o-tolyl)ethanol to 2-(2-methyl-1,4-cyclohexadien-1-yl)ethan-1-ol:

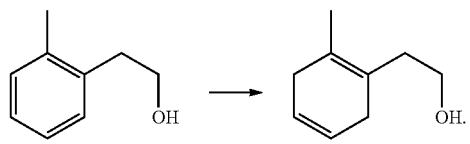

A single-neck, 100-mL round-bottom flask was equipped with a magnetic stir bar and a septum equipped with a needle connected to a bubbler as a gas outlet. 2-(o-Tolyl)ethanol (1.00 g, 7.34 mmol), THF (24 mL), ethylenediamine (4.90 mL, 73.4 mmol, 10 equivalents), t-BuOH (1.05 mL, 11.0 mmol, 1.5 equivalents), and 1-methoxyadamantane (136 mg, 0.818 mmol, 0.1 equivalents, internal standard) were added to the flask, and the resulting solution was stirred while cooling to 0° C. Lithium (255 mg, 36.7 mmol, 5.0 equivalents) was added to the solution. The reaction mixture was stirred at 0° C. (external temperature) until TLC analysis showed the reaction to be complete (20 min). Saturated aqueous NH$_4$Cl (40 mL) was added to reaction mixture, and the resulting mixture was stirred until the remaining lithium was quenched. The resulting mixture was concentrated under reduced pressure with a rotary evaporator and the water bath at 25° C. until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The yield of 2-(2-methyl-1,4-cyclohexadien-1-yl)ethan-1-ol in the residue was determined to be 64% based on the internal standard.

Data for 2-(2-methyl-1,4-cyclohexadien-1-yl)ethan-1-ol: $^1$H NMR (300 MHz, CDCl$_3$, 294K) δ 5.69 (br d, 2H, J=1.2 Hz), 3.67 (br t, 2H, J=6.8 Hz), 2.70-2.57 (m, 4H), 2.35 (t, 2H, J=6.8 Hz), 1.69 (s, 3H).

Reduction of naphthalene to 1,4,5,8-tetrahydronaphthalene: The following procedure was performed for the reduction of naphthalene to 1,4,5,8-tetrahydronaphthalene:

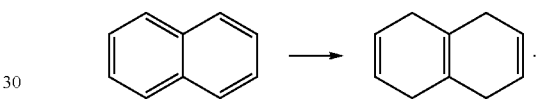

A single-neck, 100-mL round-bottom flask was equipped with a magnetic stir bar and a septum equipped with a needle connected to a bubbler as a gas outlet. Naphthalene (1.00 g, 7.80 mmol), THF (26 mL), ethylenediamine (5.21 mL, 78.0 mmol, 10 equivalents), and t-BuOH (2.24 mL, 23.4 mmol, 3.0 equivalents) were added to the flask, and the resulting solution was stirred while cooling to 0° C. Lithium (271 mg, 39.0 mol, 5.0 equivalents) was added to the solution. The reaction mixture was stirred at 0° C. (external temperature) until TLC analysis showed the reaction to be complete (33 min). Saturated aqueous NH$_4$Cl (40 mL) was added to reaction mixture, and the resulting solution was stirred until the remaining lithium was quenched. The resulting mixture was concentrated under reduced pressure with a rotary evaporator until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The resulting residue was purified by flash column chromatography (SiO$_2$, 5 to 10% EtOAc in hexanes) to give 1,4,5,8-tetrahydronaphthalene (966 mg, 96% yield) as a colorless solid.

Data for 1,4,5,8-tetrahydronaphthalene: $^1$H NMR (300 MHz, CDCl$_3$, 294K) δ 5.73 (s, 4H), 2.54 (s, 8H).

Reduction of benzylamine to 1,4-cyclohexadien-1-yl-methanamine: The following procedure was performed for the reduction of benzylamine to 1,4-cyclohexadien-1-yl-methanamine:

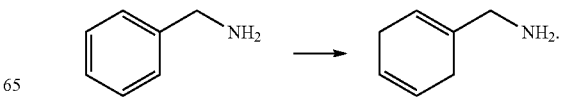

A single-neck, 100-mL round-bottom flask was equipped with a magnetic stir bar and a septum equipped with a needle connected to a bubbler as a gas outlet. Benzylamine (1.00 g, 9.33 mmol), THF (30 mL), ethylenediamine (3.74 mL, 56.0 mmol, 6.0 equivalents), and t-BuOH (1.34 mL, 14.0 mmol, 1.5 equivalents) were added to the flask, and the resulting solution was stirred while cooling to 0° C. Lithium (194 mg, 36.7 mmol, 3.0 equivalents) was added to the solution. The reaction mixture was stirred at 0° C. (external temperature) until TLC analysis showed the reaction to be complete (26 min). Saturated aqueous NH$_4$Cl (40 mL) was added to reaction mixture (CAUTION: Evolution of hydrogen gas), and the resulting mixture was stirred until the remaining lithium was quenched. The resulting mixture was concentrated under reduced pressure with a rotary evaporator and the water bath at 25° C. until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The oil was determined to be pure by $^1$H NMR spectroscopy to give 1,4-cyclohexadien-1-ylmethanamine (530 mg, 52% yield) as a yellow oil.

Data for 1,4-cyclohexadien-1-ylmethanamine: R$_f$=0.35 (10% MeOH in CH$_2$Cl$_2$, I$_2$); $^1$H NMR (400 MHz, CDCl$_3$, 294K) δ 5.79-5.63 (br s, 2H), 5.57 (br s, 1H), 3.16 (s, 2H), 2.69 (app d, 2H, J=5.5 Hz), 2.63 (app d, 2H, J=9.9 Hz), 1.32 (br s, 2H); $^{13}$C NMR (100 MHz, CDCl$_3$, 294K) δ 136.4, 124.3, 124.0, 117.8, 48.1, 27.4, 26.5; IR (neat) 3375, 3290, 3025, 2819, 1428 cm$^{-1}$; HRMS (ESI-TOF) m/z for [M+H]$^+$ C$_7$H$_{12}$N, calculated 110.0964, found 110.0966.

Reduction of benzylamine to 2-(1,4-cyclohexadien-1-yl)ethan-1-amine: The following procedure was performed for the reduction of benzylamine to 2-(1,4-cyclohexadien-1-yl)ethan-1-amine:

A single-neck, 100-mL round-bottom flask was equipped with a magnetic stir bar and a septum equipped with a needle connected to a bubbler as a gas outlet. Phenethylamine (1.00 g, 8.21 mmol), THF (27 mL), ethylenediamine (3.29 mL, 49.3 mmol, 6.0 equivalents), and t-BuOH (1.18 mL, 12.3 mmol, 1.5 equivalents) were added to the flask, and the resulting solution was stirred while cooling to 0° C. Lithium (171 mg, 24.6 mmol, 3.0 equivalents) was added to the solution. The reaction mixture was stirred at 0° C. (external temperature) until TLC analysis showed the reaction to be complete (20 min). Saturated aqueous NH$_4$Cl (40 mL) was added to reaction mixture (CAUTION: Evolution of hydrogen gas), and the resulting mixture was stirred until the remaining lithium was quenched. The resulting mixture was concentrated under reduced pressure with a rotary evaporator and the water bath at 25° C. until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The oil was determined to be pure by $^1$H NMR spectroscopy to give 2-(1,4-cyclohexadien-1-yl)ethan-1-amine (815 mg, 80% yield) as a yellow oil.

Data for 2-(1,4-cyclohexadien-1-yl)ethan-1-amine: R$_f$=0.53 (10% MeOH in CH$_2$Cl$_2$, I$_2$); $^1$H NMR (400 MHz, CDCl$_3$, 294K) δ 5.70 (app t, 2H, J=11.9 Hz), 5.48 (app s, 1H), 2.77 (t, 2H, J=6.8), 2.74-2.66 (m, 2H), 2.58 (app t, 2H, J=8.7 Hz), 2.11 (t, 2H, J=6.8 Hz), 1.28 (br s, 2H); $^{13}$C NMR (100 MHz, CDCl$_3$, 294K) δ 132.4, 124.3, 124.2, 120.4, 41.6, 39.6, 28.7, 26.8; IR (neat) 3366, 3291, 3025, 2819, 1429 cm$^{-1}$; HRMS (ESI-TOF) m/z for [M+H]$^+$ C$_8$H$_{14}$N, calculated 124.1121, found 124.1123.

Reduction of 4-methoxybenzylalcohol to (4-methoxy-1,4-cyclohexadien-1-yl)methanol: The following procedure was performed for the reduction of 4-methoxybenzylalcohol to (4-methoxy-1,4-cyclohexadien-1-yl)methanol:

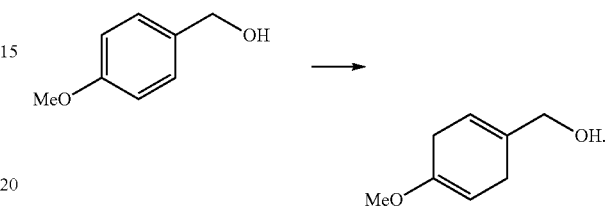

A single-neck, 100-mL round-bottom flask was equipped with a magnetic stir bar and a septum equipped with a needle connected to a bubbler as a gas outlet. 4-Methoxybenzylalcohol (1.00 g, 7.24 mmol), THF (24 mL), ethylenediamine (2.90 mL, 43.4 mmol, 6.0 equivalents), and t-BuOH (1.04 mL, 10.9 mmol, 1.5 equivalents) were added to the flask, and the resulting solution was stirred while cooling to 0° C. Lithium (151 mg, 21.7 mmol, 3.0 equivalents) was added to the solution. The reaction mixture was stirred at 0° C. (external temperature) until TLC analysis showed the reaction to be complete (60 min). Saturated aqueous NH$_4$Cl (40 mL) was added to reaction mixture (CAUTION: Evolution of hydrogen gas), and the resulting mixture was stirred until the remaining lithium was quenched. The resulting mixture was concentrated under reduced pressure with a rotary evaporator and the water bath at 25° C. until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The resulting residue was purified by flash column chromatography (SiO$_2$, 5 to 30% EtOAc in hexanes with 1% methanol) to give (4-methoxy-1,4-cyclohexadien-1-yl)methanol (548 mg, 54% yield) as a clear oil.

Data for (4-methoxy-1,4-cyclohexadien-1-yl)methanol: R$_f$=0.35 (40% EtOAc in Hex, I$_2$); $^1$H NMR (400 MHz, CDCl$_3$, 294K) δ 5.64 (app S, 1H), 4.65 (app t, 1H, J=3.3 Hz), 4.01 (s, 2H), 3.54 (s, 3H), 2.83-2.76 (m, 2H), 2.76-2.69 (m, 2H); $^{13}$C NMR (100 MHz, CDCl$_3$, 294K) δ 152.7, 135.3, 119.1, 90.2, 66.4, 53.9, 28.8, 26.7; IR (neat) 3330, 2995, 2825, 1666, 1214, 1075 cm$^{-1}$; HRMS (ESI-TOF) m/z for [M+H]$^+$ C$_8$H$_{13}$O$_2$, calculated 141.0910, found 141.0911.

Reduction of benzylalcohol to 1,4-cyclohexadien-1-ylmethanol: The following procedure was performed for the reduction of benzylalcohol to 1,4-cyclohexadien-1-ylmethanol:

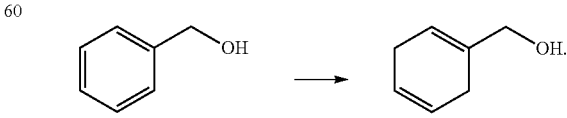

A single-neck, 100-mL round-bottom flask was equipped with a magnetic stir bar and a septum equipped with a needle connected to a bubbler as a gas outlet. Benzyl alcohol (1.00 g, 9.25 mmol), THF (30 mL), ethylenediamine (4.94 mL, 74.0 mmol, 8.0 equivalents), t-BuOH (1.33 mL, 13.9 mmol, 1.5 equivalents), and 1-methoxyadamantane (154 mg, 0.925 mmol, 0.1 equivalents) were added to the flask, and the resulting solution was stirred while cooling to 0° C. Lithium (257 mg, 37.0 mmol, 4.0 equivalents) was added to the solution. The reaction mixture was stirred at 0° C. (external temperature) until TLC analysis showed the reaction to be complete (40 min). Saturated aqueous NH$_4$Cl (40 mL) was added to reaction mixture (CAUTION: Evolution of hydrogen gas), and the resulting mixture was stirred until the remaining lithium was quenched. The resulting mixture was concentrated under reduced pressure with a rotary evaporator and the water bath at 25° C. until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The yield of 1,4-cyclohexadien-1-ylmethanol in the residue was determined to be 26% based on the internal standard.

Data for 1,4-cyclohexadien-1-ylmethanol: $^1$H NMR (300 MHz, CDCl$_3$, 294K) δ 5.75-5.72 (m, 1H), 5.72-5.64 (m, 2H) 4.00 (app s, 2H), 2.73-2.65 (m, 4H).

Reduction of 1-methylindole to 1-methylindoline: The following procedure was performed for the reduction of 1-methylindole to 1-methylindoline:

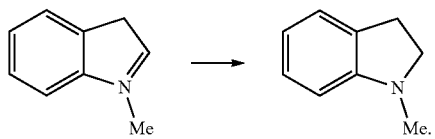

A single-neck, 100-mL round-bottom flask was equipped with a magnetic stir bar and a septum equipped with a needle connected to a bubbler as a gas outlet. 1-Methylindole (1.00 g, 7.62 mmol), THF (25 mL), and ethylenediamine (4.07 mL, 61.0 mmol, 8.0 equivalents) were added to the flask and the resulting solution was stirred while cooling to 0° C. Lithium (212 mg, 30.5 mmol, 4.0 equivalents) was added to the solution. The reaction mixture was stirred at 0° C. (external temperature) until TLC analysis showed the reaction to be complete (28 min). Saturated aqueous NH$_4$Cl (40 mL) was added to reaction mixture, and the resulting mixture was stirred until the remaining lithium was quenched. The resulting mixture was concentrated under reduced pressure with a rotary evaporator until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. The resulting yellow oil was determined to be pure by $^1$H NMR spectroscopy to give 1-methylindoline (650 mg, 63% yield) as a yellow oil.

Data for 1-methylindoline: $^1$H NMR (300 MHz, CDCl$_3$, 294K) δ 7.09 (m, 2H), 6.67 (app br t, 1H, J=7.3 Hz), 6.49 (br d, 1H, J=7.9 Hz), 3.29 (t, 2H, J=8.2 Hz), 2.94 (t, 2H, J=8.2 Hz), 2.76 (s, 3H).

Reduction of 1-methylindole to 1-methyl-4,7-dihydro-1H-indole: The following procedure was performed for the reduction of 1-methylindole to 1-methyl-4,7-dihydro-1H-indole:

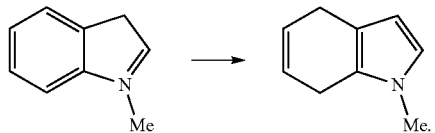

A single-neck, 100-mL round-bottom flask was equipped with a magnetic stir bar and a septum equipped with a needle connected to a bubbler as a gas outlet. 1-Methylindole (1.00 g, 7.62 mmol), THF (25 mL), ethylenediamine (4.07 mL, 61.0 mmol, 8.0 equivalents), and t-BuOH (2.19 mL, 22.9 mmol, 3.0 equivalents) were added to the flask, and the resulting solution was stirred while cooling to 0° C. Lithium (212 mg, 30.5 mmol, 4.0 equivalents) was added to the solution. The reaction mixture was stirred at 0° C. (external temperature) until TLC analysis showed the reaction to be complete (40 min). Saturated aqueous NH$_4$Cl (40 mL) was added to reaction mixture, and the resulting mixture was stirred until the remaining lithium was quenched. The resulting mixture was concentrated under reduced pressure with a rotary evaporator until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. Mesitylene (93 mg, 0.773 mmol) was added to the residue. The yield of 1-methyl-4,7-dihydro-1H-indole was determined to be 61% yield based on the external standard.

Data for 1-methyl-4,7-dihydro-JH-indole: $^1$H NMR (300 MHz, CDCl$_3$, 294K) δ 6.56 (d, 1H, J=2.3 Hz), 5.96 (d, 1H, J=2.3 Hz), 5.95-5.81 (m, 2H), 3.52 (s, 3H), 3.37-3.17 (m, 4H).

Reduction of indole to 4,7-dihydro-1H-indole: The following procedure was performed for the reduction of indole to 4,7-dihydro-1H-indole:

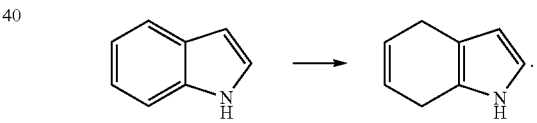

A single-neck, 100-mL round-bottom flask was equipped with a magnetic stir bar and a septum equipped with a needle connected to a bubbler as a gas outlet. Indole (1.00 g, 8.54 mmol), THF (28 mL), ethylenediamine (4.56 mL, 68.3 mmol, 8.0 equivalents), and t-BuOH (2.45 mL, 25.6 mmol, 3.0 equivalents) were added to the flask, and the resulting solution was stirred while cooling to 0° C. Lithium (237 mg, 34.1 mmol, 4.0 equivalents) was added to the solution. The reaction mixture was stirred at 0° C. (external temperature) until TLC analysis showed the reaction to be complete (40 min). Saturated aqueous NH$_4$Cl (40 mL) was added to reaction mixture, and the resulting mixture was stirred until the remaining lithium was quenched. The resulting mixture was concentrated under reduced pressure with a rotary evaporator until most THF was removed. The resulting mixture was poured to a 125-mL separatory funnel, and the product was extracted with Et$_2$O (30 mL×3). The organic extracts were combined, dried over Na$_2$SO$_4$, filtered through cotton, and concentrated under reduced pressure. Mesitylene (102 mg, 0.849 mmol) was added to the residue. The yield of 4,7-dihydro-1H-indole was determined to be 60% yield based on the external standard.

Data for 4,7-dihydro-1H-indole: ¹H NMR (300 MHz, CDCl₃, 294K) δ 7.81 (br s, 1H), 6.72 (br s, 1H), 6.06 (d, 1H, J=2.3 Hz), 5.94 (br d, 1H, J=10.5 Hz), 5.86 (br d, 1H, J=10.5 Hz), 3.29 (br s, 4H).

Reduction of acridine to 9,10-dihydroacridine: The following procedure was performed for the reduction of acridine to 9,10-dihydroacridine:

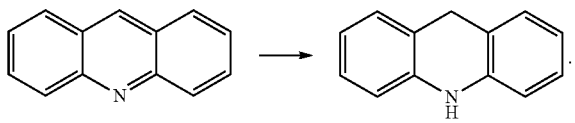 [SMILES: c1ccc2nc3ccccc3cc2c1 ; c1ccc2c(c1)Cc1ccccc1N2]

A single-neck, 100-mL round-bottom flask was equipped with a magnetic stir bar and a septum equipped with a needle connected to a bubbler as a gas outlet. Acridine (1.00 g, 5.58 mmol), THF (19 mL), ethylenediamine (2.23 mL, 33.5 mmol, 6.0 equivalents), and acetic acid (0.479 mL, 8.37 mmol, 1.5 equivalents) were added to the flask, and the resulting solution was stirred while cooling to 0° C. Lithium (120 mg, 17 mmol, 3.0 equivalents) was added to the solution. The reaction mixture was allowed to slowly warm to 25° C. until TLC analysis showed the reaction to be complete (5 h). Saturated aqueous NH₄Cl (40 mL) was added to reaction mixture, and the resulting mixture was stirred until the remaining lithium was quenched. The resulting mixture was concentrated under reduced pressure with a rotary evaporator until most THF was removed. The resulting mixture was poured to a 125-mL separatory funnel, and the product was extracted with Et₂O (30 mL×3). The organic extracts were combined, dried over Na₂SO₄, filtered through cotton, and concentrated under reduced pressure. The resulting residue was purified by flash column chromatography (SiO₂, 2.5 to 10% EtOAc in hexanes) to give 9,10-dihydroacridine (905 mg, 90% yield) as a white solid.

Data for 9,10-dihydroacridine: ¹H NMR (300 MHz, CDCl₃, 294K) δ 7.08 (m, 4H), 6.85 (td, 2H, J=7.4, 1.1 Hz), 6.66 (br d, 2H, J=7.4 Hz), 5.94 (s, 1H), 4.05 (s, 2H).).

Conversion of 2,4,6-collidine to 3,5-dimethyl-2-cyclohexen-1-one: The following procedure was performed for the conversion of 2,4,6-collidine to 3,5-dimethyl-2-cyclohexen-1-one:

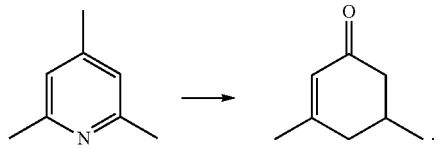

A single-neck, 100-mL round-bottom flask was equipped with a magnetic stir bar and a septum equipped with a needle connected to a bubbler as a gas outlet. 2,4,6-Collidine (1.00 g, 8.25 mmol), THF (28.0 mL), and ethylenediamine (4.41 mL, 66.0 mmol, 8.0 equivalents) were added to the flask, and the resulting mixture was cooled to 0° C. while stifling. Lithium (229 mg, 33.0 mmol, 4.0 equivalents) was added to the solution. The reaction mixture was stirred at 0° C. (external temperature) until TLC analysis showed the reaction to be complete (60 min). During this time, the reaction went from clear to yellow to deep blue to clear yellow. The reaction mixture was concentrated under reduced pressure with a rotary evaporator until most THF was removed and kept under N₂. The resulting yellow residue was dissolved in EtOH (34 mL) under N₂. NaOH (990 mg, 24.8 mmol, 3.0 equivalents) was dissolved in water (20 mL), and the resulting aqueous NaOH solution was added to the EtOH solution. The reaction mixture was left to stir under an N₂ atmosphere for 2.5 h. The reaction mixture was acidified with concentrated HCl (15 mL). The resulting mixture was poured to a 250-mL separatory funnel, and the product was extracted with Et₂O (30 mL×3). The organic extracts were combined, washed with saturated aqueous NaHCO₃ (30 mL×2) and brine (30 mL). The resulting organic extracts were dried over Na₂SO₄, filtered through cotton, and concentrated under reduced pressure. 1-Methoxyadamantane (0.158 g, 0.950 mmol) was added to the residue and the yield of 3,5-dimethyl-2-cyclohexen-1-one in the residue was determined to be 60% based on the external standard.

Data for 3,5-dimethyl-2-cyclohexen-1-one: ¹H NMR (400 MHz, CDCl₃, 294K) δ 5.86 (s, 1H), 2.40 (dd, 1H, J=16.5, 3.7 Hz), 2.28 (dd, 1H, J=16.5, 4.2 Hz), 2.23-1.98 (m, 3H) 1.95 (s, 3H), 1.05 (d, 3H, J=6.5 Hz).

Conversion of 2,5-dihydrofuran to (Z)-2-buten-1-ol: The following procedure was performed for the reduction of 2,5-dihydrofuran to (Z)-2-buten-1-ol:

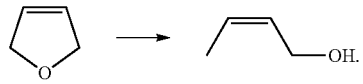

A single-neck, 100-mL round-bottom flask was equipped with a magnetic stir bar and a septum equipped with a needle connected to a bubbler as a gas outlet. 2,5-Dihydrofuran (1.00 g, 14.3 mmol), THF (48 mL), ethylenediamine (4.76 mL, 71.3 mmol, 5 equivalents), and 1-methoxyadamantane (273 mg, 1.43 mmol, 0.1 equivalents, internal standard) were added to the flask, and the resulting solution was stirred while cooling to 0° C. Lithium (248 mg, 35.7 mmol, 2.5 equivalents) was added to the solution. The reaction mixture was stirred at 0° C. (external temperature) until TLC analysis showed the reaction to be complete (30 min). Saturated aqueous NH₄Cl (40 mL) was added to reaction mixture, and the resulting mixture was stirred until the remaining lithium was quenched. The resulting mixture was concentrated under reduced pressure with a rotary evaporator and the water bath at 25° C. until most THF was removed. The resulting mixture was poured to a 125-mL separatory funnel, and the product was extracted with Et₂O (30 mL×3). The organic extracts were combined, washed with brine, dried over Na₂SO₄, filtered through cotton, and concentrated under reduced pressure and the water bath at 25° C. until most THF was removed. The yield of (Z)-2-buten-1-ol in the residue was determined to be 41% based on the internal standard.

Data for (Z)-2-buten-1-ol: ¹H NMR (300 MHz, CDCl₃, 294K) δ 5.67-5.51 (m, 2H), 4.25-4.10 (m, 2H), 1.65 (d, 3H, J=4.5 Hz).

Conversion of octadecylamine to 4-methyl-N-octadecylbenzenesulfonamide: The following procedure was performed for the conversion of octadecylamine to 4-methyl-N-octadecylbenzene sulfonamide:

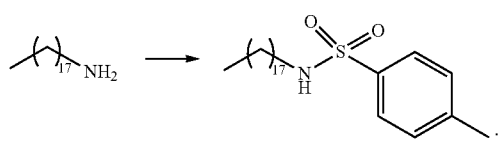

A single-neck, 250-mL round-bottom flask was equipped with a magnetic stir bar and a septum equipped with a needle connected to a nitrogen inlet. 1-Octadecylamine (5.00 g, 18.6 mmol) was dissolved in $CH_2Cl_2$ (62 mL) under $N_2$. p-Toluenesulfonyl chloride (3.89 g, 20.4 mmol, 1.1 equivalents) and Et 3 N (6.47 mL, 46.4 mmol, 2.5 equivalents) were added to the solution. The reaction mixture was stirred at 24° C. for 19 h. A 4 M aqueous solution of HCl (80 mL) was added to the reaction mixture, and the resulting solution was poured to a 250-mL separatory funnel. The layers were separated, and the aqueous layer was extracted with $CH_2Cl_2$ (50 mL×2). The organic extracts were combined, dried over $Na_2SO_4$, filtered through cotton, and concentrated under reduced pressure. The resulting residue was purified by flash column chromatography ($SiO_2$, 2.5 to 50% EtOAc in hexanes) to give 4-methyl-N-octadecylbenzenesulfonamide (7.00 g, 89% yield) as a white solid.

Data for 4-methyl-N-octadecylbenzenesulfonamide: $R_f$=0.23 (10% EtOAc in hexanes); $^1$H NMR (300 MHz, $CDCl_3$, 294K) δ 7.75 (d, 2H, J=8.3 Hz), 7.31 (d, 2H, J=8.3 Hz), 4.26 (t, 1H, J=6.0 Hz), 2.93 (q, 2H, J=6.8 Hz), 2.43 (s, 3H), 1.44 (quint, 2H, J=6.8 Hz), 1.34-1.14 (m, 29H), 0.88 (t, 3H, J=6.8 Hz); $^{13}$C NMR (75 MHz, $CDCl_3$, 294K) δ 143.3, 137.0, 129.7, 127.1, 77.2, 50.0, 49.7, 49.4, 43.1, 42.0, 31.9, 29.7, 29.64, 29.61, 29.5, 29.4, 29.3, 29.1, 26.5, 22.7, 21.5, 14.1; IR (neat) 3286, 2914, 2848, 1328, 1157, 812, 669 $cm^{-1}$; HRMS (ESI-TOF) m/z for $[M+H]^+$ $C_{25}H_{46}O_2NS$, calcd 424.32438, found 424.32241.

Conversion of 4-methyl-N-octadecylbenzenesulfonamide to 1-octadecanamine: The following procedure was performed for the conversion of 4-methyl-N-octadecylbenzene sulfonamide to 1-octadecanamine:

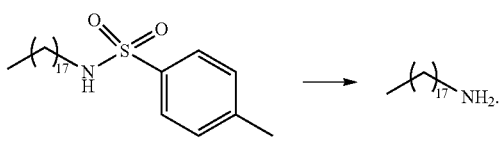

A single-neck, 100-mL round-bottom flask was equipped with a magnetic stir bar and a septum equipped with a needle connected to a bubbler as a gas outlet. 4-Methyl-N-octadecylbenzenesulfonamide (1.00 g, 2.36 mmol), THF (8 mL), ethylenediamine (2.21 mL, 33.0 mmol, 14 equivalents), and 1-methoxyadamantane (63.0 mg, 0.236 mmol, 0.1 equiv, internal standard) were added to the flask, and the resulting solution was stirred while cooling to 0° C. Lithium (115 mg, 16.5 mmol, 7.0 equivalents) was added to the solution. The reaction mixture was stirred at 0° C. (external temperature) until TLC analysis showed the reaction to be complete (31 min). Water (30 mL) was added to reaction mixture, and the resulting mixture was stirred until the remaining lithium was quenched. The resulting mixture was concentrated under reduced pressure with a rotary evaporator until most THF was removed. The resulting mixture was poured to a 125-mL separatory funnel, and the product was extracted with $Et_2O$ (30 mL×3). The organic extracts were combined, washed with brine, dried over $Na_2SO_4$, filtered through cotton, and concentrated under reduced pressure. The yield of 1-octadecylamine in the residue was determined to be 100% based on the internal standard.

Data for 1-octadecylamine: $^1$H NMR (300 MHz, $CDCl_3$, 294K) δ 2.64 (t, 2H, J=7.5 Hz), 1.46-1.36 (m, 2H), 1.33-1.16 (m, 29H), 0.86 (t, 3H, J=7.5 Hz).

Preparation of a mixture of trans-N-benzylpilolactam and cis-N-benzylpilolactam and subsequent debenzylation: The following procedure was performed for the preparation of a mixture of trans-N-benzylpilolactam and cis-N-benzylpilolactam and subsequent debenzylation:

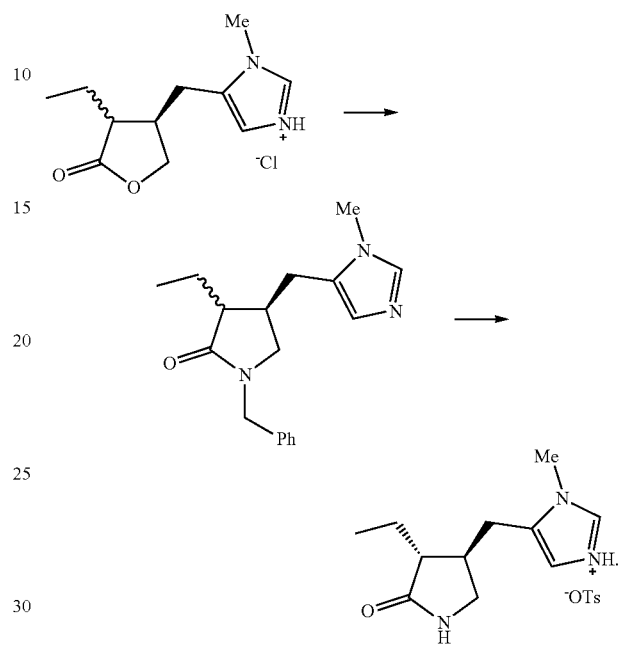

A single-neck, 50-mL round-bottom flask was equipped with a magnetic stir bar, a reflux condenser, and a septum equipped with a needle connected to a nitrogen inlet. Pilocarpine hydrochloride (4.00 g, 16.4 mmol) was dissolved in benzylamine (12.5 mL, 114 mmol, 7 equivalents) under $N_2$, and the resulting solution was heated to reflux for 72 h with a sand bath. The reaction mixture was cooled to room temperature and diluted with 3 M NaOH (15 mL). The resulting solution was poured to a 125-mL separatory funnel, and the layers were separated. The aqueous solution was extracted with $CH_2Cl_2$ (30 mL×3). The organic extracts were combined, washed with water (50 mL×2), dried over $Na_2SO_4$, filtered through cotton, and concentrated under reduced pressure. The benzylamine was distilled under reduced pressure (5 mmHg, boiling point: 63° C.). The resulting residue was purified by flash column chromatography ($SiO_2$, 5 to 100% EtOAc in hexanes to 5 to 50% MeOH in EtOAc) to give a mixture of trans-N-benzylpilolactam and cis-N-benzylpilolactam (2.84 g, 58% yield) as an orange oil.

Reduction of (3R,4R)-1-benzyl-3-ethyl-4-((1-methyl-1H-imidazol-5-yl)methyl)pyrrolidin-2-one to 5-(((3R,4R)-4-ethyl-5-oxopyrrolidin-3-yl)methyl)-1-methyl-1H-imidazol-3-ium 4-methylbenzenesulfonate: The following procedure was performed for the reduction of (3R,4R)-1-benzyl-3-ethyl-4-((1-methyl-1H-imidazol-5-yl)methyl)pyrrolidin-2-one to 5-(((3R,4R)-4-ethyl-5-oxop yrrolidin-3-yl)methyl)-1-methyl-1H-imidazol-3-ium 4-methylbenzenesulfonate. A single-neck, 100-mL round-bottom flask was equipped with a magnetic stir bar and a septum equipped with a needle connected to a bubbler as a gas outlet. (3R,4R)-1-benzyl-3-ethyl-4-((1-methyl-1H-imidazol-5-yl)methyl)pyrrolidin-2-one (1.00 g, 3.36 mmol), THF (12 mL), and ethylenediamine (4.50 mL, 67.3 mmol, 20 equivalents) were added to the flask, and the resulting solution was stirred while cooling to 0° C. Lithium (233 mg, 33.6 mmol, 10 equivalents) was added to the solution. The reaction mixture was stirred at 0° C. (external temperature) until TLC analysis showed the reaction to be complete (45 min). Water (30 mL) was added to reaction mixture, and the resulting mixture was stirred until the remaining lithium was quenched. The resulting mixture was concentrated under reduced pressure with a rotary evaporator until most THF was removed. The resulting mixture was poured to a 125-mL separatory funnel, and the solution was extracted with $Et_2O$ (20 mL×2). The resulting organic extracts were discarded. The resulting aqueous solution was extracted with $CHCl_3$ (20 mL×4). The resulting organic extracts were dried over $Na_2SO_4$, filtered through cotton, and concentrated under reduced pressure. The resulting residue was dissolved in acetone (6 mL) and filtered through cotton into a 25-mL round-bottom flask equipped with a magnetic stir bar and a septum connected to a nitrogen inlet, and the resulting solution was stirred while cooling to 0° C. under a nitrogen atmosphere. p-Toluenesulfonic acid monohydrate (0.95 g, 5.00 mmol) was dissolved in acetone (3 mL), and added to the cooled solution of residue dropwise over 15 min. When addition was complete, the resulting mixture was stirred for an additional 20 min at 0° C. The resulting mixture was filtered through paper, washing the solid with cold acetone, dried under air atmosphere at 25° C., and then dried further under high vacuum. The NMR of the white solid was shown to be pure 5-(((3R,4R)-4-ethyl-5-oxopyrrolidin-3-yl)methyl)-1-methyl-1H-imidazol-3-ium 4-methylbenzenesulfonate (410 mg, 32%).

Data for 5-(((3R,4R)-4-ethyl-5-oxopyrrolidin-3-yl)methyl)-1-methyl-1H-imidazol-3-ium 4-methylbenzenesulfonate: $^1$H NMR (300 MHz, DMSO-d6, 294K) δ 14.02 (br s, 1H), 9.00 (s, 1H), 7.61 (s, 1H), 7.55 (s, 1H), 7.49 (d, 2H, J=8.0 Hz), 7.12 (d, 2H, J=8.0 Hz), 3.78 (s, 3H), 3.33 (br t, 1H, J=8.5 Hz), 2.96-2.69 (m, 3H), 2.47-2.36 (m, 1H), 2.29 (s, 3H), 2.00 (br q, 1H, J=6.0 Hz), 1.63-1.45 (m, 2H), 0.88 (t, 3H, J=7.5 Hz). 500-mmol scale:

Reduction of benzoic acid to 1,4-dihydrobenzoic acid: The following procedure was performed for the reduction of benzoic acid to 1,4-dihydrobenzoic acid:

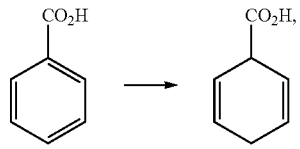 [SMILES: O=C(O)c1ccccc1 ; O=C(O)C1C=CCC=C1]

on a 500-mmol scale. A three-neck, 3-L round-bottom flask was equipped with a mechanical stirrer, addition funnel, low-temperature thermometer, and a 3-way adaptor connected to a nitrogen inlet. The flask was cooled to 0° C., to which lithium (10.4 g, 1.50 mol, 3.0 equivalents) was added. The addition funnel was charged with THF (570 mL), and the THF was slowly added to the lithium solid while cooling the suspension of lithium in THF to 0° C. (internal temperature) on an ice bath. A solution of benzoic acid (61.10 g, 500 mmol) and ethylenediamine (200 mL, 3.00 mol, 6.0 equivalents) in THF (260 mL) was prepared in a separate Erlenmeyer flask and transferred to the addition funnel. The solution was then added to the suspension of lithium in THF over 16 min while keeping the internal temperature below 26° C. on an ice bath. The reaction mixture was stirred at 10-26° C. (internal temperature) on an ice bath until TLC analysis showed the reaction to be complete (15 min). Saturated aqueous $NH_4Cl$ (500 mL) was slowly added to the reaction mixture over 8 min while keeping the internal temperature below 26° C. The resulting mixture was acidified with concentrated HCl until pH=2 while keeping the internal temperature below 26° C. The mixture was concentrated under reduced pressure with a rotary evaporator until most THF was removed. The resulting mixture was poured to a 2000-mL separatory funnel, and the product was extracted with $Et_2O$ (200 mL×3). The organic extracts were combined, dried over $Na_2SO_4$, filtered through cotton, and concentrated under reduced pressure to give 1,4-dihydrobenzoic acid as a pale-yellow oil (59.6 g, 95% yield).

Data for 1,4-dihydrobenzoic acid: $^1$H NMR (300 MHz, CDCl$_3$, 294K) δ 11.52 (br s, 1H, COOH), 5.93 (m, 2H, C$_3$—H), 5.83 (m, 2H, C$_2$—H), 3.78 (m, 1H, C$_1$—H), 2.70 (m, 2H, C$_4$—H).

Reduction of benzoic acid to 1,4-dihydrobenzoic acid in presence of n-butoxybenzene: The following procedure was performed for the reduction of benzoic acid to 1,4-dihydrobenzoic acid in presence of n-butoxybenzene:

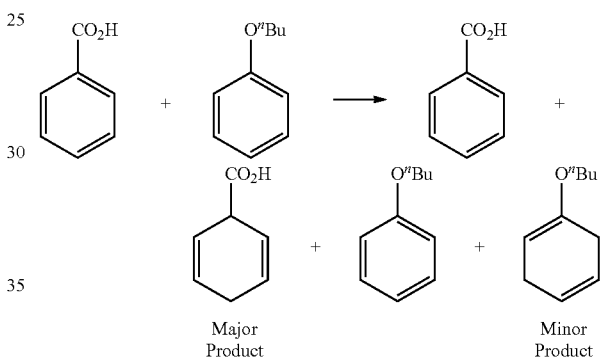

A 20-mL scintillation vial was equipped with a magnetic stir bar and a septum equipped with a needle connected to a bubbler as a gas outlet. Benzoic acid (122 mg, 1.00 mmol), n-butoxybenzene (150 mg, 1.00 mmol), 1-methoxyadamantane (33 mg, 0.200 mmol), THF (3 mL), and ethylenediamine (0.400 mL, 6.00 mmol, 6.0 equivalents) were added to the vial, and the resulting mixture was cooled to 0° C. while stirring. Lithium (17 mg, 2.50 mmol, 2.5 equivalents) was added to the solution. The reaction mixture was stirred at 0° C. (external temperature) for 1 h. Saturated aqueous $NH_4Cl$ (4 mL) was added to the reaction mixture, and the resulting mixture was stirred until the remaining lithium was quenched. The resulting mixture was concentrated under reduced pressure with a rotary evaporator until most THF was removed. The resulting mixture was extracted with $Et_2O$ (6 mL×2). The organic extracts were combined and concentrated under reduced pressure. The leftover aqueous solution was cooled with an ice bath and acidified with concentrated HCl until pH=2. The resulting mixture was extracted with $Et_2O$ (6 mL×2). The organic extracts were combined, and concentrated (separately from the first extraction) under reduced pressure. The yields of all components were determined from the internal standard.

Reduction of n-butoxybenzene to 1-butoxy-1,4-cyclohexadiene in presence of benzoic acid: The following procedure was performed for the reduction of n-butoxybenzene to 1-butoxy-1,4-cyclohexadiene in presence of benzoic acid:

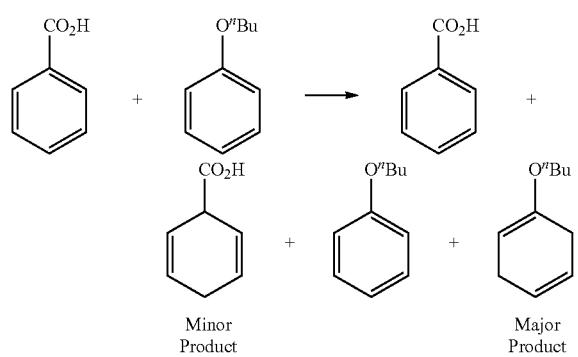

Minor Product     Major Product

A 20-mL scintillation vial was equipped with a magnetic stir bar and a septum equipped with a needle connected to a bubbler as a gas outlet. Benzoic acid (122 mg, 1.00 mmol), n-butoxybenzene (150 mg, 1.00 mmol), 1-methoxyadamantane (33 mg, 0.200 mmol), THF (3 mL), triethylenetetramine (0.893 mL, 6.00 mmol, 6.0 equivalents), and t-BuOH (0.239 mL, 2.50 mmol, 2.5 equivalents) were added to the vial, and the resulting mixture was cooled to 0° C. while stirring. Lithium (21 mg, 3.00 mmol, 3.0 equivalents) was added to the solution. The reaction mixture was stirred at 0° C. (external temperature) for 1 h. Saturated aqueous $NH_4Cl$ (4 mL) was added to the reaction mixture, and the resulting mixture was stirred until the remaining lithium was quenched. The resulting mixture was concentrated under reduced pressure with a rotary evaporator until most THF was removed. The resulting mixture was extracted with $Et_2O$ (6 mL×2). The organic extracts were combined and concentrated under reduced pressure. The leftover aqueous solution was cooled with an ice bath and acidified with concentrated HCl until pH=2. The resulting mixture was extracted with $Et_2O$ (6 mL×2). The organic extracts were combined, and concentrated (separately from the first extraction) under reduced pressure. The yields of all components were determined from the internal standard.

Conversion of benzoic acid to methyl 1-(3-oxobutyl)-2,5-cyclohexadiene-1-carboxylate: The following procedure was performed for the conversion of benzoic acid to methyl 1-(3-oxobutyl)-2,5-cyclohexadiene-1-carboxylate:

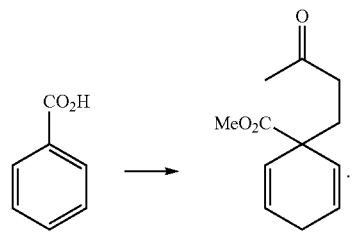

A single-neck, 25-mL round-bottom flask was equipped with a magnetic stir bar and a septum equipped with a needle connected to a bubbler as a gas outlet. Benzoic acid (200 mg, 1.64 mmol), THF (5.00 mL), and ethylenediamine (0.656 mL, 9.83 mmol, 6.0 equivalents) were added to the flask, and the resulting mixture was cooled to 0° C. while stirring. Lithium (34 mg, 24.2 mmol, 3.0 equivalents) was added to the solution. The reaction mixture was stirred at 0° C. (external temperature) for 1 h. The color of the reaction mixture changed from clear to yellow to deep green/blue to yellow. CuI (3.12 g, 16.4 mmol, 10 equivalents) was added to the reaction mixture then 3-buten-2-one (1.36 mL, 16.4 mmol, 10 equivalents) was added dropwise over 5 min to the reaction mixture. The reaction mixture was allowed to slowly warm to 23° C. over 1.5 h with continued stirring. The reaction mixture was quenched with saturated aqueous $NH_4Cl$ (5 mL) and acidified with concentrated HCl until pH=2. The resulting mixture was concentrated under reduced pressure with a rotary evaporator until most THF was removed. The resulting mixture was diluted with $H_2O$ (5 mL) and $Et_2O$ (10 mL), and the resulting mixture was filtered through celite, washing the cake with $Et_2O$ (10 mL). The resulting filtrate was filtered through celite a second time due to an emulsion, further washing the cake with $Et_2O$ (10 mL). The resulting mixture was poured to a 60-mL separatory funnel, and the product was extracted with $Et_2O$ (10 mL×4). The organic extracts were combined, dried over $Na_2SO_4$, filtered through cotton, and concentrated under reduced pressure to give a yellow oil residue. A single neck, 25-mL round-bottom flask was equipped with a magnetic stir bar and a septum equipped with a needle connected to a nitrogen inlet. The resulting residue was dissolved in $Et_2O$ (5 mL) and placed in the pre-equipped round-bottom flask under $N_2$. The resulting mixture was cooled to 0° C. while stirring. (Trimethylsilyl)-diazomethane (0.820 mL, 1.37 mmol, 1 equivalents, 2M) was added to the reaction mixture dropwise over 1 minute. The reaction mixture was allowed to stir at 24° C. for 1.5 h and concentrated under reduced pressure. The resulting residue was purified by flash column chromatography ($SiO_2$, 5 to 40% EtOAc in hexanes) to give methyl 1-(3-oxobutyl)-2,5-cyclohexadiene-1-carboxylate (67.0 mg, 20% yield) as a yellow oil.

Data for methyl 1-(3-oxobutyl)-2,5-cyclohexadiene-1-carboxylate: $R_f$=0.19 (20% EtOAc in hexanes stained with $I_2$, $KMnO_4$); $^1H$ NMR (500 MHz, $CDCl_3$, 294K) δ 5.95-5.90 (app dt, 2H, J=10.4, 3.5 Hz), 5.71-5.65 (dt, 2H, J=10.5, 2.0 Hz), 3.70 (s, 3H), 2.69-2.63 (mult, 2H), 2.36 (t, 2H, J=8.5 Hz), 2.12 (s, 3H), 2.01-1.95 (t, 2H, J=8.5 Hz); $^{13}C$ NMR (125 MHz, $CDCl_3$, 294K) δ 208.2, 174.8, 126.6, 126.5, 123.9, 52.3, 47.2, 38,7, 32.6, 30.1, 26.1; IR (neat) 3031, 2952, 1715, 1670, 1229 $cm^{-1}$; HRMS (ESI-TOF) m/z for $[M+H]^+$ $C_{12}H_{27}O_3$, calculated 209.11722, found 209.11723.

Having described this invention, it will be understood to those of ordinary skill in the art that the same can be performed within a wide and equivalent range of conditions, formulations and other parameters without affecting the scope of the invention or any embodiment thereof.

The invention claimed is:

1. A method of reducing an aromatic ring or a cyclic, allylic ether in a compound, comprising:
   preparing a reaction mixture comprising a compound comprising an aromatic moiety or a cyclic, allylic ether moiety, an alkali metal, an alcohol, and either ethylenediamine or diethylenetriamine, in an ether solvent; and
   reacting the reaction mixture at from −20° C. to 30° C. for a time sufficient to reduce a double bond in the aromatic moiety to a single bond or to reduce the cyclic, allylic ether moiety.

2. The method of claim 1, wherein the alcohol is a $C_2$-$C_6$ alkyl alcohol.

3. The method of claim 2, wherein the alcohol is a secondary or tertiary alcohol.

4. The method of claim 3, wherein the alcohol comprises isopropyl alcohol, t-butyl alcohol, or t-amyl alcohol.

5. The method of claim 1, wherein the alkali metal is Li.

6. The method of claim 1, wherein the aromatic moiety is a phenyl moiety or a fused benzene ring of a polycyclic aromatic moiety.

7. The method of claim 1, wherein the aromatic moiety is a $C_6$-aryl or a substituted $C_6$-aryl.

8. The method of claim 1, wherein the aromatic moiety is substituted with a $C_1$-$C_6$ carboxylic acid.

9. The method of claim 1, the aromatic moiety is substituted with a $C_1$-$C_6$ alkoxyl group.

10. The method of claim 1, wherein the aromatic moiety is a carbonyl-substituted $C_1$-$C_6$ alkyl group or a structural isomer thereof.

11. The method of claim 1, wherein the compound comprising an aromatic moiety or a cyclic, allylic ether moiety is n-butyl phenyl ether.

12. The method of claim 1, wherein the reaction is performed for a length of time sufficient to yield at least 50% yield of the product of the conversion of the double bond in the aromatic moiety to a single bond.

13. The method of claim 1, wherein the ether solvent is a saturated cyclic ether, or 1,4-dioxane, or a derivative thereof, wherein the derivative optionally can be alkyl-substituted or halo-substituted.

14. The method of claim 1, wherein the ethylenediamine:compound molar ratio or the diethylenetriamine:compound molar ratio in the reaction mixture ranges from 2-20:1.

15. The method of claim 1, wherein the ethylenediamine:alkali metal molar ratio or the diethylenetriamine:alkali metal molar ratio is approximately or about 2:1.

16. The method of claim 1, wherein the reaction mixture is reacted at a temperature ranging from 0° C. to 10° C.

17. The method of claim 1, wherein the compound comprises an aromatic moiety.

18. The method of claim 1, wherein the compound comprises a cyclic, allylic ether moiety.

* * * * *